United States Patent
Araki et al.

(10) Patent No.: US 8,710,090 B2
(45) Date of Patent: Apr. 29, 2014

(54) AZOLE DERIVATIVES, METHODS FOR PRODUCING THE SAME, INTERMEDIATE THEREOF, AGRO-HORTICULTURAL AGENTS

(75) Inventors: Nobuyuki Araki, Tokyo (JP); Toru Yamazaki, Tokyo (JP); Nobuyuki Kusano, Tokyo (JP); Eiyu Imai, Tokyo (JP); Hisashi Kanno, Tokyo (JP); Masaru Mori, Tokyo (JP); Taiji Miyake, Tokyo (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 13/508,269

(22) PCT Filed: Dec. 7, 2010

(86) PCT No.: PCT/JP2010/007118
§ 371 (c)(1),
(2), (4) Date: May 25, 2012

(87) PCT Pub. No.: WO2011/070771
PCT Pub. Date: Jun. 16, 2011

(65) Prior Publication Data
US 2012/0232286 A1 Sep. 13, 2012

(30) Foreign Application Priority Data

Dec. 8, 2009 (JP) .................. 2009-278593

(51) Int. Cl.
*A01N 43/50* (2006.01)
*A61K 31/4164* (2006.01)
*C07D 233/60* (2006.01)
*C07D 249/08* (2006.01)

(52) U.S. Cl.
USPC .......................................... 514/383; 514/396

(58) Field of Classification Search
USPC ................ 514/383, 396; 548/262.2, 346.1
See application file for complete search history.

(56) References Cited

U.S. PATENT DOCUMENTS

| | | | | |
|---|---|---|---|---|
| 4,938,792 A | * | 7/1990 | Kumazawa et al. | 504/272 |
| 5,028,254 A | * | 7/1991 | Kumazawa et al. | 504/275 |
| 5,159,118 A | * | 10/1992 | Kumazawa et al. | 568/330 |
| 5,162,356 A | * | 11/1992 | Arahira et al. | 514/383 |
| 5,239,089 A | * | 8/1993 | Kumazawa et al. | 549/332 |
| 5,292,764 A | * | 3/1994 | Arahira et al. | 514/383 |
| 5,414,105 A | * | 5/1995 | Kumazawa et al. | 560/51 |
| 5,504,096 A | * | 4/1996 | Arahira et al. | 514/365 |
| 2012/0238762 A1 | * | 9/2012 | Sudo et al. | 548/268.2 |

FOREIGN PATENT DOCUMENTS

| | | |
|---|---|---|
| DE | 3902031 A1 | 7/1990 |
| EP | 0267778 A2 | 5/1988 |
| EP | 0329397 A1 | 8/1989 |
| JP | 1-93574 A | 4/1989 |
| JP | 1-186871 A | 7/1989 |
| JP | 1-301664 A | 12/1989 |
| JP | 5-271197 A | 10/1993 |

OTHER PUBLICATIONS

Chuman, et al., Quantitative Structure-Activity Relationships (QSAR), vol. 17, Issue 04, 1998, p. 316, Table 1, Compound 19.*
Patani et al., Chem Rev, 1996, vol. 96 (8), especially p. 3149.*
International Search Report issued in PCT/JP2010/007118, dated Mar. 25, 2011.

* cited by examiner

*Primary Examiner* — Rebecca Anderson
*Assistant Examiner* — Karen Cheng
(74) *Attorney, Agent, or Firm* — Birch, Stewart, Kolasch & Birch LLP

(57) ABSTRACT

An azole derivative according to the invention is represented by Formula (I), wherein each of $R^a$ and $R^b$ denotes a hydrogen atom, or a $C_1$-$C_6$ alkyl group, a $C_2$-$C_6$ alkenyl group or a $C_2$-$C_6$ alkynyl group; $R^a$ and $R^b$ may be substituted with $X^a$ or $X^b$ which is a halogen atom; each of $n^a$ and $n^b$ denotes 0 or the number of $X^a$- or $X^b$-substituted hydrogen atoms among the hydrogen atoms in $R^a$ or $R^b$; each Y denotes a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a phenyl group, a cyano group or a nitro group; m denotes 0 to 5; and A denotes a nitrogen atom or a methyne group. As a result, an azole derivative contained as an active ingredient in an agro-horticultural agent having an excellent controlling effect on diseases can be provided.

(I)

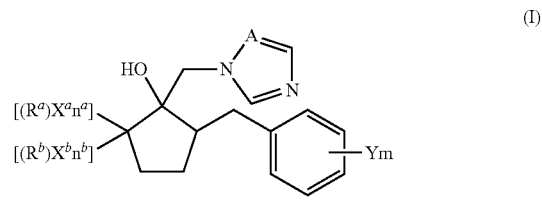

8 Claims, No Drawings

AZOLE DERIVATIVES, METHODS FOR PRODUCING THE SAME, INTERMEDIATE THEREOF, AGRO-HORTICULTURAL AGENTS

TECHNICAL FIELD

The present invention relates to a novel azole derivative. It also relates to an agro-horticultural agent and an industrial material protecting agent containing the derivative as an active ingredient as well as method for producing the derivatives.

BACKGROUND ART

A certain 2-substituted-benzyl-1-azolylmethylcyclopentanol derivative is known to have a biocidal activity (for example, see Patent Literatures 1 and 2).

Some compounds included in a 2-(halogenated hydrocarbon-substituted)-5-benzyl-1-azolylmethylcyclopentanol derivative are reported to exhibit anti-convulsive and anti-anxiolytic activities (see Patent Literature 3). Nevertheless, Patent Literature 3 contains no description with regard to agro-horticultural agents and industrial material protecting agents, and no specific disclosure of the compounds encompassed by the invention.

CITATION LIST

Patent Literature

[PTL 1] Japanese Unexamined Patent Application Publication No. 01-93574
[PTL 2] Japanese Unexamined Patent Application Publication No. 01-186871
[PTL 3] German Patent Application, Publication No. 3902031 Specification
[PTL 4] Japanese Unexamined Patent Application Publication No. 05-271197
[PTL 5] Japanese Unexamined Patent Application Publication No. 01-301664

SUMMARY OF INVENTION

Technical Problem

Conventionally, an agro-horticultural pesticide having a low toxicity to humans and animals, capable of being handled safely, and exhibiting a high controlling effect on a wide range of plant diseases has been desired. Also, there has been a need for a plant growth regulator which regulates the growth of a variety of crops and horticultural plants thereby exhibiting yield-increasing and quality-improving effects, or an industrial material protecting agent which protects an industrial material from a wide range of hazardous microorganisms which invade such materials.

Accordingly, the present invention aims primarily at providing an agro-horticultural agent and an industrial material which fulfill the need described above.

Solution to Problem

To achieve the aim mentioned above, we made an extensive study on chemical structures and biological activities of 2-(halogenated hydrocarbon-substituted)-5-benzyl-1-azolylmethylcyclopentanol derivatives. As a result, we found that an azole derivative (specifically, 2-(halogenated hydrocarbon-substituted)-5-benzyl-1-azolylmethylcyclopentanol derivative) represented by Formula (I) shown below has an excellent activity, thus establishing the present invention. The invention is based on such novel findings, and includes the following inventive aspects.

Thus, an azole derivative according to the invention has a structure represented by Formula (I):

[Chem. 1]

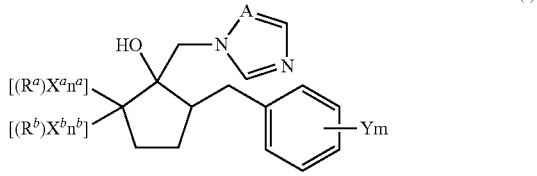

wherein each of $R^a$ and $R^b$ independently denotes a hydrogen atom, or a $C_1$-$C_6$ alkyl group, a $C_2$-$C_6$ alkenyl group or a $C_2$-$C_6$ alkynyl group; provided that $R^a$ and $R^b$ are not hydrogen atoms at the same time, and the hydrogen atoms of the alkyl group, the alkenyl group and the alkynyl group may be substituted with $X^a$ or $X^b$;

each of $X^a$ and $X^b$ denotes a halogen atom;

$n^a$ denotes 0 or the number of $X^a$-substituted hydrogen atoms among the hydrogen atoms in $R^a$;

$n^b$ denotes 0 or the number of $X^b$-substituted hydrogen atoms among the hydrogen atoms in $R^b$;

provided that "$n^a+n^b$" is 1 or more; when $n^a$ is 2 or more, then each $X^a$ may be same or different; when $n^b$ is 2 or more, then each $X^b$ may be same or different;

each Y denotes a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a phenyl group, a cyano group or a nitro group;

m denotes 0 to 5; when m is 2 or more, each Y may be same or different;

A denotes a nitrogen atom or a methyne group.

As a result of having the structure shown above, the azole derivative according to the invention is advantageous in exhibiting an excellent biocidal effect on a large number of microorganisms which induce diseases in plants.

The azole derivative according to the invention is preferable when each of the alkyl group, the alkenyl group and the alkynyl group in $R^a$ and $R^b$ in Formula (I) described above denotes a $C_1$-$C_4$ alkyl group, a $C_2$-$C_4$ alkenyl group and a $C_2$-$C_4$ alkynyl group; each of $X^a$ and $X^b$ denotes a fluorine atom, a chlorine atom or a bromine atom; each of $n^a$ and $n^b$ denotes 0 to 5; each Y denotes a halogen atom, a $C_1$-$C_3$ alkyl group, a $C_1$-$C_3$ haloalkyl group, a $C_1$-$C_3$ alkoxy group or a $C_1$-$C_3$ haloalkoxy group; m denotes 0 to 3; and A denotes a nitrogen atom.

The azole derivative according to the invention is preferable when the alkyl group in $R^a$ and $R^b$ in Formula (I) described above denotes a $C_1$-$C_3$ alkyl group; each of $X^a$ and $X^b$ denotes a chlorine atom or a bromine atom; each of $n^a$ and $n^b$ denotes 0 to 3; each Y denotes a halogen atom, a $C_1$-$C_2$ haloalkyl group or a $C_1$-$C_2$ haloalkoxy group; and m denotes 0 to 2.

The azole derivative according to the invention is preferable when all of $n^a$, $n^b$ and m in Formula (I) described above denote 0 to 1 and Y is a halogen atom.

The invention also includes the following intermediates of the azole derivatives.

The intermediate compound of the azole derivatives according to the invention is a 3-hydroxymethyl-2-oxocyclopentane carboxylic acid ester derivative represented by Formula (XI):

[Chem. 2]

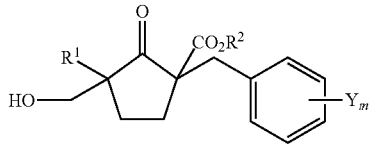

(XI)

wherein $R^1$ denotes a $C_1$-$C_6$ alkyl group, a $C_2$-$C_6$ alkenyl group or a $C_2$-$C_6$ alkynyl group; and $R^2$ denotes a $C_1$-$C_4$ alkyl group.

Also, the intermediate compound of the azole derivatives according to the invention is an oxetane compound represented by Formula (XVI):

[Chem. 3]

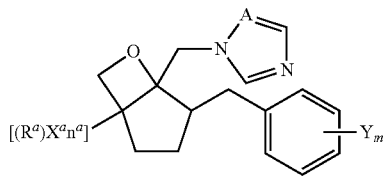

(XVI)

Also, the intermediate of the azole derivatives according to the invention is an oxetane sulfone ester derivative represented by Formula (XX):

[Chem. 4]

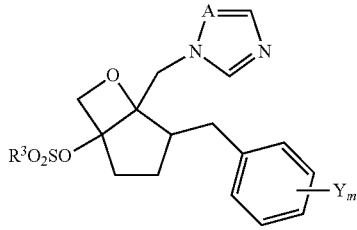

(XX)

wherein $R^3$ denotes a lower alkyl group, or an optionally substituted phenyl group or naphthyl group.

The invention further includes the following inventions as methods for producing the azole derivatives shown above.

A method for producing the azole derivative according to the invention comprises a step for substituting a halogen atom-substitutable leaving group in an intermediate compound represented by Formula (II) with a halogen atom thereby obtaining a compound represented by Formula (Ia):

[Chem. 5]

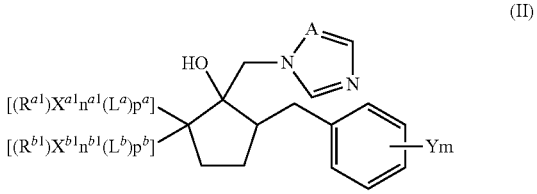

(II)

[Chem. 6]

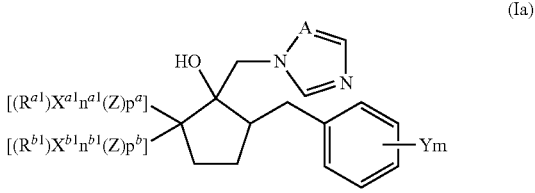

(Ia)

wherein each of $R^a$ and $R^b$ may be substituted with $X^a$, $X^b$, $L^a$, $L^b$ or Z;

Z denotes a halogen atom;

each of $L^a$ and $L^b$ denotes a halogen atom-substitutable leaving group;

"$n^{a1}+p^{a}$" denotes 0 or the number of hydrogen atoms substituted with $X^a$ or $L^a$ or Z among the hydrogen atoms in $R^a$;

"$n^{b1}+p^{b}$" denotes 0 or the number of hydrogen atoms substituted with $X^b$ or $L^b$ or Z among the hydrogen atoms in $R^b$;

"$p^a+p^b$" denotes 1 or more; when $n^{a1}$ denotes 2 or more then each $X^a$ may be same or different; when $n^{b1}$ denotes 2 or more then each $X^b$ may be same or different.

Furthermore, a method for producing the azole derivative according to the invention comprises a step for subjecting a carbonyl compound represented by Formula (V) to conversion into an oxirane thereby obtaining an oxirane derivative represented by Formula (III) which is then reacted with a compound represented by Formula (IV):

[Chem.7]

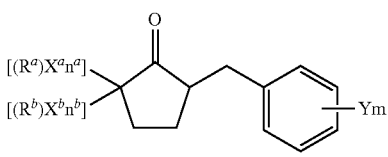

(V)

[Chem.8]

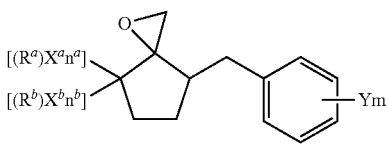

(III)

[Chem.9]

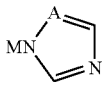

(IV)

wherein M denotes a hydrogen atom or an alkaline metal.

Furthermore, a method for producing the azole derivative according to the invention comprises a step for subjecting an oxetane compound represented by Formula (XVI) to ring opening using a halogenic acid.

[Chem. 10]

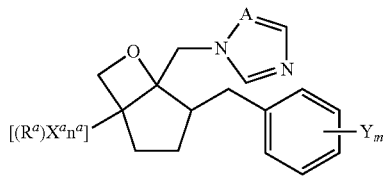

(XVI)

The invention further includes the following inventions as methods for producing intermediate compounds for the azole derivatives.

A method for producing an intermediate compound according to the invention comprises a step for reacting a 2-oxocyclopentane carboxylic acid ester derivative represented by Formula (XII) with formaldehyde or an equivalent thereof.

[Chem. 11]

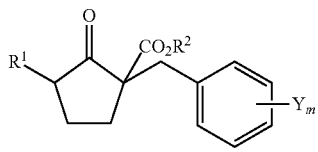

(XII)

Also, a method for producing an intermediate compound according to the invention comprises a step for subjecting a 2,2-bishydroxymethyl cyclopentanol derivative represented by Formula (XIX) to conversion into an oxetane ring while converting into a sulfone ester.

[Chem. 12]

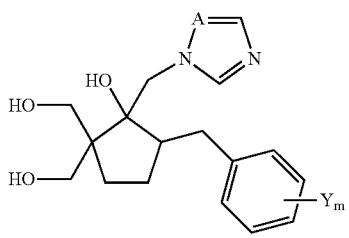

(XIX)

Also, a method for producing an intermediate compound for an azole derivative according to the invention comprises a step for reducing the sulfone ester of an oxetane sulfone ester derivative represented by Formula (XX) to obtain an intermediate compound represented by Formula (XXI).

[Chem. 13-A]

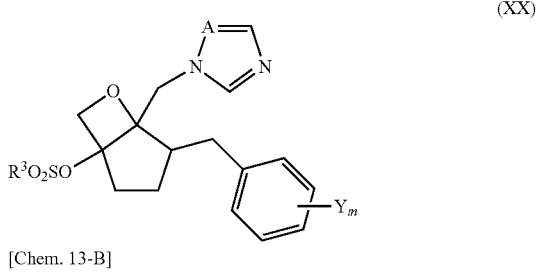

(XX)

[Chem. 13-B]

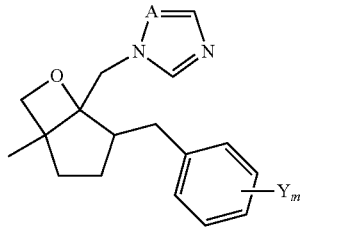

(XXI)

The invention also encompasses an agro-horticultural agent or an industrial material protecting agent containing as an active ingredient an azole derivative according to the invention.

In the specification and related matters, a symbol defining an identical functional group (or atom) in each formula is indicated as the identical symbol while omitting its detailed description. For example, an $R^a$ shown in Formula (I) and an $R^a$ shown in a different formula are identical. This understanding is not limited to $R^a$, and is applicable also to other functional groups (or atoms).

Advantageous Effects of Invention

An azole derivative according to the invention has an excellent biocidal effect on a large number of microorganisms which induce diseases in plants. Therefore, an agro-horticultural agent containing the azole derivative according to the invention as an active ingredient can advantageously exhibit a high controlling effect on a wide range of plant diseases.

Moreover, the agro-horticultural agent containing the azole derivative according to the invention as an active ingredient can advantageously regulate the growth of a variety of crops and horticultural plants thereby increasing their yields while improving their qualities.

On the other hand, an industrial material protecting agent containing the azole derivative according to the invention as an active ingredient can further advantageously protect an industrial material from a wide range of hazardous microorganisms which invade such materials.

DESCRIPTION OF EMBODIMENTS

The embodiments in the best mode for carrying out the invention are described below. These embodiments are just examples of the representative embodiments of the invention and do not serve to allow the scope of the invention to be interpreted narrowly. The descriptions are made in the orders shown below.

1. 2-(Halogenated hydrocarbon-substituted)-5-benzyl-1-azolylmethylcyclopentanol derivatives
    (1) $X^a$, $X^b$, $n^a$ and $n^b$
    (2) $(R^a)X^a n^a$ and $(R^b)X^b n^b$
    (3) Y and m
    (4) A
    (5) Stereoisomers
    (6) Typical examples
2. Methods for producing 2-(Halogenated hydrocarbon-substituted)-5-benzyl-1-azolylmethylcyclopentanol derivatives
    (1) Solvents
    (2) Bases and acids
    (3) First method for producing Compound (I)
    (3-1) Step 1A
    (3-2) Step 1B
    (3-3) Step 1C
    (3-3-1) Step 1C1
    (3-3-2) Step 1C2
    (3-3-3) Step 1C3
    (3-4) Step 1D
    (3-4-1) Step 1D1
    (3-4-2) Step 1D2
    (3-4-3) Step 1D3
    (4) Second method for producing Compound (I)
    (4-1) Step 2A
    (4-1-1) Step 2A1
    (4-1-2) Step 2A2
    (4-2) Step 2B
    (4-2-1) Step 2B1
    (4-2-2) Step 2B2
    (5) Third method for producing Compound (I)
    (5-1) Step 3A
    (5-1-1) Step 3A1
    (5-1-2) Step 3A2
    (6) Fourth method for producing Compound (I)
    (6-1) Step 4A
    (6-1-1) Step 4A1
    (6-1-2) Step 4A2
    (6-1-3) Step 4A3
    (6-1) Step 4B
    (6-2-1) Step 4B1
    (6-2-2) Step 4B2
    (6-2-3) Step 4B3
    (6-2) Step 4C
    (6-3-1) Step 4C1
    (6-3-2) Step 4C2
    (6-3-3) Step 4C3
3. Agro-horticultural agents and industrial material protecting agents
    (1) Plant disease controlling effects
    (2) Plant growth promoting effect
    (3) Industrial material protecting effect
    (4) Formulations

1. 2-(Halogenated hydrocarbon-substituted)-5-benzyl-1-azolylmethylcyclopentanol derivatives A 2-(halogenated hydrocarbon-substituted)-5-benzyl-1-azolylmethylcyclopentanol derivative represented by Formula (I) shown below according to the invention (hereinafter referred to as Compound (I)) is described below. Compound (I) has a hydrocarbon substituent bound to 2-position of the cyclopentane ring which is a halogen-substituted hydrocarbon substituent. Compound (I) is a novel compound which has not been described in any reference.

[Chem. 14]

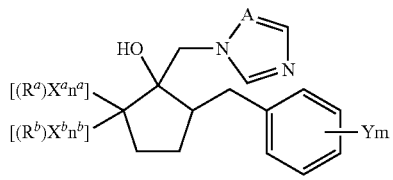

(I)

The typical examples of respective symbols ($R^a$, $R^b$, $X^a$, $X^b$, $n^a$, $n^b$, Y, m, and A) in Compound (I) and described below. The respective symbols in Formulas which denote other compounds ($R^{a1}$, $R^{a2}$, $R^{b1}$, $R^{b2}$, $X^{a1}$, $X^{a2}$, $X^{b1}$, $X^{b2}$, $n^{a1}$, $n^{a2}$, $n^{b1}$ and $n^{b2}$) have similar meanings as those indicated here ($R^a$, $R^b$, $X^a$, $X^b$, $n^a$ and $n^b$).

(1) $X^a$, $X^b$, $n^a$ and $n^b$

Each of $X^a$ and $X^b$ may for example be a halogen atom.
The halogen atom may for example be a fluorine atom, a chlorine atom, a bromine atom and an iodine atom. Among these, a fluorine atom, a chlorine atom and a bromine atom are preferred, with a chlorine atom being especially preferred.

$n^a$ denotes 0 or the number of $X^a$-substituted hydrogen atoms in $R^a$, $n^b$ denotes 0 or the number of $X^b$-substituted hydrogen atoms in $R^b$. $n^a$ and $n^b$ are preferably within the range of 0 to 5, more preferably 0 to 3, especially 0 to 1. Nevertheless, "$n^a+n^b$" is an integer of 1 or more. When $n^a$ is 2 or more, then each $X^a$ may be same or different. When $n^b$ is 2 or more, then each $X^b$ may be same or different.

(2) $(R^a)X^a n^a$ and $(R^b)X^b n^b$

First, when $n^a$ is 0, the following substituents may be exemplified as $R^a$.

Hydrogen atom; provided that $R^a$ and $R^b$ are not hydrogen atoms at the same time. When $R^a$ is a hydrogen atom, $R^a$ is not substituted with $X^a$. This understanding is not limited to $R^a$, and is applicable also to $R^b$.

$C_1$-$C_6$ Alkyl group: specifically, a methyl group, an ethyl group, a (1-methyl)ethyl group, a n-propyl group, a 1-methylpropyl group, 2-methylpropyl group, a n-butyl group, a 1-methylbutyl group, 2-methylbutyl group, a 1-ethylpropyl group and a 1,1-dimethylethyl group can be exemplified. Among these, a $C_1$-$C_4$ alkyl group is preferred, with $C_1$-$C_3$ alkyl group being especially preferred.

$C_2$-$C_6$ Alkenyl group: specifically, an ethenyl group, a 1,2-dimethylethenyl group, a 4-methyl-1,3-butadienyl group, a 1-propenyl group, a 2-propenyl group, a 2-methyl-2-propenyl group, a 3-methyl-2-propenyl group, a 2-butenyl group, a 3-butenyl group and 3-methyl-3-butenyl group can be exemplified. Among these, a $C_2$-$C_4$ alkenyl group is preferred.

$C_2$-$C_6$ Alkynyl group: specifically, an ethynyl group, a 1-propynyl group, a 2-propynyl group, a 1-butynyl group and a 2-butynyl group can be exemplified. Among these, a $C_2$-$C_4$ alkynyl group is preferred.

$(R^b)X^b n^b$ when $n^b$ is 0 is similar to $(R^a)X^a n^a$ when $n^a$ is 0.
When $n^a$ is 1 to 3, the following substituents can be exemplified as $(R^a)X^a n^a$.

$C_1$-$C_6$ Alkyl group: specifically, a halogen-substituted $C_1$-$C_6$ alkyl group, such as a chloromethyl group, a dichloromethyl group, a trichloromethyl group, a 2-chloroethyl group, a 1-chloroethyl group, a 2,2-dichloroethyl group, a 1,2-dichloroethyl group, a 2,2,2-trichloroethyl group, a 3-chloropropyl group, a 2,3-dichloropropyl group, a 1-chloro-1-methylethyl group, 2-chloro-1-methylethyl group, a 2-chloropropyl group, a 4-chlorobutyl group, a 5-chloropentyl group, a fluoromethyl group, a difluoromethyl group, a trifluoromethyl group, a 2-fluoroethyl group, a 1-fluoroethyl group, a 2,2-difluoroethyl group, a 1,2-difluoroethyl group, a 2,2,2-trifluoroethyl group, a 3-fluoropropyl group, a 2,3-difluoropropyl group, a 1-fluoro-1-methylethyl group, a 2-fluoro-1-methylethyl group, a 2-fluoropropyl group, a 3,3,3-trifluoropropyl group, a 2,2,3,3-tetrafluoropropyl group, a 2,2,3,3,3-pentafluoropropyl group, a 4-fluorobutyl group, a 5-fluoropentyl group, a bromomethyl group, a dibro-momethyl group, a tribromomethyl group, a 2-bromoethyl group, a 1-bromoethyl group, a 2,2-dibromoethyl group, a 1,2-dibromoethyl group, a 2,2,2-tribromoethyl group, a 3-bromopropyl group, a 2,3-dibromopropyl group, a 1-bromo-1-methylethyl group, a 2-bromo-1-methylethyl group, a 2-bromopropyl group, a 4-bromobutyl group, a 5-bromopentyl group, a iodomethyl group, a diiodomethyl group, a 2-iodoethyl group, a 1-iodoethyl group, a 2,2-diiodoethyl group, a 1,2-diiodoethyl group, a 2,2,2-triiodoethyl group, a 3-iodopropyl group, a 2,3-diiodopropyl group, a 1-iodo-1-methylethyl group, a 2-iodo-1-methylethyl group, a 2-iodopropyl group, a 4-iodobutyl group and the like can be exemplified. Among these, a $C_1$-$C_4$ alkyl group is preferred, with a $C_1$-$C_3$ alkyl group being especially preferred.

$C_2$-$C_6$ Alkenyl group: specifically, a halogen-substituted $C_2$-$C_6$ alkenyl group, such as a 2-chloroethenyl group, a 2,2-dichloroethenyl group, a 2-chloro-2-propenyl group, a 3,3-dichloro-2-propenyl group, a 2,3-dichloro-2-propenyl group, a 3,3-dichloro-2-methyl-2-propenyl group, a 3-chloro-2-butenyl group, a 2-fluoroethenyl group, a 2,2-difluoroethenyl group, a 2-fluoro-2-propenyl group, a 3,3-difluoro-2-propenyl group, a 2,3-difluoro-2-propenyl group, a 3,3-difluoro-2-methyl-2-propenyl group, a 3-fluoro-2-butenyl group, a 2-bromoethenyl group, a 2,2-dibromoethenyl group, a 2-bromo-2-propenyl group, a 3,3-dibromo-2-propenyl group, a 2,3-dibromo-2-propenyl group, a 3,3-dibromo-2-methyl-2-propenyl group, a 3-bromo-2-butenyl group, a 2-iodoethenyl group, a 2,2-diiodoethenyl group, a 2-iodo-2-propenyl group, a 3,3-diiodo-2-propenyl group, a 2,3-diiodo-2-propenyl group and the like can be exemplified. Among these, a $C_2$-$C_4$ alkenyl group is preferred.

$C_2$-$C_6$ Alkynyl group: specifically, a halogen-substituted $C_2$-$C_6$ alkynyl group, such as a 2-fluoroethynyl group, a 2-chloroethynyl group, a 3-fluoro-2-propynyl group, a 3-chloro-2-propynyl group, a 3-bromo-2-propynyl group and the like can be exemplified. Among these, a $C_2$-$C_4$ alkynyl group is preferred.

$(R^b)X^bn^b$ when $n^b$ is 1 to 3 is similar to $(R^a)X^an^a$ when $n^a$ is 1 to 3.

(3) Y and m

The following substituents can be exemplified as Y.

Halogen atom: specifically, a chlorine atom, a fluorine atom, a bromine atom and an iodine atom can be exemplified.

$C_1$-$C_4$ Alkyl group: specifically, a methyl group, an ethyl group, a n-propyl group, a 1-methylethyl group, 2-methylpropyl group, a n-butyl group, a 1,1-dimethylethyl group and the like can be exemplified.

$C_1$-$C_4$ Haloalkyl group: specifically, a trifluoromethyl group, a 1,1,2,2,2-pentafluoroethyl group, a chloromethyl group, a trichloromethyl group, a bromomethyl group and the like can be exemplified.

$C_1$-$C_4$ Alkoxy group: specifically, a methoxy group, an ethoxy group, a n-propoxy group and the like can be exemplified.

$C_1$-$C_4$ Haloalkoxy group: specifically, a trifluoromethoxy group, a difluoromethoxy group, a 1,1,2,2,2-pentafluoroethoxy group, a 2,2,2-trifluoroethoxy group and the like can be exemplified.

Y may also be a phenyl group, a cyano group or a nitro group.

Y is preferably a halogen atom, a $C_1$-$C_3$ haloalkyl group, a $C_1$-$C_3$ haloalkoxy group, a $C_1$-$C_3$ alkyl group and a $C_1$-$C_3$ alkoxy group, with a halogen atom, a $C_1$-$C_2$ haloalkyl group and a $C_1$-$C_2$ haloalkoxy group being especially preferred.

m denotes an integer of 0 to 5. When m is 2 or more, each Y may be same or different. m is preferably 0 to 3, and more preferably 0 to 2.

(4) A

A nitrogen atom or a methyne group can be exemplified as A. More preferably, A is a nitrogen atom.

(5) Stereoisomers

Compound (I) exists as a stereoisomer represented by Formula (I-C) or (I-T) (type C or type T). Compound (I) may be either one of the isomers, or a mixture thereof. In Formula shown below, the relative steric configuration of a cis type between the hydroxyl group in 1-position and the benzyl group in 5-position is referred to as (I-C), while the relative steric configuration of a trans type is referred to as (I-T).

[Chem. 15]

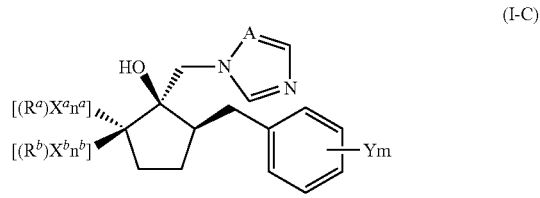

(I-C)

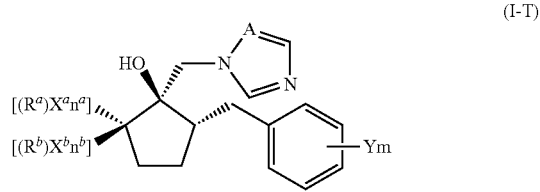

(I-T)

(6) Typical Examples

Depending on the combination of $(R^a)X^an^a$, $(R^b)X^bn^b$, Ym, A and isomers described above, the compounds indicated in Table 1 to Table 13 shown below can be exemplified as Compounds (I).

Each table can be understood as described below.

1) Columns of $(R^a)X^an^a$ $(R^a)X^an^a$ is indicated as a single substituent. Unless $R^a$ is a hydrogen atom, it should be understood that the hydrogen atom-deficient carbon atom on the left end of $(R^a)X^an^a$ serves to the binding to the cyclopentane ring in Compound (I). A case having no halogen atom in $(R^a)X^an^a$ here means $n^a=0$.

2) Columns of $(R^b)X^bn^b$ $(R^b)X^bn^b$ is indicated as a single substituent. Unless $R^b$ is a hydrogen atom, it should be understood that the hydrogen atom-deficient carbon atom on the left end of $(R^b)X^bn^b$ serves to the binding to the cyclopentane ring in Compound (I). A case having no halogen atom in the substituent here means $n^b=0$.

3) Columns of Ym

"-(hyphen)" indicates a non-substitution (m=0). The number before "-" indicates the binding position when regarding the carbon atom binding to the carbon atom binding to the cyclopentane ring as being in 1-position in the case having a substituent on a phenyl ring.

TABLE 1

| Compound No. | $(R^a)X^an^{a1)}$ | $(R^b)X^bn^{b2)}$ | $Ym^{3)}$ | A | Type |
|---|---|---|---|---|---|
| I-1 | $CH_3$ | $CH_2Cl$ | 4-Cl | N | C |
| I-2 | $CH_3$ | $CHCl_2$ | 4-Cl | N | C |
| I-3 | $CH_3$ | $CCl_3$ | 4-Cl | N | C |
| I-4 | $CH_3$ | $CH_2CH_2Cl$ | 4-Cl | N | C |
| I-5 | $CH_3$ | $CHClCH_3$ | 4-Cl | N | C |
| I-6 | $CH_3$ | $CH_2CHCl_2$ | 4-Cl | N | C |
| I-7 | $CH_3$ | $CHClCH_2Cl$ | 4-Cl | N | C |
| I-8 | $CH_3$ | $CH_2CCl_3$ | 4-Cl | N | C |
| I-9 | $CH_3$ | $CH_2CH_2CH_2Cl$ | 4-Cl | N | C |
| I-10 | $CH_3$ | $CH_2CHClCH_2Cl$ | 4-Cl | N | C |
| I-11 | $CH_3$ | $CCl(CH_3)CH_3$ | 4-Cl | N | C |
| I-12 | $CH_3$ | $CH(CH_2Cl)CH_3$ | 4-Cl | N | C |
| I-13 | $CH_3$ | $CH_2CH_2CH_2CH_2Cl$ | 4-Cl | N | C |
| I-14 | $CH_3$ | $CH=CCl_2$ | 4-Cl | N | C |
| I-15 | $CH_3$ | $CH_2CCl=CH_2$ | 4-Cl | N | C |
| I-16 | $CH_3$ | $CH_2CH=CCl_2$ | 4-Cl | N | C |
| I-17 | $CH_3$ | $CH_2CCl=CHCl$ | 4-Cl | N | C |
| I-18 | $CH_3$ | $CH_2CH=C(Cl)CH_3$ | 4-Cl | N | C |
| I-19 | $CH_3$ | $C\equiv CCl$ | 4-Cl | N | C |
| I-20 | $CH_3$ | $CH_2F$ | 4-Cl | N | C |
| I-21 | $CH_3$ | $CF_3$ | 4-Cl | N | C |
| I-22 | $CH_3$ | $CH_2CH_2F$ | 4-Cl | N | C |
| I-23 | $CH_3$ | $CH_2CF_3$ | 4-Cl | N | C |
| I-24 | $CH_3$ | $CH=CF_2$ | 4-Cl | N | C |
| I-25 | $CH_3$ | $CH_2Br$ | 4-Cl | N | C |
| I-26 | $CH_3$ | $CH_2CH_2Br$ | 4-Cl | N | C |
| I-27 | $CH_3$ | $CHBrCH_3$ | 4-Cl | N | C |
| I-28 | $CH_3$ | $CH_2CHCl_2$ | 4-Cl | N | C |
| I-29 | $CH_3$ | $CHBrCH_2Br$ | 4-Cl | N | C |
| I-30 | $CH_3$ | $CH_2CHBrCH_2Br$ | 4-Cl | N | C |
| I-31 | $CH_3$ | $CBr(CH_3)CH_3$ | 4-Cl | N | C |
| I-32 | $CH_3$ | $CH(CH_2Br)CH_3$ | 4-Cl | N | C |
| I-33 | $CH_3$ | $CH_2CBr=CH_2$ | 4-Cl | N | C |
| I-34 | $CH_3$ | $CH_2C\equiv CBr$ | 4-Cl | N | C |
| I-35 | $CH_3$ | $CH_2I$ | 4-Cl | N | C |
| I-36 | $CH_2CH_3$ | $CH_2Cl$ | 4-Cl | N | C |
| I-37 | $CH_2CH_3$ | $CH_2CH_2Cl$ | 4-Cl | N | C |
| I-38 | $CH_2CH_3$ | $CHClCH_2Cl$ | 4-Cl | N | C |
| I-39 | $CH_2CH_3$ | $CH_2CH_2CH_2Cl$ | 4-Cl | N | C |
| I-40 | $CH_2CH_3$ | $CCl(CH_3)CH_3$ | 4-Cl | N | C |
| I-41 | $CH_2CH_3$ | $CH(CH_2Cl)CH_3$ | 4-Cl | N | C |
| I-42 | $CH_2CH_3$ | $CH=CCl_2$ | 4-Cl | N | C |
| I-43 | $CH_2CH_3$ | $CH_2CCl=CH_2$ | 4-Cl | N | C |
| I-44 | $CH_2CH_3$ | $CH_2CH=CCl_2$ | 4-Cl | N | C |
| I-45 | $CH_2CH_3$ | $CH_2F$ | 4-Cl | N | C |
| I-46 | $CH_2CH_3$ | $CF_3$ | 4-Cl | N | C |
| I-47 | $CH_2CH_3$ | $CH_2CH_2F$ | 4-Cl | N | C |
| I-48 | $CH_2CH_3$ | $CF(CH_3)CH_3$ | 4-Cl | N | C |
| I-49 | $CH_2CH_3$ | $CH_2Br$ | 4-Cl | N | C |

TABLE 2

| Compound No. | $(R^a)X^an^{a1)}$ | $(R^b)X^bn^{b2)}$ | $Ym^{3)}$ | A | Type |
|---|---|---|---|---|---|
| I-50 | $CH_2CH_3$ | $CHBrCH_2Br$ | 4-Cl | N | C |
| I-51 | $CH_2CH_3$ | $CBr(CH_3)CH_3$ | 4-Cl | N | C |
| I-52 | $CH_2CH_3$ | $CH=CBr_2$ | 4-Cl | N | C |
| I-53 | $CH_2CH_3$ | $CH_2CBr=CH_2$ | 4-Cl | N | C |
| I-54 | $CH_2CH_3$ | $CH_2I$ | 4-Cl | N | C |
| I-55 | H | $CH_2Cl$ | 4-Cl | N | C |
| I-56 | H | $CH_2CH_2Cl$ | 4-Cl | N | C |
| I-57 | H | $CHClCH_2Cl$ | 4-Cl | N | C |
| I-58 | H | $CH_2CH_2CH_2Cl$ | 4-Cl | N | C |
| I-59 | H | $CCl(CH_3)CH_3$ | 4-Cl | N | C |
| I-60 | H | $CH(CH_2Cl)CH_3$ | 4-Cl | N | C |
| I-61 | H | $CH=CCl_2$ | 4-Cl | N | C |
| I-62 | H | $CH_2CCl=CH_2$ | 4-Cl | N | C |
| I-63 | H | $CH_2CH=CCl_2$ | 4-Cl | N | C |
| I-64 | H | $CH_2F$ | 4-Cl | N | C |
| I-65 | H | $CF_3$ | 4-Cl | N | C |
| I-66 | H | $CH_2CH_2F$ | 4-Cl | N | C |
| I-67 | H | $CF(CH_3)CH_3$ | 4-Cl | N | C |
| I-68 | H | $CH_2Br$ | 4-Cl | N | C |
| I-69 | H | $CHBrCH_2Br$ | 4-Cl | N | C |
| I-70 | H | $CBr(CH_3)CH_3$ | 4-Cl | N | C |
| I-71 | H | $CH=CBr_2$ | 4-Cl | N | C |
| I-72 | H | $CH_2CBr=CH_2$ | 4-Cl | N | C |
| I-73 | $CH_3$ | $CH_2Cl$ | — | N | C |
| I-74 | $CH_3$ | $CH_2Cl$ | 3-Cl | N | C |
| I-75 | $CH_3$ | $CH_2Cl$ | 3,4-$Cl_2$ | N | C |
| I-76 | $CH_3$ | $CH_2Cl$ | 4-Br | N | C |
| I-77 | $CH_3$ | $CH_2Cl$ | 4-F | N | C |
| I-78 | $CH_3$ | $CH_2Cl$ | 4-$CF_3$ | N | C |
| I-79 | $CH_3$ | $CH_2Cl$ | 4-$OCF_3$ | N | C |
| I-80 | $CH_3$ | $CH_2Cl$ | 4-Me | N | C |
| I-81 | $CH_3$ | $CH_2Cl$ | 4-OMe | N | C |
| I-82 | $CH_3$ | $CH_2Cl$ | 4-Ph | N | C |
| I-83 | $CH_3$ | $CH_2Cl$ | 4-CN | N | C |
| I-84 | $CH_3$ | $CH_2Cl$ | 4-$NO_2$ | N | C |
| I-85 | $CH_3$ | $CH_2Cl$ | 2-Cl | N | C |
| I-86 | $CH_3$ | $CH_2Cl$ | 2-F | N | C |
| I-87 | $CH_3$ | $CH_2Cl$ | 2,4-$Cl_2$ | N | C |
| I-88 | $CH_3$ | $CH_2Cl$ | 2,4-$F_2$ | N | C |
| I-89 | $CH_3$ | $CH_2Cl$ | 3-F,4-Cl | N | C |
| I-90 | $CH_3$ | $CH_2Cl$ | 2-F,4-Cl | N | C |
| I-91 | $CH_2CH_3$ | $CH_2Cl$ | 4-F | N | C |
| I-92 | $CH_2CH_3$ | $CH_2Cl$ | 4-$CF_3$ | N | C |
| I-93 | $CH_2CH_3$ | $CH_2Cl$ | 4-$OCF_3$ | N | C |
| I-94 | $CH_2CH_3$ | $CH_2Cl$ | 4-Me | N | C |
| I-95 | $CH_2CH_3$ | $CH_2Cl$ | 4-OMe | N | C |
| I-96 | $CH_2CH_3$ | $CH_2Cl$ | 4-Ph | N | C |
| I-97 | $CH_2CH_3$ | $CH_2Cl$ | — | N | C |
| I-98 | $CH_2CH_3$ | $CH_2Cl$ | 2,4-$F_2$ | N | C |

TABLE 3

| Compound No. | $(R^a)X^an^{a1)}$ | $(R^b)X^bn^{b2)}$ | $Ym^{3)}$ | A | Type |
|---|---|---|---|---|---|
| I-101 | $CH_2Cl$ | $CH_3$ | 4-Cl | N | C |
| I-102 | $CHCl_2$ | $CH_3$ | 4-Cl | N | C |
| I-103 | $CCl_3$ | $CH_3$ | 4-Cl | N | C |
| I-104 | $CH_2CH_2Cl$ | $CH_3$ | 4-Cl | N | C |
| I-105 | $CHClCH_3$ | $CH_3$ | 4-Cl | N | C |
| I-106 | $CH_2CHCl_2$ | $CH_3$ | 4-Cl | N | C |
| I-107 | $CHClCH_2Cl$ | $CH_3$ | 4-Cl | N | C |
| I-108 | $CH_2CCl_3$ | $CH_3$ | 4-Cl | N | C |
| I-109 | $CH_2CH_2CH_2Cl$ | $CH_3$ | 4-Cl | N | C |
| I-110 | $CH_2CHClCH_2Cl$ | $CH_3$ | 4-Cl | N | C |
| I-111 | $CCl(CH_3)CH_3$ | $CH_3$ | 4-Cl | N | C |
| I-112 | $CH(CH_2Cl)CH_3$ | $CH_3$ | 4-Cl | N | C |
| I-113 | $CH_2CH_2CH_2CH_2Cl$ | $CH_3$ | 4-Cl | N | C |
| I-114 | $CH=CCl_2$ | $CH_3$ | 4-Cl | N | C |
| I-115 | $CH_2CCl=CH_2$ | $CH_3$ | 4-Cl | N | C |
| I-116 | $CH_2CH=CCl_2$ | $CH_3$ | 4-Cl | N | C |
| I-117 | $CH_2CCl=CHCl$ | $CH_3$ | 4-Cl | N | C |
| I-118 | $CH_2CH=C(Cl)CH_3$ | $CH_3$ | 4-Cl | N | C |
| I-119 | $C\equiv CHCl$ | $CH_3$ | 4-Cl | N | C |
| I-120 | $CH_2F$ | $CH_3$ | 4-Cl | N | C |
| I-121 | $CF_3$ | $CH_3$ | 4-Cl | N | C |

TABLE 3-continued

| Compound No. | $(R^a)X^a n^{a1)}$ | $(R^b)X^b n^{b2)}$ | $Ym^{3)}$ | A | Type |
|---|---|---|---|---|---|
| I-122 | CH₂CH₂F | CH₃ | 4-Cl | N | C |
| I-123 | CH₂CF₃ | CH₃ | 4-Cl | N | C |
| I-124 | CH=CF₂ | CH₃ | 4-Cl | N | C |
| I-125 | CH₂Br | CH₃ | 4-Cl | N | C |
| I-126 | CH₂CH₂Br | CH₃ | 4-Cl | N | C |
| I-127 | CHBrCH₃ | CH₃ | 4-Cl | N | C |
| I-128 | CH₂CHCl₂ | CH₃ | 4-Cl | N | C |
| I-129 | CHBrCH₂Br | CH₃ | 4-Cl | N | C |
| I-130 | CH₂CHBrCH₂Br | CH₃ | 4-Cl | N | C |
| I-131 | CBr(CH₃)CH₃ | CH₃ | 4-Cl | N | C |
| I-132 | CH(CH₂Br)CH₃ | CH₃ | 4-Cl | N | C |
| I-133 | CH₂CBr=CH₂ | CH₃ | 4-Cl | N | C |
| I-134 | CH₂C=CHBr | CH₃ | 4-Cl | N | C |
| I-135 | CH₂I | CH₃ | 4-Cl | N | C |
| I-136 | CH₂Cl | CH₂CH₃ | 4-Cl | N | C |
| I-137 | CH₂CH₂Cl | CH₂CH₃ | 4-Cl | N | C |
| I-138 | CHClCH₂Cl | CH₂CH₃ | 4-Cl | N | C |
| I-139 | CH₂CH₂CH₂Cl | CH₂CH₃ | 4-Cl | N | C |
| I-140 | CCl(CH₃)CH₃ | CH₂CH₃ | 4-Cl | N | C |
| I-141 | CH(CH₂Cl)CH₃ | CH₂CH₃ | 4-Cl | N | C |
| I-142 | CH=CCl₂ | CH₂CH₃ | 4-Cl | N | C |
| I-143 | CH₂CCl=CH₂ | CH₂CH₃ | 4-Cl | N | C |
| I-144 | CH₂CH=CCl₂ | CH₂CH₃ | 4-Cl | N | C |
| I-145 | CH₂F | CH₂CH₃ | 4-Cl | N | C |
| I-146 | CF₃ | CH₂CH₃ | 4-Cl | N | C |
| I-147 | CH₂CH₂F | CH₂CH₃ | 4-Cl | N | C |
| I-148 | CF(CH₃)CH₃ | CH₂CH₃ | 4-Cl | N | C |
| I-149 | CH₂Br | CH₂CH₃ | 4-Cl | N | C |

TABLE 4

| Compound No. | $(R^a)X^a n^{a1)}$ | $(R^b)X^b n^{b2)}$ | $Ym^{3)}$ | A | Type |
|---|---|---|---|---|---|
| I-150 | CHBrCH₂Br | CH₂CH₃ | 4-Cl | N | C |
| I-151 | CBr(CH₃)CH₃ | CH₂CH₃ | 4-Cl | N | C |
| I-152 | CH=CBr₂ | CH₂CH₃ | 4-Cl | N | C |
| I-153 | CH₂CBr=CH₂ | CH₂CH₃ | 4-Cl | N | C |
| I-154 | CH₂I | CH₂CH₃ | 4-Cl | N | C |
| I-155 | CH₂Cl | H | 4-Cl | N | C |
| I-156 | CH₂CH₂Cl | H | 4-Cl | N | C |
| I-157 | CHClCH₂Cl | H | 4-Cl | N | C |
| I-158 | CH₂CH₂CH₂Cl | H | 4-Cl | N | C |
| I-159 | CCl(CH₃)CH₃ | H | 4-Cl | N | C |
| I-160 | CH(CH₂Cl)CH₃ | H | 4-Cl | N | C |
| I-161 | CH=CCl₂ | H | 4-Cl | N | C |
| I-162 | CH₂CCl=CH₂ | H | 4-Cl | N | C |
| I-163 | CH₂CH=CCl₂ | H | 4-Cl | N | C |
| I-164 | CH₂F | H | 4-Cl | N | C |
| I-165 | CF₃ | H | 4-Cl | N | C |
| I-166 | CH₂CH₂F | H | 4-Cl | N | C |
| I-167 | CF(CH₃)CH₃ | H | 4-Cl | N | C |
| I-168 | CH₂Br | H | 4-Cl | N | C |
| I-169 | CHBrCH₂Br | H | 4-Cl | N | C |
| I-170 | CBr(CH₃)CH₃ | H | 4-Cl | N | C |
| I-171 | CH=CBr₂ | H | 4-Cl | N | C |
| I-172 | CH₂CBr=CH₂ | H | 4-Cl | N | C |
| I-173 | CH₂Cl | CH₃ | — | N | C |
| I-174 | CH₂Cl | CH₃ | 3-Cl | N | C |
| I-175 | CH₂Cl | CH₃ | 3,4-Cl₂ | N | C |
| I-176 | CH₂Cl | CH₃ | 4-Br | N | C |
| I-177 | CH₂Cl | CH₃ | 4-F | N | C |
| I-178 | CH₂Cl | CH₃ | 4-CF₃ | N | C |
| I-179 | CH₂Cl | CH₃ | 4-OCF₃ | N | C |
| I-180 | CH₂Cl | CH₃ | 4-Me | N | C |
| I-181 | CH₂Cl | CH₃ | 4-OMe | N | C |
| I-182 | CH₂Cl | CH₃ | 4-Ph | N | C |
| I-183 | CH₂Cl | CH₃ | 4-CN | N | C |
| I-184 | CH₂Cl | CH₃ | 4-NO₂ | N | C |
| I-185 | CH₂Cl | CH₃ | 2-Cl | N | C |
| I-186 | CH₂Cl | CH₃ | 2-F | N | C |
| I-187 | CH₂Cl | CH₃ | 2,4-Cl₂ | N | C |
| I-188 | CH₂Cl | CH₃ | 2,4-F₂ | N | C |
| I-189 | CH₂Cl | CH₃ | 3-F,4-Cl | N | C |
| I-190 | CH₂Cl | CH₃ | 2-F,4-Cl | N | C |
| I-191 | CH₂Cl | CH₂CH₃ | 4-F | N | C |

TABLE 4-continued

| Compound No. | $(R^a)X^a n^{a1)}$ | $(R^b)X^b n^{b2)}$ | $Ym^{3)}$ | A | Type |
|---|---|---|---|---|---|
| I-192 | CH₂Cl | CH₂CH₃ | 4-CF₃ | N | C |
| I-193 | CH₂Cl | CH₂CH₃ | 4-OCF₃ | N | C |
| I-194 | CH₂Cl | CH₂CH₃ | 4-Me | N | C |
| I-195 | CH₂Cl | CH₂CH₃ | 4-OMe | N | C |
| I-196 | CH₂Cl | CH₂CH₃ | 4-Ph | N | C |
| I-197 | CH₂Cl | CH₂CH₃ | — | N | C |
| I-198 | CH₂Cl | CH₂CH₃ | 2,4-F₂ | N | C |

TABLE 5

| Compound No. | $(R^a)X^a n^{a1)}$ | $(R^b)X^b n^{b2)}$ | $Ym^{3)}$ | A | Type |
|---|---|---|---|---|---|
| I-201 | CH(CH₃)CH₃ | CH₂Cl | 4-Cl | N | C |
| I-202 | CH₂CH₂CH₃ | CH₂Cl | 4-Cl | N | C |
| I-203 | CH₂Cl | CH₂Cl | 4-Cl | N | C |
| I-204 | CH₂CH₂Cl | CH₂Cl | 4-Cl | N | C |
| I-205 | CH(CH₃)CH₃ | CH₂CH₂Cl | 4-Cl | N | C |
| I-206 | CH₂CH₂CH₂CH₃ | CH₂CH₂Cl | 4-Cl | N | C |
| I-207 | CH₂Cl | CH₂CH₂Cl | 4-Cl | N | C |
| I-208 | CH₂CH₂Cl | CH₂CH₂Cl | 4-Cl | N | C |
| I-209 | CH(CH₃)CH₃ | CH=CCl₂ | 4-Cl | N | C |
| I-210 | CH₂CH₂CH₃ | CH=CCl₂ | 4-Cl | N | C |
| I-211 | CH(CH₃)CH₃ | CH₂CCl=CH₂ | 4-Cl | N | C |
| I-212 | CH₂CH₂CH₃ | CH₂CCl=CH₂ | 4-Cl | N | C |
| I-213 | CH(CH₃)CH₃ | CF₃ | 4-Cl | N | C |
| I-214 | CH₂CH₂CH₃ | CF₃ | 4-Cl | N | C |
| I-215 | CH(CH₃)CH₃ | CH₂CF₃ | 4-Cl | N | C |
| I-216 | CH₂CH₂CH₃ | CH₂CF₃ | 4-Cl | N | C |
| I-217 | CH₂CF₃ | CH₂CF₃ | 4-Cl | N | C |
| I-218 | CH₂CH₂CH₃ | CH₂Br | 4-Cl | N | C |
| I-219 | CH(CH₃)CH₃ | CH₂Br | 4-Cl | N | C |
| I-220 | CH₂CH₂CH₃ | CH₂I | 4-Cl | N | C |
| I-221 | CH(CH₃)CH₃ | CH₂I | 4-Cl | N | C |
| I-222 | CH₂Cl | CH(CH₃)CH₃ | 3-Cl | N | C |
| I-223 | CH₂Cl | CH₂CH₂CH₃ | 2-Cl | N | C |
| I-224 | CH₂Cl | CH₂Cl | 3,4-Cl₂ | N | C |
| I-225 | CH₂Cl | CH₂CH₂Cl | 4-F | N | C |
| I-226 | CH₂CH₂Cl | CH(CH₃)CH₃ | 3-F | N | C |
| I-227 | CH₂CH₂Cl | CH₂CH₂CH₂CH₃ | 4-CF₃ | N | C |
| I-228 | CH₂CH₂Cl | CH₂Cl | 4-OCF₃ | N | C |
| I-229 | CH₂CH₂Cl | CH₂CH₂Cl | 4-Ph | N | C |
| I-230 | CH=CCl₂ | CH(CH₃)CH₃ | 4-Me | N | C |
| I-231 | CH=CCl₂ | CH₂CH₂CH₃ | — | N | C |
| I-232 | CH₂CCl=CH₂ | CH(CH₃)CH₃ | 4-Br | N | C |
| I-233 | CH₂CCl=CH₂ | CH₂CH₂CH₃ | 4-Cl | N | C |
| I-234 | CF₃ | CH(CH₃)CH₃ | 4-Cl | N | C |
| I-235 | CF₃ | CHCH₂CH₃ | 4-Cl | N | C |
| I-236 | CH₂CF₃ | CH(CH₃)CH₃ | 4-Cl | N | C |
| I-237 | CH₂CF₃ | CH₂CH₂CH₃ | 4-Cl | N | C |
| I-238 | CH₂CF₃ | CH₂CF₃ | 4-Cl | N | C |
| I-239 | CH₂Br | CH₂CH₂CH₃ | 4-Cl | N | C |
| I-240 | CH₂Br | CH(CH₃)CH₃ | 4-Cl | N | C |
| I-241 | CH₂I | CH₂CH₂CH₃ | 4-Cl | N | C |
| I-242 | CH₂I | CH(CH₃)CH₃ | 4-Cl | N | C |
| I-243 | CH₂Cl | CH₃ | 4-Cl | CH | C |
| I-244 | CH₃ | CH₂Cl | 4-Cl | CH | C |
| I-245 | CH₂CH₃ | CH₂Cl | 4-Cl | CH | C |
| I-246 | CH(CH₃)CH₃ | CH₂Cl | 4-Cl | CH | C |
| I-247 | CH₂CH₂CH₃ | CH₂Cl | 4-Cl | CH | C |
| I-248 | CH₂Cl | CH₂Cl | 4-Cl | CH | C |
| I-249 | CH₂CH₂Cl | CH₂Cl | 4-Cl | CH | C |
| I-250 | CH(CH₃)CH₃ | CH₂Cl | 4-Cl | CH | C |

TABLE 6

| Compound No. | $(R^b)X^a n^{a1)}$ | $(R^b)X^b n^{b2)}$ | $Ym^{3)}$ | A | Type |
|---|---|---|---|---|---|
| I-251 | CH₂CH₂CH₂CH₃ | CH₂Cl | 4-Cl | CH | C |
| I-252 | CH=CCl₂ | CH₂Cl | 4-Cl | CH | C |
| I-253 | CH₂CCl=CH₂ | CH₂Cl | 4-Cl | CH | C |
| I-254 | CF₃ | CH₂Cl | 3-Cl | CH | C |

TABLE 6-continued

| Compound No. | $(R^a)X^a n^{a1)}$ | $(R^b)X^b n^{b2)}$ | $Y m^{3)}$ | A | Type |
|---|---|---|---|---|---|
| I-255 | CH$_2$CF$_3$ | CH$_2$Cl | 2-Cl | CH | C |
| I-256 | CH$_2$Br | CH$_2$Cl | 3,4-Cl$_2$ | CH | C |
| I-257 | CH$_3$ | CH$_2$CH$_2$Cl | 4-F | CH | C |
| I-258 | CH$_2$CH$_3$ | CH$_2$CH$_2$Cl | 3-F | CH | C |
| I-259 | CH(CH$_3$)CH$_3$ | CH$_2$CH$_2$Cl | 4-CF$_3$ | CH | C |
| I-260 | CH$_2$CH$_2$CH$_3$ | CH$_2$CH$_2$Cl | 4-OCF$_3$ | CH | C |
| I-261 | CH$_2$Cl | CH$_3$ | 4-Ph | CH | C |
| I-262 | CH$_2$Cl | CH$_2$CH$_3$ | 4-Me | CH | C |
| I-263 | CH$_2$Cl | CH(CH$_3$)CH$_3$ | 3-Br | CH | C |
| I-264 | CH$_2$Cl | CH$_2$CH$_2$CH$_3$ | 4-Br | CH | C |
| I-265 | CH$_2$F | CH$_2$F | 4-Cl | CH | C |
| I-266 | CH$_2$Cl | CH$_2$CH$_2$Cl | 4-Cl | CH | C |
| I-267 | CH$_2$Cl | CH(CH$_3$)CH$_3$ | 4-Cl | CH | C |
| I-268 | CH$_2$Cl | CH$_2$CH$_2$CH$_3$ | 4-Cl | CH | C |
| I-269 | CH$_2$Cl | CH=CCl$_2$ | 4-Cl | CH | C |
| I-270 | CH$_2$Cl | CH$_2$CCl=CH$_2$ | 4-Cl | CH | C |
| I-271 | CH$_2$Cl | CF$_3$ | 4-Cl | CH | C |
| I-272 | CH$_2$Cl | CH$_2$CF$_3$ | 4-Cl | CH | C |
| I-273 | CH$_2$Cl | CH$_2$Br | 4-Cl | CH | C |
| I-274 | CH$_2$CH$_2$Cl | CH$_3$ | 4-Cl | CH | C |
| I-275 | CH$_2$CH$_2$Cl | CH$_2$CH$_3$ | 4-Cl | CH | C |
| I-276 | CH$_2$CH$_2$Cl | CH(CH$_3$)CH$_3$ | 4-Cl | CH | C |
| I-277 | CH$_2$CH$_2$Cl | CH$_2$CH$_2$CH$_3$ | 4-Cl | CH | C |
| I-278 | CH$_3$ | CH$_2$Cl | 3-Cl | CH | C |
| I-279 | CH$_3$ | CH$_2$Cl | 2-Cl | CH | C |
| I-280 | CH$_3$ | CH$_2$Cl | 4-F | CH | C |
| I-281 | CH$_3$ | CH$_2$Cl | 3-F | CH | C |
| I-282 | CH$_3$ | CH$_2$Cl | 2-F | CH | C |
| I-283 | CH$_3$ | CH$_2$Cl | 4-OCF$_3$ | CH | C |
| I-284 | CH$_3$ | CH$_2$Cl | 4-CF$_3$ | CH | C |
| I-285 | CH$_3$ | CH$_2$Cl | 2,4-Cl$_2$ | CH | C |
| I-286 | CH$_3$ | CH$_2$Cl | 2,4-F$_2$ | CH | C |
| I-287 | CH$_3$ | CH$_2$Cl | 4-Ph | CH | C |
| I-288 | CH$_3$ | CH$_2$Cl | 4-Br | CH | C |
| I-289 | CH$_2$Cl | CH$_3$ | 3-Cl | CH | C |
| I-290 | CH$_2$Cl | CH$_3$ | 2-Cl | CH | C |
| I-291 | CH$_2$Cl | CH$_3$ | 4-F | CH | C |
| I-292 | CH$_2$Cl | CH$_3$ | 3-F | CH | C |
| I-293 | CH$_2$Cl | CH$_3$ | 2-F | CH | C |
| I-294 | CH$_2$Cl | CH$_3$ | 4-OCF$_3$ | CH | C |
| I-295 | CH$_2$Cl | CH$_3$ | 4-CF$_3$ | CH | C |
| I-296 | CH$_2$Cl | CH$_3$ | 2,4-Cl$_2$ | CH | C |
| I-297 | CH$_2$Cl | CH$_3$ | 2,4-F$_2$ | CH | C |
| I-298 | CH$_2$Cl | CH$_3$ | 4-Ph | CH | C |
| I-299 | CH$_2$Cl | CH$_3$ | 4-Br | CH | C |

TABLE 7

| Compound No. | $(R^a)X^a n^{a1)}$ | $(R^b)X^b n^{b2)}$ | $Y m^{3)}$ | A | Type |
|---|---|---|---|---|---|
| I-301 | CH$_3$ | CH$_2$Cl | 4-Cl | N | T |
| I-302 | CH$_3$ | CHCl$_2$ | 4-Cl | N | T |
| I-303 | CH$_3$ | CCl$_3$ | 4-Cl | N | T |
| I-304 | CH$_3$ | CH$_2$CH$_2$Cl | 4-Cl | N | T |
| I-305 | CH$_3$ | CHClCH$_3$ | 4-Cl | N | T |
| I-306 | CH$_3$ | CH$_2$CHCl$_2$ | 4-Cl | N | T |
| I-307 | CH$_3$ | CHClCH$_2$Cl | 4-Cl | N | T |
| I-308 | CH$_3$ | CH$_2$CCl$_3$ | 4-Cl | N | T |
| I-309 | CH$_3$ | CH$_2$CH$_2$CH$_2$Cl | 4-Cl | N | T |
| I-310 | CH$_3$ | CH$_2$CHClCH$_2$Cl | 4-Cl | N | T |
| I-311 | CH$_3$ | CCl(CH$_3$)CH$_3$ | 4-Cl | N | T |
| I-312 | CH$_3$ | CH(CH$_2$Cl)CH$_3$ | 4-Cl | N | T |
| I-313 | CH$_3$ | CH$_2$CH$_2$CH$_2$CH$_2$Cl | 4-Cl | N | T |
| I-314 | CH$_3$ | CH=CCl$_2$ | 4-Cl | N | T |
| I-315 | CH$_3$ | CH$_2$CCl=CH$_2$ | 4-Cl | N | T |
| I-316 | CH$_3$ | CH$_2$CH=CCl$_2$ | 4-Cl | N | T |
| I-317 | CH$_3$ | CH$_2$CCl=CHCl | 4-Cl | N | T |
| I-318 | CH$_3$ | CH$_2$CH=C(Cl)CH$_3$ | 4-Cl | N | T |
| I-319 | CH$_3$ | C≡CCl | 4-Cl | N | T |
| I-320 | CH$_3$ | CH$_2$F | 4-Cl | N | T |
| I-321 | CH$_3$ | CF$_3$ | 4-Cl | N | T |
| I-322 | CH$_3$ | CH$_2$CH$_2$F | 4-Cl | N | T |
| I-323 | CH$_3$ | CH$_2$CF$_3$ | 4-Cl | N | T |
| I-324 | CH$_3$ | CH=CF$_2$ | 4-Cl | N | T |

TABLE 7-continued

| Compound No. | $(R^a)X^a n^{a1)}$ | $(R^b)X^b n^{b2)}$ | $Y m^{3)}$ | A | Type |
|---|---|---|---|---|---|
| I-325 | CH$_3$ | CH$_2$Br | 4-Cl | N | T |
| I-326 | CH$_3$ | CH$_2$CH$_2$Br | 4-Cl | N | T |
| I-327 | CH$_3$ | CHBrCH$_3$ | 4-Cl | N | T |
| I-328 | CH$_3$ | CH$_2$CHCl$_2$ | 4-Cl | N | T |
| I-329 | CH$_3$ | CHBrCH$_2$Br | 4-Cl | N | T |
| I-330 | CH$_3$ | CH$_2$CHBrCH$_2$Br | 4-Cl | N | T |
| I-331 | CH$_3$ | CBr(CH$_3$)CH$_3$ | 4-Cl | N | T |
| I-332 | CH$_3$ | CH(CH$_2$Br)CH$_3$ | 4-Cl | N | T |
| I-333 | CH$_3$ | CH$_2$CBr=CH$_2$ | 4-Cl | N | T |
| I-334 | CH$_3$ | CH$_2$C≡CBr | 4-Cl | N | T |
| I-335 | CH$_3$ | CH$_2$I | 4-Cl | N | T |
| I-336 | CH$_2$CH$_3$ | CH$_2$Cl | 4-Cl | N | T |
| I-337 | CH$_2$CH$_3$ | CH$_2$CH$_2$Cl | 4-Cl | N | T |
| I-338 | CH$_2$CH$_3$ | CHClCH$_2$Cl | 4-Cl | N | T |
| I-339 | CH$_2$CH$_3$ | CH$_2$CH$_2$CH$_2$Cl | 4-Cl | N | T |
| I-340 | CH$_2$CH$_3$ | CCl(CH$_3$)CH$_3$ | 4-Cl | N | T |
| I-341 | CH$_2$CH$_3$ | CH(CH$_2$Cl)CH$_3$ | 4-Cl | N | T |
| I-342 | CH$_2$CH$_3$ | CH=CCl$_2$ | 4-Cl | N | T |
| I-343 | CH$_2$CH$_3$ | CH$_2$CCl=CH$_2$ | 4-Cl | N | T |
| I-344 | CH$_2$CH$_3$ | CH$_2$CH=CCl$_2$ | 4-Cl | N | T |
| I-345 | CH$_2$CH$_3$ | CH$_2$F | 4-Cl | N | T |
| I-346 | CH$_2$CH$_3$ | CF$_3$ | 4-Cl | N | T |
| I-347 | CH$_2$CH$_3$ | CH$_2$CH$_2$F | 4-Cl | N | T |
| I-348 | CH$_2$CH$_3$ | CF(CH$_3$)CH$_3$ | 4-Cl | N | T |
| I-349 | CH$_2$CH$_3$ | CH$_2$Br | 4-Cl | N | T |

TABLE 8

| Compound No. | $(R^a)X^a n^{a1)}$ | $(R^b)X^b n^{b2)}$ | $Y m^{3)}$ | A | Type |
|---|---|---|---|---|---|
| I-350 | CH$_2$CH$_3$ | CHBrCH$_2$Br | 4-Cl | N | T |
| I-351 | CH$_2$CH$_3$ | CBr(CH$_3$)CH$_3$ | 4-Cl | N | T |
| I-352 | CH$_2$CH$_3$ | CH=CBr$_2$ | 4-Cl | N | T |
| I-353 | CH$_2$CH$_3$ | CH$_2$CBr=CH$_2$ | 4-Cl | N | T |
| I-354 | CH$_2$CH$_3$ | CH$_2$I | 4-Cl | N | T |
| I-355 | H | CH$_2$Cl | 4-Cl | N | T |
| I-356 | H | CH$_2$CH$_2$Cl | 4-Cl | N | T |
| I-357 | H | CHClCH$_2$Cl | 4-Cl | N | T |
| I-358 | H | CH$_2$CH$_2$CH$_2$Cl | 4-Cl | N | T |
| I-359 | H | CCl(CH$_3$)CH$_3$ | 4-Cl | N | T |
| I-360 | H | CH(CH$_2$Cl)CH$_3$ | 4-Cl | N | T |
| I-361 | H | CH=CCl$_2$ | 4-Cl | N | T |
| I-362 | H | CH$_2$CCl=CH$_2$ | 4-Cl | N | T |
| I-363 | H | CH$_2$CH=CCl$_2$ | 4-Cl | N | T |
| I-364 | H | CH$_2$F | 4-Cl | N | T |
| I-365 | H | CF$_3$ | 4-Cl | N | T |
| I-366 | H | CH$_2$CH$_2$F | 4-Cl | N | T |
| I-367 | H | CF(CH$_3$)CH$_3$ | 4-Cl | N | T |
| I-368 | H | CH$_2$Br | 4-Cl | N | T |
| I-369 | H | CHBrCH$_2$Br | 4-Cl | N | T |
| I-370 | H | CBr(CH$_3$)CH$_3$ | 4-Cl | N | T |
| I-371 | H | CH=CBr$_2$ | 4-Cl | N | T |
| I-372 | H | CH$_2$CBr=CH$_2$ | 4-Cl | N | T |
| I-373 | CH$_3$ | CH$_2$Cl | — | N | T |
| I-374 | CH$_3$ | CH$_2$Cl | 3-Cl | N | T |
| I-375 | CH$_3$ | CH$_2$Cl | 3,4-Cl$_2$ | N | T |
| I-376 | CH$_3$ | CH$_2$Cl | 4-Br | N | T |
| I-377 | CH$_3$ | CH$_2$Cl | 4-F | N | T |
| I-378 | CH$_3$ | CH$_2$Cl | 4-CF$_3$ | N | T |
| I-379 | CH$_3$ | CH$_2$Cl | 4-OCF$_3$ | N | T |
| I-380 | CH$_3$ | CH$_2$Cl | 4-Me | N | T |
| I-381 | CH$_3$ | CH$_2$Cl | 4-OMe | N | T |
| I-382 | CH$_3$ | CH$_2$Cl | 4-Ph | N | T |
| I-383 | CH$_3$ | CH$_2$Cl | 4-CN | N | T |
| I-384 | CH$_3$ | CH$_2$Cl | 4-NO$_2$ | N | T |
| I-385 | CH$_3$ | CH$_2$Cl | 2-Cl | N | T |
| I-386 | CH$_3$ | CH$_2$Cl | 2-F | N | T |
| I-387 | CH$_3$ | CH$_2$Cl | 2,4-Cl$_2$ | N | T |
| I-388 | CH$_3$ | CH$_2$Cl | 2,4-F$_2$ | N | T |
| I-389 | CH$_3$ | CH$_2$Cl | 3-F, 4-Cl | N | T |
| I-390 | CH$_3$ | CH$_2$Cl | 2-F, 4-Cl | N | T |
| I-391 | CH$_2$CH$_3$ | CH$_2$Cl | 4-F | N | T |
| I-392 | CH$_2$CH$_3$ | CH$_2$Cl | 4-CF$_3$ | N | T |
| I-393 | CH$_2$CH$_3$ | CH$_2$Cl | 4-OCF$_3$ | N | T |
| I-394 | CH$_2$CH$_3$ | CH$_2$Cl | 4-Me | N | T |

TABLE 8-continued

| Compound No. | $(R^a)X^an^{a1)}$ | $(R^b)X^bn^{b2)}$ | $Ym^{3)}$ | A | Type |
|---|---|---|---|---|---|
| I-395 | $CH_2CH_3$ | $CH_2Cl$ | 4-OMe | N | T |
| I-396 | $CH_2CH_3$ | $CH_2Cl$ | 4-Ph | N | T |
| I-397 | $CH_2CH_3$ | $CH_2Cl$ | — | N | T |
| I-398 | $CH_2CH_3$ | $CH_2Cl$ | 2,4-$F_2$ | N | T |

TABLE 9

| Compound No. | $(R^a)X^an^{a1)}$ | $(R^b)X^bn^{b2)}$ | $Ym^{3)}$ | A | Type |
|---|---|---|---|---|---|
| I-401 | $CH_2Cl$ | $CH_3$ | 4-Cl | N | T |
| I-402 | $CHCl_2$ | $CH_3$ | 4-Cl | N | T |
| I-403 | $CCl_3$ | $CH_3$ | 4-Cl | N | T |
| I-404 | $CH_2CH_2Cl$ | $CH_3$ | 4-Cl | N | T |
| I-405 | $CHClCH_3$ | $CH_3$ | 4-Cl | N | T |
| I-406 | $CH_2CHCl_2$ | $CH_3$ | 4-Cl | N | T |
| I-407 | $CHClCH_2Cl$ | $CH_3$ | 4-Cl | N | T |
| I-408 | $CH_2CCl_3$ | $CH_3$ | 4-Cl | N | T |
| I-409 | $CH_2CH_2CH_2Cl$ | $CH_3$ | 4-Cl | N | T |
| I-410 | $CH_2CHClCH_2Cl$ | $CH_3$ | 4-Cl | N | T |
| I-411 | $CCl(CH_3)CH_3$ | $CH_3$ | 4-Cl | N | T |
| I-412 | $CH(CH_2Cl)CH_3$ | $CH_3$ | 4-Cl | N | T |
| I-413 | $CH_2CH_2CH_2CH_2Cl$ | $CH_3$ | 4-Cl | N | T |
| I-414 | $CH=CCl_2$ | $CH_3$ | 4-Cl | N | T |
| I-415 | $CH_2CCl=CH_2$ | $CH_3$ | 4-Cl | N | T |
| I-416 | $CH_2CH=CCl_2$ | $CH_3$ | 4-Cl | N | T |
| I-417 | $CH_2CCl=CHCl$ | $CH_3$ | 4-Cl | N | T |
| I-418 | $CH_2CH=C(Cl)CH_3$ | $CH_3$ | 4-Cl | N | T |
| I-419 | $C\equiv CCl$ | $CH_3$ | 4-Cl | N | T |
| I-420 | $CH_2F$ | $CH_3$ | 4-Cl | N | T |
| I-421 | $CF_3$ | $CH_3$ | 4-Cl | N | T |
| I-422 | $CH_2CH_2F$ | $CH_3$ | 4-Cl | N | T |
| I-423 | $CH_2CF_3$ | $CH_3$ | 4-Cl | N | T |
| I-424 | $CH=CF_2$ | $CH_3$ | 4-Cl | N | T |
| I-425 | $CH_2Br$ | $CH_3$ | 4-Cl | N | T |
| I-426 | $CH_2CH_2Br$ | $CH_3$ | 4-Cl | N | T |
| I-427 | $CHBrCH_3$ | $CH_3$ | 4-Cl | N | T |
| I-428 | $CH_2CHCl_2$ | $CH_3$ | 4-Cl | N | T |
| I-429 | $CHBrCH_2Br$ | $CH_3$ | 4-Cl | N | T |
| I-430 | $CH_2CHBrCH_2Br$ | $CH_3$ | 4-Cl | N | T |
| I-431 | $CBr(CH_3)CH_3$ | $CH_3$ | 4-Cl | N | T |
| I-432 | $CH(CH_2Br)CH_3$ | $CH_3$ | 4-Cl | N | T |
| I-433 | $CH_2CBr=CH_2$ | $CH_3$ | 4-Cl | N | T |
| I-434 | $CH_2C\equiv CBr$ | $CH_3$ | 4-Cl | N | T |
| I-435 | $CH_2I$ | $CH_3$ | 4-Cl | N | T |
| I-436 | $CH_2Cl$ | $CH_2CH_3$ | 4-Cl | N | T |
| I-437 | $CH_2CH_2Cl$ | $CH_2CH_3$ | 4-Cl | N | T |
| I-438 | $CHClCH_2Cl$ | $CH_2CH_3$ | 4-Cl | N | T |
| I-439 | $CH_2CH_2CH_2Cl$ | $CH_2CH_3$ | 4-Cl | N | T |
| I-440 | $CCl(CH_3)CH_3$ | $CH_2CH_3$ | 4-Cl | N | T |
| I-441 | $CH(CH_2Cl)CH_3$ | $CH_2CH_3$ | 4-Cl | N | T |
| I-442 | $CH=CCl_2$ | $CH_2CH_3$ | 4-Cl | N | T |
| I-443 | $CH_2CCl=CH_2$ | $CH_2CH_3$ | 4-Cl | N | T |
| I-444 | $CH_2CH=CCl_2$ | $CH_2CH_3$ | 4-Cl | N | T |
| I-445 | $CH_2F$ | $CH_2CH_3$ | 4-Cl | N | T |
| I-446 | $CF_3$ | $CH_2CH_3$ | 4-Cl | N | T |
| I-447 | $CH_2CH_2F$ | $CH_2CH_3$ | 4-Cl | N | T |
| I-448 | $CF(CH_3)CH_3$ | $CH_2CH_3$ | 4-Cl | N | T |
| I-449 | $CH_2Br$ | $CH_2CH_3$ | 4-Cl | N | T |

TABLE 10

| Compound No. | $(R^a)X^an^{a1)}$ | $(R^b)X^bn^{b2)}$ | $Ym^{3)}$ | A | Type |
|---|---|---|---|---|---|
| I-450 | $CHBrCH_2Br$ | $CH_2CH_3$ | 4-Cl | N | T |
| I-451 | $CBr(CH_3)CH_3$ | $CH_2CH_3$ | 4-Cl | N | T |
| I-452 | $CH=CBr_2$ | $CH_2CH_3$ | 4-Cl | N | T |
| I-453 | $CH_2CBr=CH_2$ | $CH_2CH_3$ | 4-Cl | N | T |
| I-454 | $CH_2I$ | $CH_2CH_3$ | 4-Cl | N | T |
| I-455 | $CH_2Cl$ | H | 4-Cl | N | T |
| I-456 | $CH_2CH_2Cl$ | H | 4-Cl | N | T |
| I-457 | $CHClCH_2Cl$ | H | 4-Cl | N | T |
| I-458 | $CH_2CH_2CH_2Cl$ | H | 4-Cl | N | T |
| I-459 | $CCl(CH_3)CH_3$ | H | 4-Cl | N | T |

TABLE 10-continued

| Compound No. | $(R^a)X^an^{a1)}$ | $(R^b)X^bn^{b2)}$ | $Ym^{3)}$ | A | Type |
|---|---|---|---|---|---|
| I-460 | $CH(CH_2Cl)CH_3$ | H | 4-Cl | N | T |
| I-461 | $CH=CCl_2$ | H | 4-Cl | N | T |
| I-462 | $CH_2CCl=CH_2$ | H | 4-Cl | N | T |
| I-463 | $CH_2CH=CCl_2$ | H | 4-Cl | N | T |
| I-464 | $CH_2F$ | H | 4-Cl | N | T |
| I-465 | $CF_3$ | H | 4-Cl | N | T |
| I-466 | $CH_2CH_2F$ | H | 4-Cl | N | T |
| I-467 | $CF(CH_3)CH_3$ | H | 4-Cl | N | T |
| I-468 | $CH_2Br$ | H | 4-Cl | N | T |
| I-469 | $CHBrCH_2Br$ | H | 4-Cl | N | T |
| I-470 | $CBr(CH_3)CH_3$ | H | 4-Cl | N | T |
| I-471 | $CH=CBr_2$ | H | 4-Cl | N | T |
| I-472 | $CH_2CBr=CH_2$ | H | 4-Cl | N | T |
| I-473 | $CH_2Cl$ | $CH_3$ | — | N | T |
| I-474 | $CH_2Cl$ | $CH_3$ | 3-Cl | N | T |
| I-475 | $CH_2Cl$ | $CH_3$ | 3,4-$Cl_2$ | N | T |
| I-476 | $CH_2Cl$ | $CH_3$ | 4-Br | N | T |
| I-477 | $CH_2Cl$ | $CH_3$ | 4-F | N | T |
| I-478 | $CH_2Cl$ | $CH_3$ | 4-$CF_3$ | N | T |
| I-479 | $CH_2Cl$ | $CH_3$ | 4-$OCF_3$ | N | T |
| I-480 | $CH_2Cl$ | $CH_3$ | 4-Me | N | T |
| I-481 | $CH_2Cl$ | $CH_3$ | 4-OMe | N | T |
| I-482 | $CH_2Cl$ | $CH_3$ | 4-Ph | N | T |
| I-483 | $CH_2Cl$ | $CH_3$ | 4-CN | N | T |
| I-484 | $CH_2Cl$ | $CH_3$ | 4-$NO_2$ | N | T |
| I-485 | $CH_2Cl$ | $CH_3$ | 2-Cl | N | T |
| I-486 | $CH_2Cl$ | $CH_3$ | 2-F | N | T |
| I-487 | $CH_2Cl$ | $CH_3$ | 2,4-$Cl_2$ | N | T |
| I-488 | $CH_2Cl$ | $CH_3$ | 2,4-$F_2$ | N | T |
| I-489 | $CH_2Cl$ | $CH_3$ | 3-F, 4-Cl | N | T |
| I-490 | $CH_2Cl$ | $CH_3$ | 2-F, 4-Cl | N | T |
| I-491 | $CH_2Cl$ | $CH_2CH_3$ | 4-F | N | T |
| I-492 | $CH_2Cl$ | $CH_2CH_3$ | 4-$CF_3$ | N | T |
| I-493 | $CH_2Cl$ | $CH_2CH_3$ | 4-$OCF_3$ | N | T |
| I-494 | $CH_2Cl$ | $CH_2CH_3$ | 4-Me | N | T |
| I-495 | $CH_2Cl$ | $CH_2CH_3$ | 4-OMe | N | T |
| I-496 | $CH_2Cl$ | $CH_2CH_3$ | 4-Ph | N | T |
| I-497 | $CH_2Cl$ | $CH_2CH_3$ | — | N | T |
| I-498 | $CH_2Cl$ | $CH_2CH_3$ | 2,4-$F_2$ | N | T |

TABLE 11

| Compound No. | $(R^a)X^an^{a1)}$ | $(R^b)X^bn^{b2)}$ | $Ym^{3)}$ | A | Type |
|---|---|---|---|---|---|
| I-501 | $CH(CH_3)CH_3$ | $CH_2Cl$ | 4-Cl | N | T |
| I-502 | $CH_2CH_2CH_3$ | $CH_2Cl$ | 4-Cl | N | T |
| I-503 | $CH_2Cl$ | $CH_2Cl$ | 4-Cl | N | T |
| I-504 | $CH_2CH_2Cl$ | $CH_2Cl$ | 4-Cl | N | T |
| I-505 | $CH(CH_3)CH_3$ | $CH_2CH_2Cl$ | 4-Cl | N | T |
| I-506 | $CH_2CH_2CH_2CH_3$ | $CH_2CH_2Cl$ | 4-Cl | N | T |
| I-507 | $CH_2Cl$ | $CH_2CH_2Cl$ | 4-Cl | N | T |
| I-508 | $CH_2CH_2Cl$ | $CH_2CH_2Cl$ | 4-Cl | N | T |
| I-509 | $CH(CH_3)CH_3$ | $CH=CCl_2$ | 4-Cl | N | T |
| I-510 | $CH_2CH_2CH_3$ | $CH=CCl_2$ | 4-Cl | N | T |
| I-511 | $CH(CH_3)CH_3$ | $CH_2CCl=CH_2$ | 4-Cl | N | T |
| I-512 | $CH_2CH_2CH_3$ | $CH_2CCl=CH_2$ | 4-Cl | N | T |
| I-513 | $CH(CH_3)CH_3$ | $CF_3$ | 4-Cl | N | T |
| I-514 | $CH_2CH_2CH_3$ | $CF_3$ | 4-Cl | N | T |
| I-515 | $CH(CH_3)CH_3$ | $CH_2CF_3$ | 4-Cl | N | T |
| I-516 | $CH_2CH_2CH_3$ | $CH_2CF_3$ | 4-Cl | N | T |
| I-517 | $CH_2CF_3$ | $CH_2CF_3$ | 4-Cl | N | T |
| I-518 | $CH_2CH_2CH_3$ | $CH_2Br$ | 4-Cl | N | T |
| I-519 | $CH(CH_3)CH_3$ | $CH_2Br$ | 4-Cl | N | T |
| I-520 | $CH_2CH_2CH_3$ | $CH_2I$ | 4-Cl | N | T |
| I-521 | $CH(CH_3)CH_3$ | $CH_2I$ | 4-Cl | N | T |
| I-522 | $CH_2Cl$ | $CH(CH_3)CH_3$ | 3-Cl | N | T |
| I-523 | $CH_2Cl$ | $CH_2CH_2CH_3$ | 2-Cl | N | T |
| I-524 | $CH_2Cl$ | $CH_2Cl$ | 3,4-$Cl_2$ | N | T |
| I-525 | $CH_2Cl$ | $CH_2CH_2Cl$ | 4-F | N | T |
| I-526 | $CH_2CH_2Cl$ | $CH(CH_3)CH_3$ | 3-F | N | T |
| I-527 | $CH_2CH_2Cl$ | $CH_2CH_2CH_2CH_3$ | 4-$CF_3$ | N | T |
| I-528 | $CH_2CH_2Cl$ | $CH_2Cl$ | 4-$OCF_3$ | N | T |
| I-529 | $CH_2CH_2Cl$ | $CH_2CH_2Cl$ | 4-Ph | N | T |
| I-530 | $CH=CCl_2$ | $CH(CH_3)CH_3$ | 4-Me | N | T |

TABLE 11-continued

| Compound No. | $(R^a)X^a{n^{a1}}$ | $(R^b)X^b{n^{b2}}$ | $Ym^{3)}$ | A | Type |
|---|---|---|---|---|---|
| I-531 | CH=CCl$_2$ | CH$_2$CH$_2$CH$_3$ | — | N | T |
| I-532 | CH$_2$CCl=CH$_2$ | CH(CH$_3$)CH$_3$ | 4-Br | N | T |
| I-533 | CH$_2$CCl=CH$_2$ | CH$_2$CH$_2$CH$_3$ | 4-Cl | N | T |
| I-534 | CF$_3$ | CH(CH$_3$)CH$_3$ | 4-Cl | N | T |
| I-535 | CF$_3$ | CH$_2$CH$_2$CH$_3$ | 4-Cl | N | T |
| I-536 | CH$_2$CF$_3$ | CH(CH$_3$)CH$_3$ | 4-Cl | N | T |
| I-537 | CH$_2$CF$_3$ | CH$_2$CH$_2$CH$_3$ | 4-Cl | N | T |
| I-538 | CH$_2$CF$_3$ | CH$_2$CF$_3$ | 4-Cl | N | T |
| I-539 | CH$_2$Br | CH$_2$CH$_2$CH$_3$ | 4-Cl | N | T |
| I-540 | CH$_2$Br | CH(CH$_3$)CH$_3$ | 4-Cl | N | T |
| I-541 | CH$_2$I | CH$_2$CH$_2$CH$_3$ | 4-Cl | N | T |
| I-542 | CH$_2$I | CH(CH$_3$)CH$_3$ | 4-Cl | N | T |
| I-543 | CH$_2$Cl | CH$_3$ | 4-Cl | CH | T |
| I-544 | CH$_3$ | CH$_2$Cl | 4-Cl | CH | T |
| I-545 | CH$_2$CH$_3$ | CH$_2$Cl | 4-Cl | CH | T |
| I-546 | CH(CH$_3$)CH$_3$ | CH$_2$Cl | 4-Cl | CH | T |
| I-547 | CH$_2$CH$_2$CH$_3$ | CH$_2$Cl | 4-Cl | CH | T |
| I-548 | CH$_2$Cl | CH$_2$Cl | 4-Cl | CH | T |
| I-549 | CH$_2$CH$_2$Cl | CH$_2$Cl | 4-Cl | CH | T |
| I-550 | CH(CH$_3$)CH$_3$ | CH$_2$Cl | 4-Cl | CH | T |

TABLE 12

| Compound No. | $(R^a)X^a{n^{a1}}$ | $(R^b)X^b{n^{b2}}$ | $Ym^{3)}$ | A | Type |
|---|---|---|---|---|---|
| I-551 | CH$_2$CH$_2$CH$_2$CH$_3$ | CH$_2$Cl | 4-Cl | CH | T |
| I-552 | CH=CCl$_2$ | CH$_2$Cl | 4-Cl | CH | T |
| I-553 | CH$_2$CCl=CH$_2$ | CH$_2$Cl | 4-Cl | CH | T |
| I-554 | CF$_3$ | CH$_2$Cl | 3-Cl | CH | T |
| I-555 | CH$_2$CF$_3$ | CH$_2$Cl | 2-Cl | CH | T |
| I-556 | CH$_2$Br | CH$_2$Cl | 3,4-Cl$_2$ | CH | T |
| I-557 | CH$_3$ | CH$_2$CH$_2$Cl | 4-F | CH | T |
| I-558 | CH$_2$CH$_3$ | CH$_2$CH$_2$Cl | 3-F | CH | T |
| I-559 | CH(CH$_3$)CH$_3$ | CH$_2$CH$_2$Cl | 4-CF$_3$ | CH | T |
| I-560 | CH$_2$CH$_2$CH$_3$ | CH$_2$CH$_2$Cl | 4-OCF$_3$ | CH | T |
| I-561 | CH$_2$Cl | CH$_3$ | 4-Ph | CH | T |
| I-562 | CH$_2$Cl | CH$_2$CH$_3$ | 4-Me | CH | T |
| I-563 | CH$_2$Cl | CH(CH$_3$)CH$_3$ | 3-Br | CH | T |
| I-564 | CH$_2$Cl | CH$_2$CH$_2$CH$_3$ | 4-Br | CH | T |
| I-565 | CH$_2$Cl | CH$_2$Cl | 4-Cl | CH | T |
| I-566 | CH$_2$Cl | CH$_2$CH$_2$Cl | 4-Cl | CH | T |
| I-567 | CH$_2$Cl | CH(CH$_3$)CH$_3$ | 4-Cl | CH | T |
| I-568 | CH$_2$Cl | CH$_2$CH$_2$CH$_2$CH$_3$ | 4-Cl | CH | T |
| I-569 | CH$_2$Cl | CH=CCl$_2$ | 4-Cl | CH | T |
| I-570 | CH$_2$Cl | CH$_2$CCl=CH$_2$ | 4-Cl | CH | T |
| I-571 | CH$_2$Cl | CF$_3$ | 4-Cl | CH | T |
| I-572 | CH$_2$Cl | CH$_2$CF$_3$ | 4-Cl | CH | T |
| I-573 | CH$_2$Cl | CH$_2$Br | 4-Cl | CH | T |
| I-574 | CH$_2$CH$_2$Cl | CH$_3$ | 4-Cl | CH | T |
| I-575 | CH$_2$CH$_2$Cl | CH$_2$CH$_3$ | 4-Cl | CH | T |
| I-576 | CH$_2$CH$_2$Cl | CH(CH$_3$)CH$_3$ | 4-Cl | CH | T |
| I-577 | CH$_2$CH$_2$Cl | CH$_2$CH$_2$CH$_3$ | 4-Cl | CH | T |
| I-578 | CH$_3$ | CH$_2$Cl | 3-Cl | CH | C |
| I-579 | CH$_3$ | CH$_2$Cl | 2-Cl | CH | C |
| I-580 | CH$_3$ | CH$_2$Cl | 4-F | CH | C |
| I-581 | CH$_3$ | CH$_2$Cl | 3-F | CH | C |
| I-582 | CH$_3$ | CH$_2$Cl | 2-F | CH | C |
| I-583 | CH$_3$ | CH$_2$Cl | 4-OCF$_3$ | CH | C |
| I-584 | CH$_3$ | CH$_2$Cl | 4-CF$_3$ | CH | C |
| I-585 | CH$_3$ | CH$_2$Cl | 2,4-Cl$_2$ | CH | C |
| I-586 | CH$_3$ | CH$_2$Cl | 2,4-F$_2$ | CH | C |
| I-587 | CH$_3$ | CH$_2$Cl | 4-Ph | CH | C |
| I-588 | CH$_3$ | CH$_2$Cl | 4-Br | CH | C |
| I-589 | CH$_2$Cl | CH$_3$ | 3-Cl | CH | C |
| I-590 | CH$_2$Cl | CH$_3$ | 2-Cl | CH | C |
| I-591 | CH$_2$Cl | CH$_3$ | 4-F | CH | C |
| I-592 | CH$_2$Cl | CH$_3$ | 3-F | CH | C |
| I-593 | CH$_2$Cl | CH$_3$ | 2-F | CH | C |
| I-594 | CH$_2$Cl | CH$_3$ | 4-OCF$_3$ | CH | C |
| I-595 | CH$_2$Cl | CH$_3$ | 4-CF$_3$ | CH | C |
| I-596 | CH$_2$Cl | CH$_3$ | 2,4-Cl$_2$ | CH | C |
| I-597 | CH$_2$Cl | CH$_3$ | 2,4-F$_2$ | CH | C |
| I-598 | CH$_2$Cl | CH$_3$ | 4-Ph | CH | C |
| I-599 | CH$_2$Cl | CH$_3$ | 4-Br | CH | C |

TABLE 13

| Compound No. | $(R^a)X^a{n^a}$ | $(R^b)X^b{n^b}$ | Ym | A | Type |
|---|---|---|---|---|---|
| I-601 | CH$_3$ | CH$_2$Br | 4-F | N | C |
| I-602 | CH$_3$ | CH$_2$Br | — | N | C |
| I-603 | CH$_3$ | CH$_2$Br | 3-Cl | N | C |
| I-604 | CH$_3$ | CH$_2$Br | 2-Cl | N | C |
| I-605 | CH$_3$ | CH$_2$Br | 3-F | N | C |
| I-606 | CH$_3$ | CH$_2$Br | 2-F | N | C |
| I-607 | CH$_3$ | CH$_2$Br | 4-OCF$_3$ | N | C |
| I-608 | CH$_3$ | CH$_2$Br | 4-CF$_3$ | N | C |
| I-609 | CH$_3$ | CH$_2$Br | 4-Me | N | C |
| I-610 | CH$_2$CH$_3$ | CH$_2$Br | 4-Cl | N | C |
| I-611 | CH$_2$CH$_3$ | CH$_2$Br | 4-F | N | C |
| I-612 | CH$_2$CH$_3$ | CH$_2$Br | — | N | C |
| I-613 | CH$_3$ | CH$_2$Br | 4-F | N | T |
| I-614 | CH$_3$ | CH$_2$Br | — | N | T |
| I-615 | CH$_3$ | CH$_2$Br | 3-Cl | N | T |
| I-616 | CH$_3$ | CH$_2$Br | 2-Cl | N | T |
| I-617 | CH$_3$ | CH$_2$Br | 3-F | N | T |
| I-618 | CH$_3$ | CH$_2$Br | 2-F | N | T |
| I-619 | CH$_3$ | CH$_2$Br | 4-OCF$_3$ | N | T |
| I-620 | CH$_3$ | CH$_2$Br | 4-CF$_3$ | N | T |
| I-621 | CH$_3$ | CH$_2$Br | 4-Me | N | T |
| I-622 | CH$_2$CH$_3$ | CH$_2$Br | 4-Cl | N | T |
| I-623 | CH$_2$CH$_3$ | CH$_2$Br | 4-F | N | T |
| I-624 | CH$_2$CH$_3$ | CH$_2$Br | — | N | T |
| I-625 | CH$_2$Br | CH$_3$ | 4-F | CH | C |
| I-626 | CH$_2$Br | CH$_3$ | — | CH | C |
| I-627 | CH$_2$Br | CH$_3$ | 3-Cl | CH | C |
| I-628 | CH$_2$Br | CH$_3$ | 2-Cl | CH | C |
| I-629 | CH$_2$Br | CH$_3$ | 3-F | N | C |
| I-630 | CH$_2$Br | CH$_3$ | 2-F | N | C |
| I-631 | CH$_2$Br | CH$_3$ | 4-OCF$_3$ | CH | C |
| I-632 | CH$_2$Br | CH$_3$ | 4-CF$_3$ | CH | C |
| I-633 | CH$_2$Br | CH$_3$ | 4-Me | CH | C |
| I-634 | CH$_2$Br | CH$_2$CH$_3$ | 4-Cl | CH | C |
| I-635 | CH$_2$Br | CH$_2$CH$_3$ | 4-F | CH | C |
| I-636 | CH$_2$Br | CH$_2$CH$_3$ | — | CH | C |
| I-637 | CH$_2$Br | CH$_3$ | 4-F | CH | T |
| I-638 | CH$_2$Br | CH$_3$ | — | CH | T |
| I-639 | CH$_2$Br | CH$_3$ | 3-Cl | CH | T |
| I-640 | CH$_2$Br | CH$_3$ | 2-Cl | CH | T |
| I-641 | CH$_2$Br | CH$_3$ | 3-F | N | T |
| I-642 | CH$_2$Br | CH$_3$ | 2-F | N | T |
| I-643 | CH$_2$Br | CH$_3$ | 4-OCF$_3$ | CH | T |
| I-644 | CH$_2$Br | CH$_3$ | 4-CF$_3$ | CH | T |
| I-645 | CH$_2$Br | CH$_3$ | 4-Me | CH | T |
| I-646 | CH$_2$Br | CH$_2$CH$_3$ | 4-Cl | CH | T |
| I-647 | CH$_2$Br | CH$_2$CH$_3$ | 4-F | CH | T |
| I-648 | CH$_2$Br | CH$_2$CH$_3$ | — | CH | T |

2. Methods for producing 2-(Halogenated hydrocarbon-substituted)-5-benzyl-1-azolylmethylcyclopentanol derivatives The method for producing Compound (I) is described below. Solvents, bases, acids and the like employed in each step in each production method described below may be those listed below unless otherwise specified.

(1) Solvents

While the solvent employed is not limited particularly unless it is involved in a reaction, it may usually be ethers such as diethyl ether, tetrahydrofuran, dioxane and the like, alcohols such as methanol, ethanol, isopropanol and the like, aromatic hydrocarbons such as benzene, toluene, xylene and the like, aliphatic hydrocarbons such as petroleum ether, hexane, methylcyclohexane and the like, amides such as N,N-dimethylformamide, N,N-dimethylacetamide, N-methyl-2-pyrrolidinone and the like. Otherwise, solvents may for example be water, acetonitrile, ethyl acetate, acetic anhydride, acetic acid, pyridine, dimethyl sulfoxide and the like. Two or more of these solvents may be employed in combination.

One which may also be exemplified as a solvent is a solvent composition consisting of solvents which do not form a homogenous layer with each other. In such a case, a phase transfer catalyst such as a customary employed quaternary ammonium salt or a crown ether can be added to the reaction system.

(2) Bases and Acids

To the solvent described above, a base or an acid may be added.

The base employed is not limited particularly. The base may for example be a carbonate of an alkaline metal such as sodium carbonate, sodium hydrogen carbonate, potassium carbonate, potassium hydrogen carbonate and the like; a carbonate of an alkaline earth metal such as calcium carbonate, barium carbonate and the like; a hydroxide of an alkaline metal such as sodium hydroxide, potassium hydroxide and the like; an alkaline metal such as lithium, sodium, potassium and the like; an alkoxide of an alkaline metal such as sodium methoxide, sodium ethoxide, potassium t-butoxide and the like; an alkaline metal hydride such as sodium hydride, potassium hydride, lithium hydride and the like; an organic metal compound of an alkaline metal such as n-butyl lithium and the like; an alkaline metal such as sodium, potassium, lithium and the like; an alkaline metal amide such as lithium diisopropyl amide and the like; and an organic amine such as triethylamine, pyridine, 4-dimethylaminopyridine, N,N-dimethylaniline, 1,8-diazabicyclo-7-[5.4.0]undecene and the like.

The acid employed is not limited particularly. The acid may for example be an inorganic acid such as hydrochloric acid, hydrobromic acid, hydroiodic acid, sulfuric acid and the like, an organic acid such as formic acid, acetic acid, butyric acid, trifluoroacetic acid, p-toluenesulfonic acid and the like, a Lewis acid such as lithium chloride, lithium bromide, rhodium chloride, aluminum chloride, boron trifluoride and the like.

As used herein, "halogenic acid" refers to hydrofluoric acid, hydrochloric acid, hydrobromic acid and hydroiodic acid. The halogenic acid may be a gas, a liquid, or an aqueous solution. It is also possible to use as a solution formed by dissolving it in a suitable organic solvent.

(3) First Method for Producing Compound (I)

(3-1) Step 1A

Next, a production method according to the invention is described below. One embodiment of this production method comprises a step for substituting a certain functional group in a compound represented by Formula (II) shown below with a halogen atom to obtain a 2-(halogenated hydrocarbon-substituted)-5-benzyl-1-azolylmethylcyclopentanol derivative represented by Formula (Ia) shown below (Step 1A) (see Scheme (1) shown below). The compound represented by Formula (II) shown below is a compound having a leaving group on the substituent in 2-position of the cyclopentane ring. Hereinafter the compound represented by Formula (II) is referred to as "Compound (II)", while the compound represented by Formula (Ia) is referred to as "Compound (Ia)".

Scheme (1)

[Chem.16]

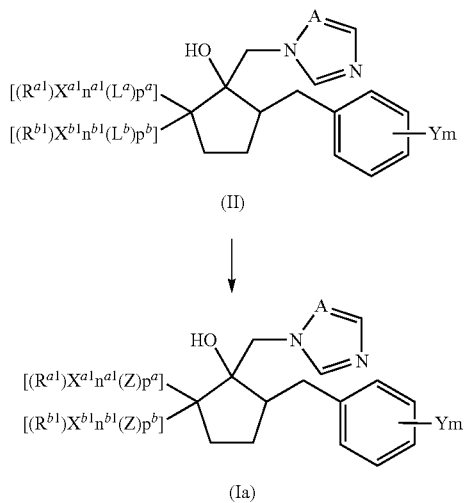

Herein, Y, m, and A are as described above. $X^{a1}$ and $X^{b1}$ have similar meanings as $X^a$ and $X^b$.

Z denotes a halogen atom. The halogen atom may for example be a fluorine atom, a chlorine atom, a bromine atom and an iodine atom. Among these, a fluorine atom, a chlorine atom and a bromine atom are preferred, with a chlorine atom being especially preferred.

Each of $R^{a1}$ and $R^{b1}$ independently denotes a hydrogen atom, or a $C_1$-$C_6$ alkyl group, a $C_2$-$C_6$ alkenyl group or a $C_2$-$C_6$ alkynyl group. The $C_1$-$C_6$ alkyl group, $C_2$-$C_6$ alkenyl group and $C_2$-$C_6$ alkynyl group may be substituted with $X^{a1}$, $X^{b1}$, $L^a$, $L^b$, and z.

Each of $L^a$ and $L^b$ denotes a halogen atom-substitutable leaving group.

$n^{a1}$ and $n^{b1}$ denote the numbers of $X^{a1}$ and $X^{b1}$ on $R^{a1}$ and $R^{b1}$. $p^a$ and $p^b$ denote the number of $L^a$ and $L^b$ on $R^{a1}$ and $R^{b1}$. "$n^{a1}+p^a$" denotes 0 or the number of hydrogen atoms substituted with $X^{a1}$ or $L^a$ or Z among the hydrogen atoms in $R^{a1}$. "$n^{b1}+p^b$" denotes 0 or the number of hydrogen atoms substituted with $X^{b1}$ or $L^b$ or Z among the hydrogen atoms in $R^{b1}$. "$p^a+p^b$" denotes an integer of 1 or more. When $n^{a1}$ denotes 2 or more then each $X^{a1}$ may be same or different. When $n^{b1}$ denotes 2 or more then each $X^{b1}$ may be same or different.

The method for substituting the leaving group with the halogen atom may for example be (a) a method for substituting a compound having a substituted sulfonyloxy group such as a p-toluenesulfonyloxy group or a methanesulfonyloxy group in a solvent with a halogenated salt, (b) a method for substituting a hydroxyl group or an alkoxy group using hydrochloric acid or hydrobromic acid, (c) a method for substituting a hydroxyl group using a halogenated phosphorus, and (d) a method for reacting a hydroxyl group with a thionyl halide.

Among substitution methods indicated as (a) to (d) described above, method indicated as (a) is preferred. Substitution method indicated as (a) is detailed below.

The reaction in the method indicated as (a) is usually conducted by mixing Compound (II) with a halogenated salt such as potassium fluoride, cesium fluoride, lithium chloride, potassium chloride, lithium bromide, magnesium bromide, and sodium iodide and the like in a solvent.

The amount of the halogenated salt employed per mole of Compound (II) is usually 0.1 to 100 moles, and preferably 0.8 to 20 moles. The reaction temperature is usually 0 to 250 degrees C., and preferably room temperature to 200 degrees C. The reaction time is usually 0.1 hour to several days, and preferably 0.2 hour to 2 days.

(3-2) Step 1B

A compound represented by Formula (IIa) employed in Step 1A (hereinafter referred to as "Compound (IIa)") is obtained by a step for reacting a compound represented by Formula (VI) ("Compound (VI)") with a substituted sulfonyl chloride represented by Formula (XV) ("Compound (XV)") ("Step 1B") (see Scheme (2) shown below). Compound (IIa) is a 5-benzyl-1-azolylmethylcyclopentanol derivative having a substituted sulfonyloxy group-substituted substituent in 2-position. Compound (VI) is a 5-benzyl-1-azolylmethylcyclopentanol derivative having a hydroxyl group-substituted substituent in 2-position.

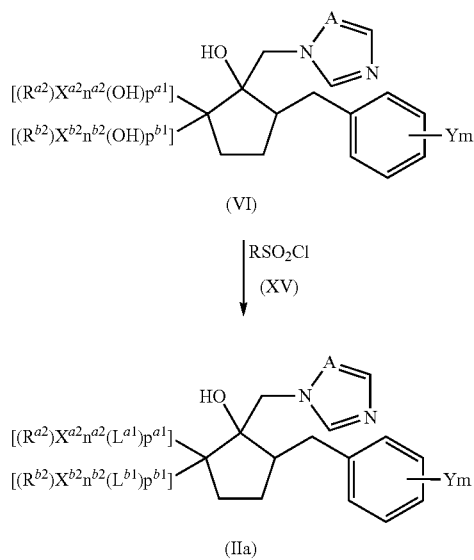

Scheme (2)
[Chem.17]

Herein, Y, m and A are as described above. $X^{a2}$ and $X^{b2}$ have similar meanings as $X^a$ and $X^b$, respectively. $L^{a1}$ denotes a halogen atom-substitutable substituted sulfonyloxy group.

Each of $R^{a2}$ and $R^{b2}$ independently denotes a hydrogen atom, or a $C_1$-$C_6$ alkyl group, a $C_2$-$C_6$ alkenyl group or a $C_2$-$C_6$ alkynyl group. The $C_1$-$C_6$ alkyl group, $C_2$-$C_6$ alkenyl group and $C_2$-$C_6$ alkynyl group may be substituted with $X^{a2}$, $X^{b2}$ or a hydroxyl group.

$n^{a2}$ and $n^{b2}$ denote the numbers of $X^{a2}$ and $X^{b2}$ on $R^{a2}$ and $R^{b2}$. $p^{a1}$ and $p^{b1}$ denote the number of the hydroxyl groups and $L^{a1}$ on $R^{a2}$ and $R^{b2}$. "$n^{a2}+p^{a1}$" denotes 0 or the number of $X^{a2}$—, hydroxyl group- or $L^{a1}$-substituted hydrogen atoms among the hydrogen atoms in $R^{a2}$. "$n^{b2}+p^{b1}$" denotes 0 or the number of $X^{b2}$—, hydroxyl group- or $L^{a1}$-substituted hydrogen atoms among the hydrogen atoms in $R^{b2}$. "$p^{a1}+p^{b1}$" denotes an integer of 1 or more. When $n^{a2}$ denotes 2 or more then each $X^{a2}$ may be same or different. When $n^{b2}$ denotes 2 or more then each $X^{b2}$ may be same or different.

R in Formula (XV) denotes a lower alkyl group, a phenyl group, or a naphthyl group. The lower alkyl group may for example be a methyl group, an ethyl group, an n-propyl group, an isopropyl group, a trifluoromethyl group and the like. The phenyl group and the naphthyl group may be substituted. The optionally substituted phenyl group and naphthyl group may for example be a 4-methylphenyl group, a 2-nitrophenyl group, and a 5-dimethylaminonaphthyl group. Among these, the methyl group and the 4-methylphenyl group are preferred.

The amount of Compound (XV) employed per mole of Compound (VI) is usually 0.5 to 10 moles, and preferably 0.8 to 5 moles. While the reaction may proceed without any added base, it is preferable to add a base for removing hydrogen chloride generated. In such a case, the amount of the base employed per mole of Compound (VI) is usually 0 to 5 moles or less (excluding 0), preferably 0.5 to 3 moles.

The base employed is not limited particularly. The base may for example be an alkaline metal hydride such as sodium hydride, potassium hydride, lithium hydride and the like; and an organic amine such as triethylamine, pyridine, 4-dimethylaminopyridine, N,N-dimethylaniline and the like.

The reaction temperature may appropriately be selected depending on the types of the solvent, the base and the like which are employed. The reaction temperature is preferably −50 degrees C. to 200 degrees C., and more preferably −20 degrees C. to 150 degrees C. The reaction time may appropriately be selected depending on the types of the solvent, the base and the like which are employed. The reaction time is preferably 0.1 hour to several days, and more preferably 0.5 hour to 1 day.

(3-3) Step 1C

Compound (VI) employed in Step 1B may be produced by a known method (for example, see Patent Literature 4). However, Compound (VIa) having a hydroxymethyl group and an alkyl group in 2-position is preferably produced using the synthetic method shown below.

First, a carbonyl compound represented by Formula (IX) shown below (hereinafter referred to as "Compound (IX)") is subjected to conversion into an oxirane to obtain an oxirane derivative represented by Formula (VIII) shown below ("Compound (VIII)"). Then, the resultant Compound (VIII) is reacted with a 1,2,4-triazole or imidazole compound represented by Formula (IV) shown below ("Compound (IV)") to obtain a compound represented by Formula (VII) shown below ("Compound (VII)"). Thereafter, the protective group of the hydroxyl group represented by G in Compound (VII) is deprotected thereby synthesizing Compound (VIa). A series of these reaction procedures ("Step IC") is represented by Scheme (3) shown below.

Scheme (3)

[Chem.18]

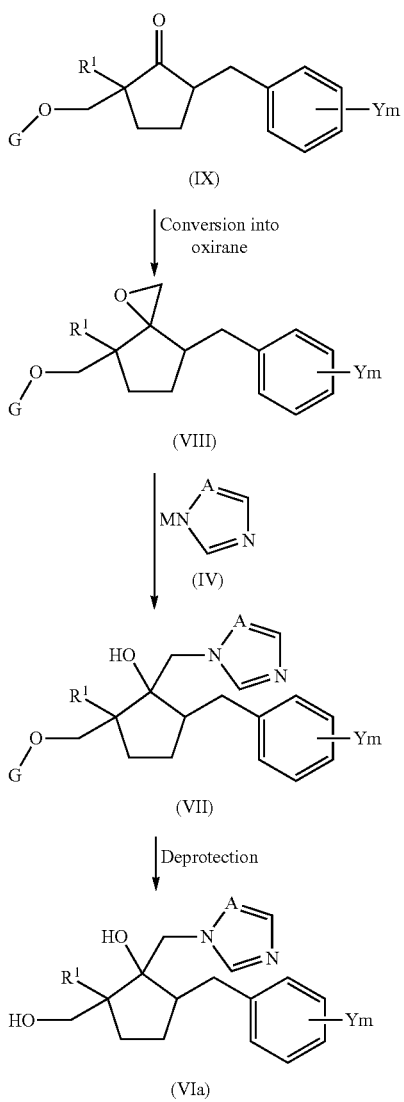

Herein, Y, m and A are as described above.

$R^1$ denotes a $C_1$-$C_6$ alkyl group, a $C_2$-$C_6$ alkenyl group or a $C_2$-$C_6$ alkynyl group. Specific examples of these $C_1$-$C_6$ alkyl group, $C_2$-$C_6$ alkenyl group and $C_2$-$C_6$ alkynyl group are the same as the specific examples in $R^a$ and $R^b$ described above, and accordingly are not specified here in detail.

G denotes a protective group, and is not limited particularly as long as Compound (VIa) can be produced from Compound (VII). The protective group can for example be an alkoxymethyl group such as a methoxymethyl group and an ethoxymethyl group, a lower alkyl group such as a t-butyl group and a methyl group as well as a substituted or unsubstituted benzyl group and the like.

M denotes a hydrogen atom or an alkaline metal.

(3-3-1) Step 1C1

A step for subjecting Compound (IX) to conversion into an oxirane to obtain Compound (VIII) (Step 1C1) in this Step 1C is described below.

First, as a first preferable synthetic method for Compound (VIII), a method involving reacting Compound (IX) with a sulfur ylide including sulfonium methylides such as dimetylsulfonium methylide and the like or sulfoxonium methylides such as dimethyl sulfoxonium methylide and the like in a solvent can be exemplified.

The sulfonium methylides and the sulfoxonium methylides employed can be produced by reacting, in a solvent, a sulfonium salt (for example, trimethylsulfonium iodide, trimethylsulfonium bromide and the like) or a sulfoxonium salt (for example, trimethylsulfoxonium iodide, trimethylsulfoxonium bromide and the like) with a base.

The amount of such a sulfonium methylide and sulfoxonium methylide per mole of Compound (IX) described above is preferably 0.5 to 5 moles, and more preferably 0.8 to 2 moles.

The solvent employed is not limited particularly. The solvent can for example be dimethyl sulfoxide, amides such as N-methylpyrrolidone, N,N-dimethylformamide and the like, ethers such as tetrahydrofuran, dioxane and the like, as well as a solvent mixture thereof.

The base employed for producing sulfonium methylides and sulfoxonium methylides is not limited particularly. The base can for example be a metal hydride such as sodium hydride and the like, an alkoxide of an alkaline metal such as sodium methoxide, sodium ethoxide, sodium t-butoxide, potassium t-butoxide and the like.

The reaction temperature and the reaction time may appropriately be selected depending on the types of the solvent, Compound (IX), sulfonium salt or sulfoxonium salt, base and the like which are employed. The reaction temperature is preferably −100 degrees C. to 200 degrees C., and more preferably −50 degrees C. to 150 degrees C. The reaction time is preferably 0.1 hour to several days, and more preferably 0.5 hour to 2 days.

Next, as a second synthetic method for Compound (VIII), a method in which Compound (IX) is reacted with samarium iodide and diiodomethane in a solvent and subsequently treated with a base is described below.

The base is not limited particularly. The base may for example be sodium hydroxide. The samarium iodide employed can be produced by reacting a metal samarium with 1,2-diiodoethane or diiodomethane in an anhydrous solvent. The solvent employed is not limited particularly and may for example be an ether such as tetrahydrofuran and the like.

While the amount of the base per mole of Compound (IX) is not limited particularly, it is preferably 0.5 to 10 moles in usual cases, and more preferably 0.8 to 6 moles. When treating with the base, an aqueous solution of sodium hydroxide may for example be employed since no anhydrous system is required.

The reaction temperature and the reaction time may appropriately be selected depending on the types of the solvent, Compound (IX), base and the like which are employed. The reaction temperature is preferably −100 degrees C. to 150 degrees C., and more preferably −50 degrees C. to 100 degrees C. The reaction time is preferably 0.1 hour to several days, and more preferably 0.5 hour to 2 days.

(3-3-2) Step 1C2

Next, a step for reacting Compound (VIII) and Compound (IV) to obtain Compound (VII) (Step 1C2) in this Step 1C is described below.

Compound (VII) is produced by mixing Compound (VIII) with Compound (IV) in a solvent to form a carbon-nitrogen bond between the carbon atom constituting an oxirane ring in an oxirane derivative (Compound (VIII)) and the nitrogen atom in 1,2,4-triazole or imidazole.

While the solvent employed is not limited particularly, and can for example be amides such as N-methylpyrrolidone and N,N-dimethylformamide and the like.

The amount of Compound (IV) employed per mole of Compound (VIII) is preferably 0.5 to 10 moles in usual cases, and more preferably 0.8 to 5 moles. A base may be added if necessary. The amount of the base employed per mole of Compound (IV) is preferably 0 to 5 moles (excluding 0) in usual cases, and more preferably 0.5 to 2 moles.

The reaction temperature may appropriately be selected depending on the types of the solvent, the base and the like which are employed. The reaction temperature is preferably 0 degrees C. to 250 degrees C., and more preferably 10 degrees C. to 150 degrees C. The reaction time may appropriately be selected depending on the types of the solvent, the base and the like which are employed. The reaction time is preferably 0.1 hour to several days, and more preferably 0.5 hour to 2 days.

It is possible to produce Compound (VII) by producing Compound (VIII) and then reacting it stepwise with Compound (IV) as described above. Nevertheless, when the reaction for conversion into an oxirane is conducted alone in the first synthetic method described above, a by-product such as an oxetane derivative is produced, resulting in a reduced yield. In order to avoid this reduced yield, conversion into an azole may be conducted while allowing Compound (VIII) to be produced (see Scheme (4) shown below).

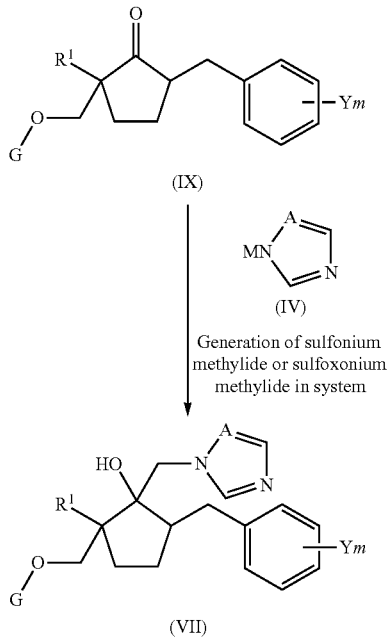

Scheme (4)

[Chem.19]

Herein, Y, m, A, $R^1$, G and M are as described above.

In such a case, Compound (IX) and Compound (IV) described above are dissolved in a polar solvent having an amide bond, or dimethyl sulfoxide or a solvent mixture of an alcohol with a polar solvent. Then, to this, a trimethylsulfonium salt or a trimethylsulfoxonium salt and a base are added intermittently to produce sulfonium methylides such as dimethylsulfonium methylide and the like or sulfoxonium methylides such as dimethyl sulfoxonium methylide and the like in the reaction system, thereby effecting the conversion into an azole while allowing Compound (VIII) to be produced.

The solvent employed here is not limited particularly. As a preferable solvent, a polar solvent having an amide bond such as N-methylpyrrolidone and N,N-dimethylformamide and the like, or dimethyl sulfoxide, or a solvent mixture of a polar solvent with an alcohol can be exemplified. The alcohol may be t-butanol.

The base employed for producing sulfonium methylides and sulfoxonium methylides are not limited particularly. The base can for example be a metal hydride such as sodium hydride and the like, an alkoxide of an alkaline metal such as sodium methoxide, sodium ethoxide, sodium t-butoxide, potassium t-butoxide and the like. In addition, an alkaline metal salt of 1,2,4-triazole or imidazole may also be used.

The reaction temperature may appropriately be selected depending on the types of the solvent, Compound (IX), sulfonium salt or sulfoxonium salt, base and the like which are employed. The reaction temperature is preferably −100 degrees C. to 250 degrees C., and more preferably −50 degrees C. to 200 degrees C. The reaction time may appropriately be selected depending on the types of the solvent, Compound (IX), sulfonium salt or sulfoxonium salt, base and the like which are employed. The reaction time is preferably 0.1 hour to several days, more preferably 0.5 hour to 2 days.

The number of times when a trimethyl sulfonium halide or a trimethyl sulfonium halide and a base are added intermittently is not limited particularly as long as it is the number of times allowing a predetermined aim to be accomplished. A preferred number of times may usually be 2 to 20 times, with 3 to 15 times being more preferable. The total amount of a trimethylsulfonium salt or a trimethylsulfoxonium salt employed per mole of Compound (IX) is preferably 0.5 to 5 moles, more preferably 0.8 to 2 moles.

The amount of Compound (IV) employed per mole of Compound (IX) is preferably 0.5 to 10 moles in usual cases, and more preferably 0.8 to 5 moles. It is preferable to use Compound (IV) in which M is an alkaline metal salt.

For details of the steps for conducting the conversion into an azole while allowing the oxirane derivative to be produced in the production of the azolylmethylcycloalkanol derivative, see Patent Literature 5.

(3-3-3) Step 1C3

Next, a step for deprotecting the protective group of Compound (VII) to obtain Compound (VIa) (Step 1C3) in this Step 1C is described below.

Although a preferred condition differs depending on the type of the protective group, in the cases, for example, of using an alkoxymethyl group such as a methoxymethyl group or an ethoxyethyl group or a lower alkyl group such as a t-butyl group or a methyl group, the deprotection is conducted preferably in a solvent under an acidic condition involving hydrogen chloride or sulfuric acid and the like.

The acid employed here is preferably a halogenated hydrogen such as hydrogen chloride or an inorganic acid such as sulfuric acid. While the amount employed is not limited particularly, the amount of the acid employed per mole of Compound (VII) is usually 0.5 to 100 moles, and preferably 0.8 to 20 moles.

The reaction temperature is preferably 0 degrees C. to 200 degrees C. in usual cases, and more preferably room temperature to 100 degrees C. The reaction time is preferably 0.1 hour to several days in usual cases, more preferably 0.5 hour to 2 days.

(3-4) Step 1D

Compound (XII) employed in Step 1C can preferably be synthesized by the method shown below.

Thus, a keto ester compound represented by Formula (XII) shown below (hereinafter referred to as "Compound (XII)") is hydroxymethylated to obtain a compound represented by Formula (XI) shown below ("Compound (XI)"). Then, a protective group such as a methoxymethyl group or a t-butyl group and the like is introduced into the hydroxyl group in Compound (XI) to effect derivatization into a compound represented by Formula (X) shown below ("Compound (X)"). Thereafter, Compound (X) is hydrolyzed/decarbonated to obtain a carbonyl compound represented by Formula (XI) shown below ("Compound (XI)"). A series of these reaction procedures ("Step 1D") is represented by Scheme (5) shown below.

Scheme (5)

[Chem.20]

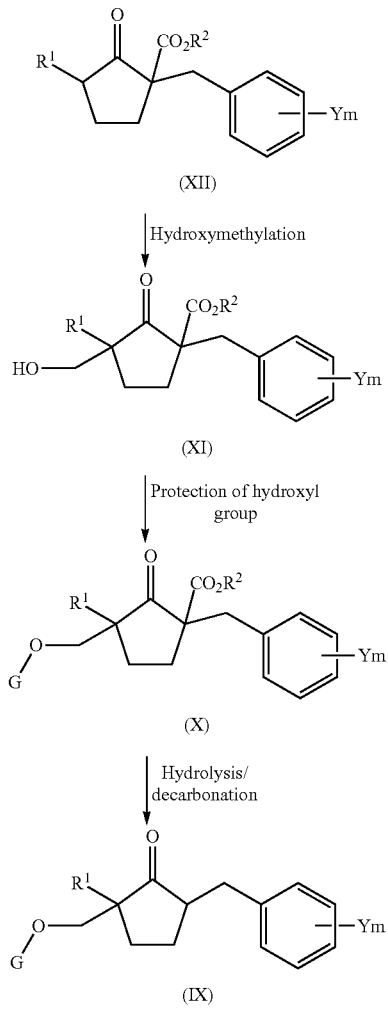

Herein, Y, m, $R^1$ and G are as described above.

$R^2$ denotes a C1-C4 alkyl group. The specific examples of the alkyl groups in $R^2$ are the same as the specific examples in $R^a$ and $R^b$ described above, and accordingly are not specified here in detail.

(3-4-1) Step 1D1

In this Step 1D, in the step for obtaining Compound (XI) by hydroxymethylating Compound (XII), a method involving a reaction with formaldehyde in the presence of a base in a solvent may be employed.

The amount of formaldehyde employed per mole of Compound (XII) is usually 0.5 to 20 moles, and preferably 0.8 to 10 moles.

The base can for example be, but not limited to, a carbonate of an alkaline metal such as sodium carbonate, potassium carbonate and the like as well as a hydroxide of an alkaline metal such as sodium hydroxide and the like. The amount of the base employed per mole of Compound (XII) is usually 0.1 to 10 moles, and preferably 0.2 to 5 moles.

The reaction temperature is preferably 0 degrees C. to 250 degrees C. in usual cases, and more preferably 0 to 100 degrees C. The reaction time is preferably 0.1 hour to several days in usual cases, and more preferably 0.5 hour to 2 days.

Compound (XII) employed here may be produced by a known method (for example, the method disclosed in Patent Literature 1).

(3-4-2) Step 1D2

Next, a step for introducing a protective group into the hydroxyl group in Compound (XI) to obtain Compound (X) (Step 1D2) in this Step 1D is described below.

While the protective group for protecting the hydroxyl group is not limited particularly, those employed preferably are an alkoxymethyl group such as a methoxymethyl group and an ethoxymethyl group, and a lower alkyl group such as a t-butyl group and the like. Introduction of these protective group is conducted preferably by (a) an acetal exchange of the hydroxyl group in Compound (XII) using a formaldehyde dialkylacetal in the case of introduction of an alkoxymethyl group. (b) Addition of the hydroxyl group in Compound (XII) using isobutene is utilized preferably in the case of introduction of a t-butyl group.

First, the case (a) mentioned above is described below.

As an acid, an inorganic acid such as hydrochloric acid, phosphoric acid (including a compound allowing an acidic group to be generated by addition of an alcohol or water, such as diphosphorus pentoxide) and sulfuric acid, and an organic acid such as p-toluenesulfonic acid and the like are employed. In the presence of such an acid, a formaldehyde dialkylacetal is employed preferably in a solvent or in a solvent-free system. It is further preferred to add a compound allowing any generated alcohol to be removed, such as diphosphorus pentoxide.

The amount of the formaldehyde dialkylacetal employed per mole of Compound (XI) is usually 0.5 to 50 moles, and preferably 0.8 to 10 moles. The amount of the acid employed per mole of Compound (XI) is usually 0.01 to 10 moles, and preferably 0.05 to 5 moles.

The reaction temperature is preferably 0 degrees C. to 250 degrees C. in usual cases, and more preferably 0 degrees C. to 150 degrees C. The reaction time is preferably 0.1 hour to several days in usual cases, and more preferably 0.5 hour to 2 days.

In the case (b) mentioned above, it is preferred to conduct a reaction with isobutene in a solvent in the presence of an inorganic acid such as hydrochloric acid, phosphoric acid and sulfuric acid and the like, or an organic acid such as p-toluenesulfonic acid and trifluoroacetic acid and the like.

The amount of isobutene employed per mole of Compound (XI) is usually 0.5 to 100 moles, and preferably 0.8 to 20 moles. The amount of the acid employed per mole of Compound (XI) is usually 0.01 to 10 moles, and preferably 0.05 to 5 moles.

The reaction temperature is preferably 0 degrees C. to 200 degrees C. in usual cases, and more preferably 0 degrees C. to 100 degrees C. The reaction time is preferably 0.1 hour to several days in usual cases, and more preferably 0.5 hour to 2 days.

(3-4-3) Step 1D3

Next, a step for hydrolyzing/decarbonating Compound (X) to obtain Compound (IX) (Step 1D3) in this Step 1D is described below.

This reaction is conducted preferably in the presence of a base in a solvent. The base employed usually includes an alkaline metal base such as sodium hydroxide, potassium hydroxide and the like. The amount of base employed per mole of Compound (X) is usually 0.1 to 50 moles, and preferably 0.2 to 20 moles.

The solvent may usually be water, as well as water combined with an alcohol and the like, a solvent mixture consisting of solvents which do not form a homogenous layer with each other (such as water-toluene) (in such a case it may sometimes be preferable to use a phase transfer catalyst, such as a customary quaternary ammonium salt, in the reaction system).

The reaction temperature is preferably 0 degrees C. to reflux temperature in usual cases, and more preferably room temperature to reflux temperature. The reaction time is preferably 0.1 hour to several days in usual cases, and more preferably 0.5 hour to 24 hours.

(4) Second Method for Producing Compound (I)

(4-1) Step 2A

Another embodiment of the production method according to the invention is described. This embodiment comprises a step for subjecting a carbonyl compound represented by Formula (V) shown below to conversion into an oxirane thereby obtaining an oxirane derivative represented by Formula (III) shown below which is then reacted with a compound represented by Formula (IV) shown below to obtain Compound (I) (Step 2A) (see Scheme (6) shown below). Hereinafter, the carbonyl compound represented by Formula (V) is referred to as "Compound (V)", while the oxirane derivative represented by Formula (III) is referred to as "Compound (III)".

Scheme (6)

[Chem.21]

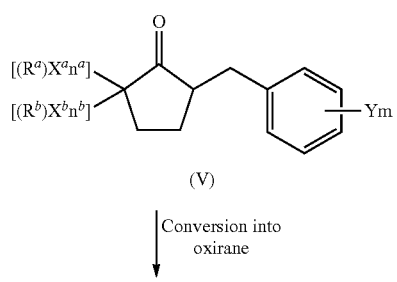

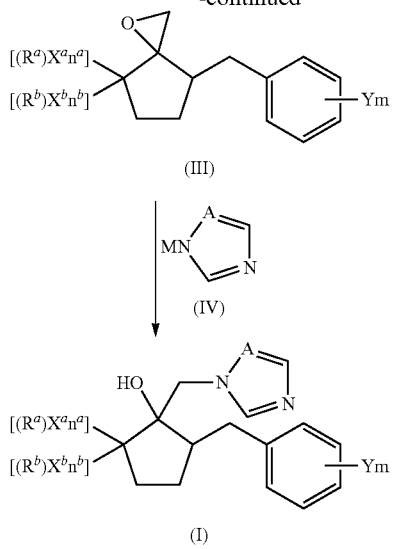

Herein, $R^a$, $R^b$, $X^a$, $X^b$, $n^a$, $n^b$, Y, m, A and M are as described above.

(4-1-1) Step 2A1

First, a step for converting Compound (V) into an oxirane to obtain Compound (III) (Step 2A1) is described below.

As a first preferable synthetic method for Compound (III), a method involving reacting Compound (V) with a sulfur ylide including sulfonium methylides such as dimetylsulfonium methylide and the like or sulfoxonium methylides such as dimethyl sulfoxonium methylide and the like in a solvent can be exemplified.

The sulfonium methylides or the sulfoxonium methylides can be produced by reacting, in a solvent, a sulfonium salt (for example, trimethylsulfonium iodide, trimethylsulfonium bromide and the like) or a sulfoxonium salt (for example, trimethylsulfoxonium iodide, trimethylsulfoxonium bromide and the like) with a base. While the base is not limited particularly, those employed preferably include a metal hydride such as sodium hydride and the like, an alkoxide of an alkaline metal such as sodium methoxide, sodium ethoxide, sodium t-butoxide, potassium t-butoxide and the like.

The amount of such a sulfonium methylide and sulfoxonium methylide per mole of Compound (V) is 0.5 to 5 moles, and preferably 0.8 to 2 moles.

While the solvent employed is not limited particularly, it may for example be dimethyl sulfoxide, amides such as N-methylpyrrolidone and N,N-dimethylformamide and the like, ethers such as tetrahydrofuran, dioxane and the like, as well as a solvent mixture thereof.

While the reaction temperature may appropriately be selected depending on the types of the solvent, Compound (V), sulfonium salt or sulfoxonium salt, base and the like which are employed, it is preferably −100 degrees C. to 200 degrees C., and more preferably −50 degrees C. to 150 degrees C. While the reaction time may appropriately be selected depending on the types of the solvent, Compound (V), sulfonium salt or sulfoxonium salt, base and the like which are employed, it is preferably 0.1 hour to several days, and more preferably 0.5 hour to 2 days.

As a second preferable synthetic method for Compound (III), a method involving reacting Compound (V) with samarium iodide and diiodomethane in a solvent and then treating it with a base can be exemplified. The base employed is not limited particularly and may for example be sodium hydroxide.

The amount of samarium iodide per mole of Compound (V) is usually 0.5 to 10 moles, and preferably 1 to 6 moles. The amount of diiodomethane per mole of Compound (V) is usually 0.5 to 10 moles, and preferably 0.8 to 5 moles. The samarium iodide can be produced by reacting a metal samarium with 1,2-diiodoethane or diiodomethane in an anhydrous solvent.

While the amount of the base per mole of Compound (V) is not limited particularly, it is preferably 0.5 to 10 moles in usual cases, and more preferably 0.8 to 6 moles. When treating with the base, an aqueous solution of sodium hydroxide may for example be employed since no anhydrous system is required.

The reaction temperature and the reaction time may appropriately be selected depending on the types of the solvent, Compound (V), base and the like which are employed. The reaction temperature is preferably −100 degrees C. to 150 degrees C., and more preferably −50 degrees C. to 100 degrees C. The reaction time is preferably 0.1 hour to several days, and more preferably 0.5 hour to 2 days.

(4-2-2) Step 2A2

Next, a step for obtaining Compound (I) from Compound (III) and Compound (IV) (Step 2A2) is described below.

Compound (I) is produced by mixing Compound (III) with Compound (IV) in a solvent to form a carbon-nitrogen bond between the carbon atom constituting an oxirane ring in an oxirane derivative and the nitrogen atom in 1,2,4-triazole or imidazole.

While the solvent employed is not limited particularly, it can for example be amides such as N-methylpyrrolidone and N,N-dimethylformamide and the like.

The amount of Compound (IV) employed per mole of Compound (III) is preferably 0.5 to 10 moles in usual cases, and more preferably 0.8 to 5 moles. A base may be added if necessary. The amount of the base employed per mole of Compound (IV) is preferably 0 to 5 moles (excluding 0) in usual cases, and more preferably 0.5 to 2 moles.

The reaction temperature may appropriately be selected depending on the types of the solvent, the base and the like which are employed. The reaction temperature is preferably 0 degrees C. to 250 degrees C., and more preferably 10 degrees C. to 150 degrees C. The reaction time may appropriately be selected depending on the types of the solvent, the base and the like which are employed. The reaction time is preferably 0.1 hour to several days, and more preferably 0.5 hour to 2 days.

(4-2) Step 2B

While for Compound (V) employed in Step 2A it is possible to use a compound which can be synthesized by a conventional technology, Compound (Va) is preferably produced by the following synthetic method.

First, in the presence of a base, Compound (XII) is reacted with a halogenated compound represented by Formula (XIV) shown below (hereinafter referred to as "Compound (XIV)") to obtain a keto ester compound represented by Formula (XIII) (referred to as "Compound (XIII)"). Subsequently, Compound (XIII) thus obtained is hydrolyzed/decarbonated to obtain Compound (Va). A series of these reaction procedures ("Step 2B") is represented by Scheme (7) shown below.

Scheme (7)

[Chem.22]

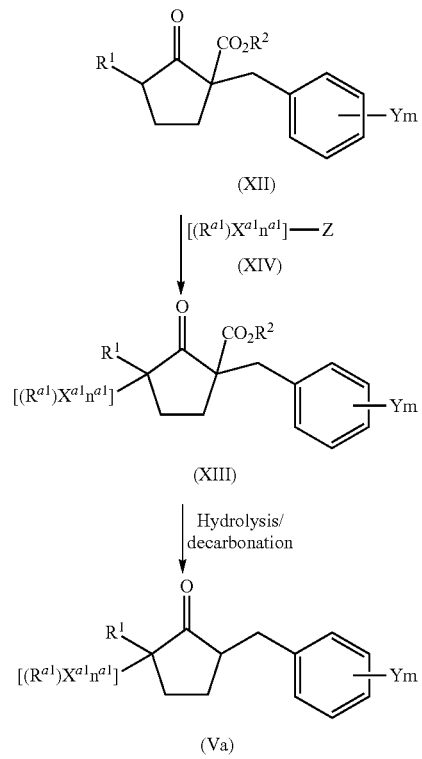

Herein, $R^1$, $R^2$, Y and m are as described above. $R^{a1}$, $X^{a1}$ and $n^{a1}$ have similar meanings as $R^a$, $X^a$ and $n^a$, respectively.

First, a step for reacting Compound (XII) in the presence of a base with Compound (XIX) to obtain Compound (XIII) (Step 2B1) is described below.

This reaction is conducted preferably in a solvent. The base is not limited particularly, and includes alkaline metal hydrides such as sodium hydride and the like, and alkaline metal carbonates such as sodium carbonate, potassium carbonate and the like. The amount of the base per mole of Compound (XII) is preferably 0.5 to 5 moles, and more preferably 0.8 to 2 moles.

The amount of Compound (XIV) per mole of Compound (XII) is preferably 0.5 to 10 moles, and more preferably 0.8 to 5 moles.

While the reaction temperature may appropriately be selected depending on the types of the solvent, Compound (XII), Compound (XIV), base and the like which are employed, it is preferably 0 degrees C. to 250 degrees C., and more preferably room temperature to 150 degrees C. While the reaction time may appropriately be selected depending on the types of the solvent, Compound (XII), Compound (XIV), base and the like which are employed, it is preferably 0.1 hour to several days, and more preferably 0.5 hour to 24 hours.

(4-2-2) Step 2B2

Next, a step for hydrolyzing/decarbonating Compound (XIII) (Step 2B2) is described below.

This reaction can be conducted in a solvent under both of a basic condition and an acidic condition.

When conducting hydrolysis under the basic condition, the base is usually an alkaline metal base such as sodium hydroxide, potassium hydroxide and the like. The solvent is usually water, as well as water combined with alcohols.

When conducting hydrolysis under the acidic condition, the acid catalyst is an inorganic acid such as hydrochloric acid, hydrobromic acid, sulfuric acid and the like. The solvent is usually water, or water combined with an organic acid such as acetic acid.

The reaction temperature is preferably 0 degrees C. to reflux temperature in usual cases, and more preferably room temperature to reflux temperature. The reaction time is usually 0.1 hour to several days, and preferably 0.5 hour to 24 hours.

(5) Third Method for Producing Compound (I)

(5-1) Step 3A

Another embodiment of the production method according to the invention is described. This embodiment comprises a step for reacting a compound represented by Formula (VIb) shown below ("Compound VIb") with a substituted sulfonyl chloride group represented by Formula (XV) shown below ("Compound (XV)") to obtain an oxetane compound represented by Formula (XVI) shown below ("Compound (XVI)"). Also included is a step for subjecting Compound (XVI) to ring opening using any halogenic acid to obtain Compound (Ib) (Step 3A; see Scheme (8) shown below). Compound (VIb) is a 5-benzyl-1-azolylmethylcyclopentanol derivative having a hydroxyl group-substituted substituent in 2-position, and corresponds to Compound (VI) wherein $R^{a1}=R^a$, $X^{a1}=X^a$, $n^{a1}=n^a$, $p^{a1}=0$, $R^{b2}$=methyl group, $n^{b2}=0$, and $p^{b1}=1$.

Scheme (8)

[Chem.23]

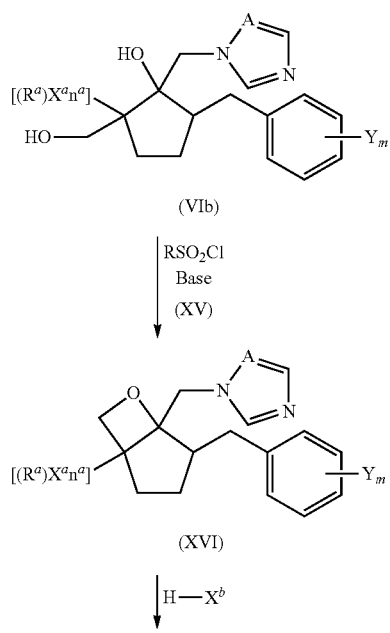

Herein, $R^a$, $X^a$, $n^a$, R, Y, m and $X^b$ are as described above.

(5-1-1) Step 3A1

First, a step for subjecting Compound (VIb) to ring closing to obtain an oxetane compound (XVI) (Step 3A1) is described below.

As a preferable synthetic method for Compound (XVI), a method for reacting Compound (VIb) in the presence of a sulfonyl chloride and an excessive amount of base in a solvent can be exemplified.

The sulfonyl chloride may for example be p-toluenesulfonyl chloride and methane-sulfonyl chloride and the like. Among these, p-toluenesulfonyl chloride is employed preferably. While the base is not limited particularly, those employed preferably include a metal hydride such as sodium hydride and the like, an alkoxide of an alkaline metal such as sodium methoxide, sodium ethoxide, sodium t-butoxide, potassium t-butoxide and the like.

The amount of the sulfonyl chloride per mole of Compound (VIb) is preferably 0.5 to 5 moles, and more preferably 0.8 to 2 moles. The amount of the base is preferably 1.5 to 5 moles, and more preferably 1.8 to 3 moles.

While the solvent is not limited particularly, it includes amides such as N-methylpyrrolidone and N,N-dimethylformamide and the like, ethers such as tetrahydrofuran and dioxane and the like, or dimethyl sulfoxide as well as solvent mixtures thereof.

While the reaction temperature may appropriately be selected depending on the types of the solvent, Compound (VIb), sulfonyl chloride, base and the like which are employed, it is preferably −100 degrees C. to 200 degrees C., and more preferably −50 degrees C. to 150 degrees C. While the reaction time may appropriately be selected depending on the types of the solvent, Compound (VIb), sulfonyl chloride, base and the like which are employed, it is preferably 0.1 hour to several days, and more preferably 0.5 hour to 2 days.

(5-1-2) Step 3A2

Next, a step for obtaining Compound (Ib) from Compound (XVI) (Step 3A2) is described below.

Compound (Ib) can be produced preferably by mixing Compound (XVI) with Compound H-$X^b$ in a solvent to effect ring opening of the oxetane ring possessed by Compound (XVI) thereby producing a halogenated methyl group and a tertiary hydroxyl group.

H-$X^b$ denotes a halogenic acid, such as hydrogen chloride, hydrogen bromide, hydrogen iodide and the like. The halogenic acid may be introduced also as a gas, and it may be added as being dissolved in an organic solvent solution. It is possible to add a halogenic acid salt and an acid irrelevant to the halogenic acid salt (such as toluene-sulfonic acid, methanesulfonic acid and the like) thereby obtaining Compound (Ib) from Compound (XVI).

While the solvent employed is not limited particularly, it may for example be amides such as N-methylpyrrolidone and N,N-dimethylformamide and the like, alcohols such as methanol and ethanol, and ethers such as tetrahydrofuran, dioxane and the like.

The amount of Compound H-$X^b$ employed per mole of Compound (XVI) is usually 0.5 to 50 moles, and preferably 1 to 20 moles.

While the reaction temperature may appropriately be selected depending on the types of the solvent, base and the like which are employed, it is preferably −20 degrees C. to 250 degrees C., and more preferably −10 degrees C. to 150 degrees C. While the reaction time may appropriately be selected depending on the types of the solvent, base and the like which are employed, it is preferably 0.1 hour to several days, and more preferably 0.5 hour to 2 days.

Compound (VIb) employed in Step 3A1 can be synthesized by the method similar to Step 1C and Step 1D described in the first production method. The entire steps of the third production method involving the step for synthesizing Compound (VIb) is indicated in Scheme (9) shown below.

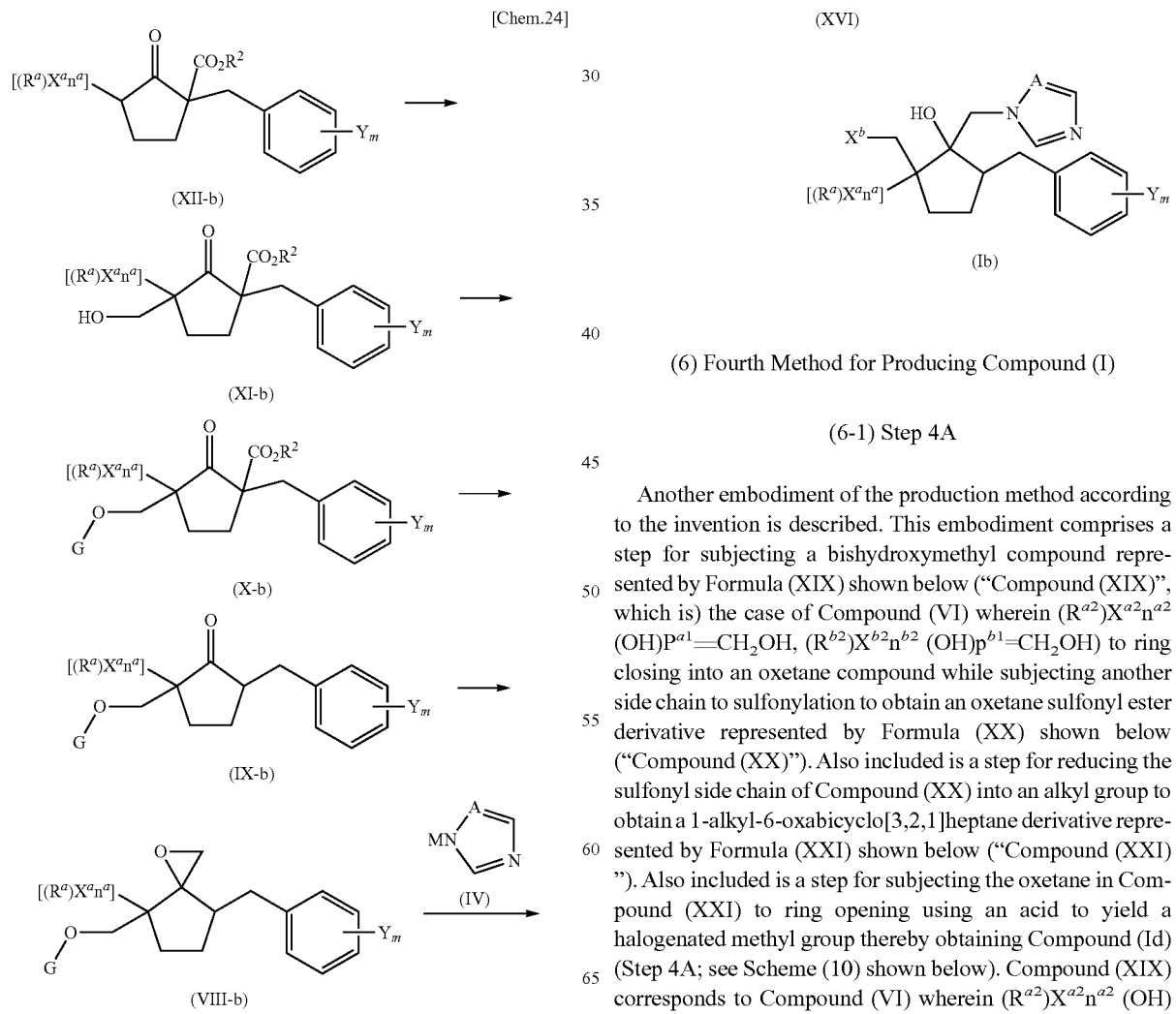

(6) Fourth Method for Producing Compound (I)

(6-1) Step 4A

Another embodiment of the production method according to the invention is described. This embodiment comprises a step for subjecting a bishydroxymethyl compound represented by Formula (XIX) shown below ("Compound (XIX)", which is) the case of Compound (VI) wherein $(R^{a2})X^{a2}n^{a2}$ $(OH)P^{a1}$=$CH_2OH$, $(R^{b2})X^{b2}n^{b2}$ $(OH)p^{b1}$=$CH_2OH$) to ring closing into an oxetane compound while subjecting another side chain to sulfonylation to obtain an oxetane sulfonyl ester derivative represented by Formula (XX) shown below ("Compound (XX)"). Also included is a step for reducing the sulfonyl side chain of Compound (XX) into an alkyl group to obtain a 1-alkyl-6-oxabicyclo[3,2,1]heptane derivative represented by Formula (XXI) shown below ("Compound (XXI)"). Also included is a step for subjecting the oxetane in Compound (XXI) to ring opening using an acid to yield a halogenated methyl group thereby obtaining Compound (Id) (Step 4A; see Scheme (10) shown below). Compound (XIX) corresponds to Compound (VI) wherein $(R^{a2})X^{a2}n^{a2}$ $(OH)p^{a1}$=$CH_2OH$, $(R^{b2})X^{b2}n^{b2}$ $(OH)p^{b1}$=$CH_2OH$.

Scheme (10)

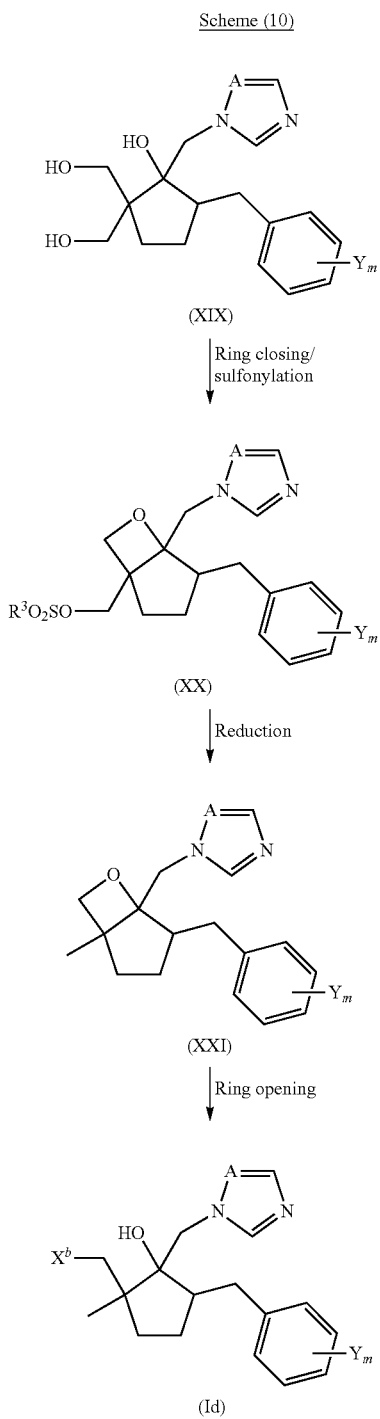

Herein, Y, m, A and $X^b$ are as described above.

$R^3$ denotes a lower alkyl group, a phenyl group or a naphthyl group. The lower alkyl group may for example be a methyl group, an ethyl group, an n-propyl group, an isopropyl group, and a trifluoromethyl group. The phenyl group and the naphthyl group may be substituted. The phenyl group and the naphthyl group which may be substituted may for example be a 4-methylphenyl group, a 2-nitrophenyl group and a 5-dimethylaminonaphthyl group. Among these, the methyl group or the 4-methylphenyl group is employed preferably.

(6-1-1) Step 4A1

First, a step for converting Compound (XIX) into an oxetane while sulfonylating it to obtain Compound (XX) (Step 4A1) is described below.

As a preferable synthetic method for Compound (XX), a method involving reacting Compound (XIX) in the presence of 2 equivalents or more of a sulfonyl chloride and an excessive amount of a base in a solvent can be exemplified The sulfonyl chloride may for example be p-toluenesulfonyl chloride, methane-sulfonyl chloride and the like. Among these, p-toluenesulfonyl chloride is employed preferably. While the base is not limited particularly, those employed preferably include a metal hydride such as sodium hydride and the like, and an alkoxide of an alkaline metal such as sodium methoxide, sodium ethoxide, sodium t-butoxide, potassium t-butoxide and the like.

The amount of the sulfonyl chloride per mole of Compound (XIX) is preferably 1.8 to 10 moles, and more preferably 2 to 5 moles. The amount of the base is preferably 2.5 to 10 moles, and more preferably 2.8 to 6 moles.

While the solvent is not limited particularly, it includes amides such as N-methylpyrrolidone and N,N-dimethylformamide and the like, ethers such as tetrahydrofuran and dioxane and the like, or dimethyl sulfoxide as well as solvent mixtures thereof.

While the reaction temperature may appropriately be selected depending on the types of the solvent, Compound (XIX), sulfonyl chloride, base and the like which are employed, it is preferably −100 degrees C. to 200 degrees C., and more preferably −50 degrees C. to 150 degrees C. While the reaction time may appropriately be selected depending on the types of the solvent, Compound (XIX), sulfonyl chloride, base and the like which are employed, it is preferably 0.1 hour to several days, and more preferably 0.5 hour to 2 days.

(6-1-2) Step 4A2

Next, a step for obtaining Compound (XXI) from Compound (XX) (Step 4A2) is described below.

In a suitable solvent, a variety of general reducing condition can be employed to reduce the sulfonyloxy group in Compound (XX) thereby obtaining Compound (XXI).

The reducing agent can for example be a metal, a hydride type reducing agent, a hydrogen/catalytic hydrogenation catalyst and the like. For example, the metal includes an iron powder, a zinc powder, a combination of a zinc powder and NaI and the like. The hydride type reducing agent includes sodium borohydride, lithium borohydride, lithium aluminum hydride and the like. The catalytic hydrogenation catalyst includes a palladium/carbon, a palladium hydroxide/carbon, a platinum/carbon, a Raney nickel and the like. Among these, the metal powder is employed preferably, with a combination of the zinc powder and NaI being more preferred.

The solvent is not limited particularly, and may appropriately be selected depending on the type of the reducing agent. The solvent may be an ether based solvent such as tetrahydrofuran, diethyl ether and the like, an alcohol based solvent such as methanol, ethanol and the like, or a protic solvent having a high polar ratio such as dimethyl sulfoxide, dimethyl formamide and the like.

The amount of the reducing agent employed per mole of Compound (XX) is usually 0.5 to 50 moles, and preferably 1 to 20 moles.

While the reaction temperature may appropriately be selected depending on the types of the solvent, base and the like which are employed, it is preferably −20 degrees C. to 250 degrees C., and more preferably −10 degrees C. to 150 degrees C. While the reaction time may appropriately be selected depending on the types of the solvent, base and the like which are employed, it is preferably 0.1 hour to several days, and more preferably 0.5 hour to 3 days.

(6-1-3) Step 4A3

Next, a step for obtaining Compound (Id) from Compound (XXI) (Step 4A3) is described below.

In this step, Compound (Id) can be produced by mixing Compound (XXI) with Compound H-$X^b$ in a solvent to effect ring opening of the oxetane ring possessed by Compound (XXI) thereby producing a halogenated methyl group and a tertiary hydroxyl group.

H-$X^b$ denotes a halogenic acid, such as hydrogen chloride, hydrogen bromide, hydrogen iodide and the like. The halogenic acid may be introduced also as a gas, and it may be added as being dissolved in an organic solvent solution. It is possible to add an acid irrelevant to the halogenic acid salt (such as toluenesulfonic acid, methane-sulfonic acid and the like) thereby obtaining Compound (Id) from Compound (XXI).

While the solvent employed is not limited particularly, it may for example be amides such as N-methylpyrrolidone and N,N-dimethylformamide and the like, alcohols such as methanol and ethanol, and ethers such as tetrahydrofuran, dioxane and the like.

The amount of Compound H-$X^b$ employed per mole of Compound (XXI) is usually 0.5 to 50 moles, and preferably 1 to 20 moles.

While the reaction temperature may appropriately be selected depending on the types of the solvent, H-$X^b$ and the like which are employed, it is preferably −20 degrees C. to 250 degrees C., and more preferably −10 degrees C. to 150 degrees C. While the reaction time may appropriately be selected depending on the types of the solvent, base and the like which are employed, it is preferably 0.1 hour to several days, and more preferably 0.5 hour to 2 days.

(6-2) Step 4B

Compound (XIX) employed in Step 4A may be produced preferably by the following method.

First, a carbonyl compound represented by Formula (XXII) shown below (hereinafter referred to as "Compound (XXII)") is subjected to conversion into an oxirane to obtain an oxirane derivative represented by Formula (XXIII) shown below ("Compound (XXIII)"). Then, the resultant Compound (XXIII) is reacted with a 1,2,4-triazole or imidazole compound represented by Formula (IV) shown below ("Compound (IV)") to obtain a compound represented by Formula (XXIV) shown below ("Compound (XXIV)"). Thereafter, the protective group of the hydroxyl group represented by G in Compound (XXIV) is deprotected thereby synthesizing Compound (XIX). A series of these reaction procedures ("Step 4B") is represented by Scheme (11) shown below.

Scheme (11)

[Chem.26]

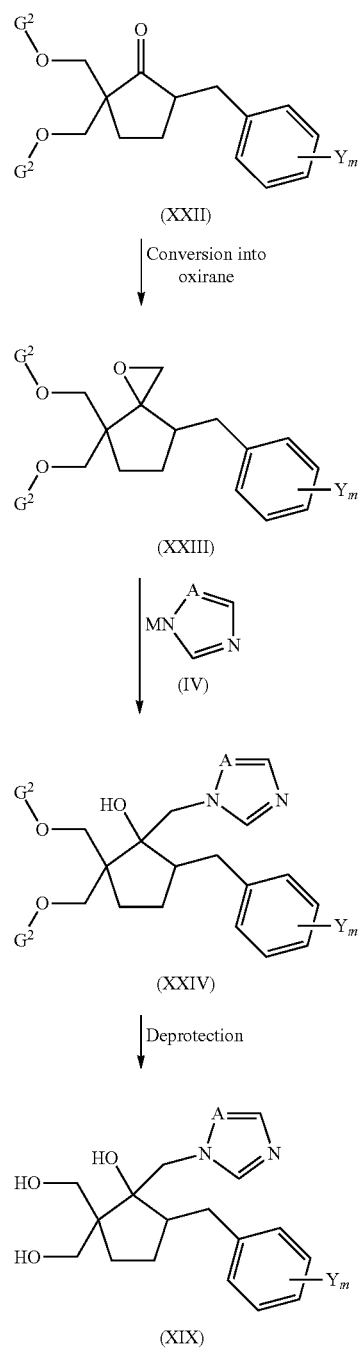

Herein, Y, m, A and M are as described above.

$G^2$ denotes a protective group, and is not limited particularly as long as Compound (XIX) can be produced from Compound (XXIV). The protective group can for example be an alkoxymethyl group such as a methoxymethyl group and an ethoxymethyl group, a lower alkyl group such as a t-butyl group and a methyl group as well as a substituted or unsubstituted benzyl group and the like. Two $G^2$s may also be taken together to form a ring, in which case the protective group may for example be methylene acetal, isopropylidene ketal and the like.

(6-2-1) Step 4B1

A step for subjecting Compound (XXII) to conversion into an oxirane to obtain Compound (XXIII) (Step 4B1) in this Step 4B is described below.

As a first synthetic method for Compound (XXIII), a method involving reacting Compound (XXII) with a sulfur ylide in a solvent can be exemplified. The sulfur ylide may for example be sulfonium methylides such as dimetylsulfonium methylide and the like or sulfoxonium methylides such as dimethyl sulfoxonium methylide and the like.

The sulfonium methylides or the sulfoxonium methylides employed can be produced by reacting, in a solvent, a sulfonium salt (for example, trimethylsulfonium iodide, trimethylsulfonium bromide and the like) or a sulfoxonium salt (for example, trimethylsulfoxonium iodide, trimethylsulfoxonium bromide and the like) with a base.

The amount of such a sulfonium methylide or sulfoxonium methylide employed per mole of Compound (XXII) described above is preferably 0.5 to 5 moles, and more preferably 0.8 to 2 moles.

While the solvent employed is not limited particularly, it can for example be amides such as N-methylpyrrolidone and N,N-dimethylformamide and the like, ethers such as tetrahydrofuran, dioxane and the like, as well as a solvent mixture thereof.

The base employed for producing sulfonium methylides and sulfoxonium methylides are not limited particularly. The base can for example be a metal hydride such as sodium hydride and the like, and an alkoxide of an alkaline metal such as sodium methoxide, sodium ethoxide, sodium t-butoxide, potassium t-butoxide and the like.

The reaction temperature and the reaction time are appropriately selected depending on the types of the solvent, Compound (XXII), sulfonium salt or sulfoxonium salt, base and the like which are employed. The reaction temperature is preferably –100 degrees C. to 200 degrees C., and more preferably –50 degrees C. to 150 degrees C. The reaction time is preferably 0.1 hour to several days, and more preferably 0.5 hour to 2 days.

Next, another synthetic method (a second synthetic method) for Compound (XXIII) is described. Specifically, Compound (XXIII) can be produced by reacting Compound (XXII) with samarium iodide and diiodomethane in a solvent, and then treating the reactant with a base.

While the base is not limited particularly, and may for example be sodium hydroxide. The samarium iodide employed can be produced by reacting a metal samarium with 1,2-diiodoethane or diiodomethane in an anhydrous solvent. The solvent employed is not limited particularly and may for example be an ether such as tetrahydrofuran and the like.

While the amount of the base per mole of Compound (XXII) is not limited particularly, it is preferably 0.5 to 10 moles in usual cases, and more preferably 0.8 to 6 moles. When treating with the base, an aqueous solution of sodium hydroxide may for example be employed since no anhydrous system is required.

The reaction temperature and the reaction time may appropriately be selected depending on the types of the solvent, Compound (XXII), base and the like which are employed. The reaction temperature is preferably –100 degrees C. to 150 degrees C., and more preferably –50 degrees C. to 100 degrees C. The reaction time is preferably 0.1 hour to several days, and more preferably 0.5 hour to 2 days.

(6-2-2) Step 4B2

Next, a step for reacting Compound (XXIII) and Compound (IV) to obtain Compound (XXIV) (Step 4B2) in this Step 4B is described below.

Compound (XXIV) is produced by mixing Compound (XXIII) with Compound (IV) in a solvent to form a carbon-nitrogen bond between the carbon atom constituting an oxirane ring in an oxirane derivative (Compound (XXIII)) and the nitrogen atom in 1,2,4-triazole or imidazole (Compound (IV)).

While the solvent employed is not limited particularly, and can for example be amides such as N-methylpyrrolidone and N,N-dimethylformamide and the like.

The amount of Compound (IV) employed per mole of Compound (XXIII) is preferably 0.5 to 10 moles in usual cases, and more preferably 0.8 to 5 moles. A base may be added if necessary. The amount of the base employed per mole of Compound (IV) is preferably 0 to 5 moles (excluding 0) in usual cases, and more preferably 0.5 to 2 moles.

While the reaction temperature may appropriately be selected depending on the types of the solvent, the base and the like which are employed, it is preferably 0 degrees C. to 250 degrees C., and more preferably 10 degrees C. to 150 degrees C. While the reaction time may also appropriately be selected depending on the types of the solvent, the base and the like which are employed, it is preferably 0.1 hour to several days, and more preferably 0.5 hour to 2 days.

It is possible to produce Compound (XXIV) by producing Compound (XXII) and then reacting it stepwise with Compound (IV) as described above. Nevertheless, in the first synthetic method described above, when the reaction for conversion into an oxirane is conducted alone, a by-product (such as an oxetane derivative) is produced, resulting in a reduced yield. In order to avoid this reduced yield, conversion into an azole may be conducted while allowing Compound (XXIII) to be produced (see Scheme (12) shown below).

Scheme (12)

[Chem.27]

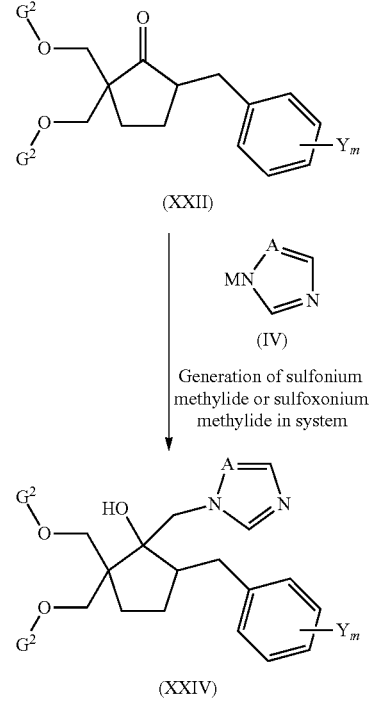

Herein, Y, m, A, $G^2$ and M are as described above.

In such a case, Compound (XXII) and Compound (IV) are dissolved in a polar solvent having an amide bond, or dimethyl sulfoxide, or a solvent mixture of a polar solvent with an alcohol. Then, to this, a trimethylsulfonium salt or a trimethylsulfoxonium salt and a base are added intermittently to produce sulfonium methylides such as dimetylsulfonium methylide and the like or sulfoxonium methylides such as dimethyl sulfoxonium methylide and the like in the reaction system, thereby effecting the conversion into an azole while allowing Compound (XXIII) to be produced.

The solvent employed here is not limited particularly. The solvent may for example be a polar solvent having an amide bond such as N-methylpyrrolidone and N,N-dimethylformamide and the like, or dimethyl sulfoxide. The alcohol in the solvent mixture may for example be t-butanol.

The base employed for producing sulfonium methylides or sulfoxonium methylides is not limited particularly. The base can for example be a metal hydride such as sodium hydride and the like, an alkoxide of an alkaline metal such as sodium methoxide, sodium ethoxide, sodium t-butoxide, potassium t-butoxide and the like. It is possible to use an alkaline metal salt of 1,2,4-triazole or imidazole.

The reaction temperature may appropriately be selected depending on the types of the solvent, Compound (XXII), sulfonium salt or sulfoxonium salt, base and the like which are employed. The reaction temperature is preferably –100 degrees C. to 250 degrees C., and more preferably –50 degrees C. to 200 degrees C. The reaction time may appropriately be selected depending on the types of the solvent, Compound (XXII), sulfonium salt or sulfoxonium salt, base and the like which are employed. The reaction time is preferably 0.1 hour to several days, and more preferably 0.5 hour to 2 days.

The number of times when a trimethyl sulfonium halide or a trimethyl sulfonium halide and a base are added intermittently is not limited particularly as long as it is the number of times allowing a predetermined aim to be accomplished. A preferred number of times is 2 to 20 times, with 3 to 15 times being more preferable. The total amount of a trimethylsulfonium salt or a trimethylsulfoxonium salt employed per mole of Compound (XXII) is preferably 0.5 to 5 moles, and more preferably 0.8 to 2 moles.

The amount of Compound (IV) employed per mole of Compound (XXII) is preferably 0.5 to 10 moles in usual cases, and more preferably 0.8 to 5 moles. It is preferable to use Compound (IV) in which M is an alkaline metal salt.

See Patent Literature 4 for the details of the steps for conducting conversion into an azole while allowing an oxirane derivative to be produced in the production of a certain azolylmethylcycloalkanol derivative.

(6-2-3) Step 4B3

Next, a step for deprotecting the protective group of Compound (XXIV) to obtain Compound (XIX) (Step 4B3) in this Step 4B is described below.

A preferred condition of the deprotection differs depending on the type of the protective group. Nevertheless, in the cases of using an alkoxymethyl group such as a methoxymethyl group, an ethoxyethyl group and the like, or a lower alkyl group such as a t-butyl group, a methyl group and the like, or a cyclic acetal or ketal protective group such as methylene acetal, isopropylidene ketal and the like, the deprotection is conducted preferably in a solvent under an acidic condition involving hydrogen chloride or sulfuric acid and the like.

The acid employed preferably in the deprotection may be a halogenated hydrogen such as hydrogen chloride or an inorganic acid such as sulfuric acid. While the amount employed is not limited particularly, the amount of the acid employed per mole of Compound (XXIV) is usually 0.5 to 100 moles, and preferably 0.8 to 20 moles.

The reaction temperature is preferably 0 degrees C. to 200 degrees C. in usual cases, and more preferably room temperature to 100 degrees C. The reaction time is preferably 0.1 hour to several days in usual cases, and more preferably 0.5 hour to 2 days.

(6-3) Step 4C

Compound (XXII) employed in Step 4B can preferably be synthesized by the method shown below.

Thus, a keto ester compound represented by Formula (XXV) shown below (hereinafter referred to as "Compound (XXV)") is hydroxymethylated to obtain a compound represented by Formula (XXVI) shown below ("Compound (XXVI)"). Then, a protective group such as a methoxymethyl group, a t-butyl group and the like is introduced into the hydroxyl group in Compound (XXVI) to effect derivatization into a compound represented by Formula (XXVII) shown below ("Compound (XXVII)"). Thereafter, Compound (XXVII) is hydrolyzed/decarbonated to obtain a carbonyl compound represented by Formula (XXII) shown below ("Compound (XXII)"). A series of these reaction procedures (Step 4C) is represented by Scheme (13) shown below.

Scheme (13)

[Chem.28]

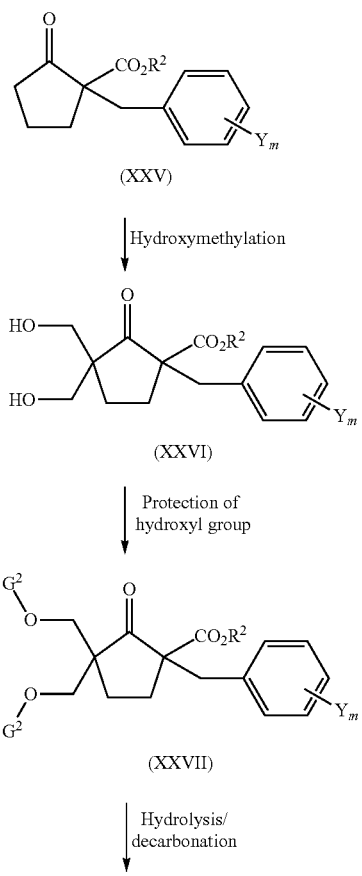

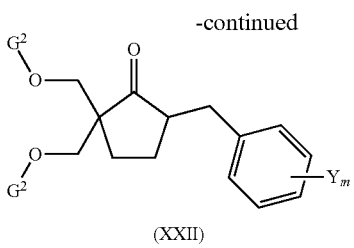

(XXII)

Herein, Y, m, $R^2$ and $G^2$ are as described above.

(6-3-1) Step 4C1

A step for bishydroxymethylating Compound (XXV) to obtain Compound (XXVI) (Step 4C1) in this Step 4C is described below. Compound (XXVI) can be produced by reacting Compound (XXV) with formaldehyde in the presence of a base in a solvent.

The amount of formaldehyde employed per mole of Compound (XXV) is preferably 0.5 to 20 moles in usual cases, and more preferably 0.8 to 10 moles.

The base can for example be, but not limited to, a carbonate of an alkaline metal such as sodium carbonate, potassium carbonate and the like as well as a hydroxide of an alkaline metal such as sodium hydroxide and the like. The amount of the base employed per mole of Compound (XXV) is preferably 0.1 to 10 moles in usual cases, and more preferably 0.2 to 5 moles.

The reaction temperature is preferably 0 degrees C. to 250 degrees C. in usual cases, and more preferably 0 degrees C. to 100 degrees C. The reaction time is preferably 0.1 hour to several days in usual cases, and more preferably 0.5 hour to 2 days.

Compound (XII) employed may be a compound produced by a known method (for example, the method disclosed in Patent Literature 1).

(6-3-2) Step 4C2

Next, a step for introducing a protective group into the hydroxyl group in Compound (XXVI) to obtain Compound (XXVII) (Step 4C2) in this Step 4C is described below.

The protective group for protecting the hydroxyl group is not limited particularly. The protective group is preferably an alkoxymethyl group such as a methoxymethyl group, an ethoxymethyl group and the like, or a lower alkyl group such as a t-butyl group and the like. Introduction of these protective groups is conducted under an acidic condition. Nevertheless, a method involving (a) an acetal exchange of the hydroxyl group in Compound (XXVI) using a formaldehyde dialkylacetal in the case of introduction of an alkoxymethyl group is preferred. (b) Introduction of the protective group to the hydroxyl group in Compound (XXVI) using isobutene is utilized preferably in the case of introduction of a t-butyl group. (c) A suitable aldehyde or ketone is employed preferably under an acidic catalyst when protecting 2 hydroxyl groups with acetal and ketal at the same time.

First, the case where the protective group is an alkoxymethyl group (in case (a)) is described.

As an acid, hydrochloric acid, phosphoric acid (including a compound allowing an acidic group to be generated by addition of an alcohol or water, such as diphosphorus pentoxide) and an inorganic acid such as sulfuric acid, an organic acid such as p-toluenesulfonic acid and the like can be employed. The formaldehyde dialkylacetal is employed preferably in the presence of an acid in a solvent or in a solvent-free system. It is further preferred to add a compound allowing any generated alcohol to be removed (for example, diphosphorus pentoxide).

The amount of the formaldehyde dialkylacetal employed per mole of Compound (XXVI) is preferably 0.5 to 50 moles in usual cases, and more preferably 0.8 to 10 moles. The amount of the acid employed per mole of Compound (XXVI) is preferably 0.01 to 10 moles in usual cases, and more preferably 0.05 to 5 moles.

The reaction temperature is preferably 0 degrees C. to 250 degrees C. in usual cases, and more preferably 0 degrees C. to 150 degrees C. The reaction time is preferably 0.1 hour to several days in usual cases, and more preferably 0.5 hour to 2 days.

When the protective group is a t-butyl group (in the case of (b)), it is preferred to conduct a reaction of Compound (XXVI) with isobutene in a solvent in the presence of an inorganic acid such as hydrochloric acid, phosphoric acid, sulfuric acid and the like, or an organic acid such as p-toluenesulfonic acid, trifluoroacetic acid and the like.

The amount of isobutene employed per mole of Compound (XXVI) is preferably 0.5 to 100 moles in usual cases, and more preferably 0.8 to 20 moles. The amount of the acid employed per mole of Compound (XXVI) is preferably 0.01 to 10 moles in usual cases, and more preferably 0.05 to 5 moles.

The reaction temperature is preferably 0 degrees C. to 200 degrees C. in usual cases, and more preferably 0 to 100 degrees C. The reaction time is preferably 0.1 to several days in usual cases, and more preferably 0.5 hour to 2 days.

When the protective group is isopropylidene ketal (in the case of (c)), it is preferred to conduct a reaction of Compound (XXVI) with acetone or acetone dimethyl acetal in a solvent in the presence of an inorganic acid such as hydrochloric acid, phosphoric acid, sulfuric acid and the like, or an organic acid such as p-toluenesulfonic acid, trifluoroacetic acid and the like.

The amount of acetone dimethyl acetal employed per mole of Compound (XXVI) is preferably 0.5 to 100 moles in usual cases, and more preferably 0.8 to 20 moles. The amount of the acid employed per mole of Compound (XXVI) is preferably 0.01 to 10 moles in usual cases, and more preferably 0.05 to 5 moles.

The reaction temperature is preferably 0 degrees C. to 200 degrees C. in usual cases, and more preferably 0 to 100 degrees C. The reaction time is preferably 0.1 hour to several days in usual cases, and more preferably 0.5 hour to 2 days.

(6-3-3) Step 4C3

Next, a reaction for hydrolyzing/decarbonating Compound (XXVII) to obtain Compound (XXII) (Step 4C3) in this Step 4C is described below.

The reaction indicated as Step 4C4 is conducted preferably in the presence of a base in a solvent. The base employed usually includes an alkaline metal base such as sodium hydroxide, potassium hydroxide and the like. The amount of base employed per mole of Compound (XXVII) is preferably 0.1 to 50 moles in usual cases, and more preferably 0.2 to 20 moles.

The solvent may usually be water, as well as water combined with an alcohol and the like, a solvent composition consisting of solvents which do not form a homogenous layer with each other (such as water-toluene). When using a solvent which does not form a homogenous layer, it may sometimes be preferable to use a phase transfer catalyst (for example a customary quaternary ammonium salt) in the reaction system.

The reaction temperature is preferably 0 degrees C. to reflux temperature in usual cases, and more preferably room temperature to reflux temperature. The reaction time is preferably 0.1 hour to several days in usual cases, and more preferably 0.5 hour to 24 hours.

3. Agro-Horticultural Agents and Industrial Material Protecting Agents

The utilities of a 2-(halogenated hydrocarbon-substituted)-5-benzyl-1-azolylmethylcyclopentanol derivatives according to the invention (Compound (I)) as an agro-horticultural agent and an industrial material protecting agent (hereinafter also referred to as "agro-horticultural agent and the like") are described below.

Since Compound (I) has a 1,2,4-triazolyl group or an imidazolyl group, it forms an acid addition salt of an inorganic acid or an organic acid, as well as a metal complex. Accordingly, Compound (I) can be employed also in the form of such an acid addition salt or the metal complex.

Furthermore, Compound (I) may have at least three asymmetric carbon atoms unless $(R^a)X^a n^a$ and $(R^b)X^b n^b$ are the same substituents. Thus, depending on the composition, it may be a stereoisomer mixture (enantiomer or diastereomer) or either one of the stereoisomers. Accordingly, at least one of these stereoisomers can be employed also as an active ingredient of an agro-horticultural agent and the like.

(1) Plant Disease Controlling Effects

Compound (I) of the invention exhibits a controlling effect on a broad range of plant diseases. Applicable diseases are exemplified below.

Soybean rust (*Phakopsora pachyrhizi, Phakopsora meibomiae*), rice blast (*Pyricularia grisea*), rice brown spot (*Cochliobolus miyabeanus*), rice leaf blight (*Xanthomonas oryzae*), rice sheath blight (*Rhizoctonia solani*), rice stem rot (*Helminthosporium sigmoideun*), rice bakanae disease (*Gibberella fujikuroi*), rice bacterial seedling blight (*Pythium aphanidermatum*), apple powdery mildew (*Podosphaera leucotricha*), apple scab (*Venturia inaequalis*), apple blossom blight (*Monilinia mali*), apple alternaria blotch (*Alternaria alternata*), apple valsa canker (*Valsa mali*), pear black spot (*Alternaria kikuchiana*), pear powdery mildew (*Phyllactinia pyri*), pear rust (*Gymnosporangium asiaticum*), pear scab (*Venturia nashicola*), grape powdery mildew (*Uncinula necator*), grape downy mildew (*Plasmopara viticola*), grape ripe rot (*Glomerella cingulata*), barley powdery mildew (*Erysiphe graminis* f. sp *hordei*), barley stem rust (*Puccinia graminis*), barley stripe rust (*Puccinia striiformis*), barley stripe (*Pyrenophora graminea*), barley leaf blotch (*Rhynchosporium secalis*), wheat powdery mildew (*Erysiphe graminis* f. sp *tritici*), wheat leaf rust (*Puccinia recondita*), wheat stripe rust (*Puccinia striiformis*), wheat eye spot (*Pseudocercosporella herpotrichoides*), wheat fusarium blight (*Fusarium graminearum, Microdochium nivale*), wheat glume blotch (*Phaeosphaeria nodorum*), wheat leaf blight (*Septoria tritici*), gourd powdery mildew (*Sphaerotheca fuliginea*), gourd anthracnose (*Colletotrichum lagenarium*), cucumber downy mildew (*Pseudoperonospora cubensis*), cucumber phytophthora rot (*Phytophthora capsici*), tomato powdery mildew (*Erysiphe cichoracearum*), tomato early blight (*Alternaria solani*), eggplant powdery mildew (*Erysiphe cichoracearum*), strawberry powdery mildew (*Sphaerotheca humuli*), tobacco powdery mildew (*Erysiphe cichoracearum*), sugar beet cercpspora leaf spot (*Cercospora beticola*), maize smut (*Ustillaga maydis*), plum brown rot (*Monilinia fructicola*), various plants-affecting gray mold (*Botrytis cinerea*), sclerotinia rot (*Sclerotinia sclerotiorum*) and the like may be exemplified. Among these, it exhibits an effect superior to a commercially available metoconazol described in Patent Literature 1 especially against wheat leaf blight (*Septoria tritici*) which is a critical disease in wheat (see Experimental Example 4 described later in the specification).

Examples of applicable plants may be wild plants, cultivated plant varieties, plants and cultivated plant varieties obtained by conventional biological breeding such as heterologous mating or plasma fusion, and plants and cultivated plant varieties obtained by gene engineering. The gene-engineered plants and the cultivated plant varieties may for example be herbicide-resistant crops, vermin-resistant crops having insecticidal protein-producing genes integrated therein, disease-resistant crops having disease resistance inducer-producing genes integrated therein, palatably improved crops, productively improved crops, preservably improved crops, productively improved crops and the like. The gene-engineered cultivated plant varieties may for example be those involving trade marks such as ROUNDUP READY, LIVERTY LINK, CLEARFIELD, YIELDGARD, HERCULEX, BLLGARD and the like.

(2) Plant Growth Promoting Effect

Furthermore, Compound (I) exhibits yield-increasing effects and quality-improving effects on a broad range of crops and horticultural plants by regulating the growth. Such crops may for example be those listed below.

Wheat, barley, oats, rice, rapeseed, sugarcane, corn, maize, soybean, pea, peanut, sugar beet, cabbage, garlic, radish, carrot, apple, pear, citric fruits such as mandarin, orange, lemon and the like, peach, cherry, avocado, mango, papaya, red pepper, cucumber, melon, strawberry, tobacco, tomato, eggplant, turf, chrysanthemum, azalea, other ornamental plants.

(3) Industrial Material Protecting Effect

Moreover, Compound (I) exhibits an excellent ability of protecting an industrial material from a broad spectrum of hazardous microorganisms which invade such a material. Examples of such microorganisms are listed below.

Paper/pulp deteriorating microorganisms (including slime-forming microorganisms) such as *Aspergillus* sp., *Trichoderma* sp., *Penicillium* sp., *Geotrichum* sp., *Chaetomium* sp., *Cadophora* sp., *Ceratostomella* sp., *Cladosporium* sp., *Corticium* sp., *Lentinus* sp., *Lezites* sp., *Phoma* sp., *Polysticus* sp., *Pullularia* sp., *Stereum* sp., *Trichosporium* sp., *Aerobacter* sp., *Bacillus* sp., *Desulfovibrio* sp., *Pseudomonas* sp., *Flavobacterium* sp. and *Micrococcus* sp.; fiber-deteriorating microorganisms such as *Aspergillus* sp., *Penicillium* sp., *Chaetomium* sp., *Myrothecium* sp., *Curvularia* sp., *Gliomastix* sp., *Memnoniella* sp., *Sarcopodium* sp., *Stachybotrys* sp., *Stemphylium* sp., *Zygorhynchus* sp., *Bacillus* sp. and *Staphylococcus* sp.; lumber-deteriorating fungi such as *Tyromyces palustris, Coriolus versicolor, Aspergillus* sp., *Penicillium* sp., *Rhizopus* sp., *Aureobasidium* sp., *Gliocladium* sp., *Cladosporium* sp., *Chaetomium* sp. and *Trichoderma* sp.; leather-deteriorating microorganisms such as *Aspergillus* sp., *Penicillium* sp., *Chaetomium* sp., *Cladosporium* sp., *Mucor* sp., *Paecilomyces* sp., *Pilobus* sp., *Pullularia* sp., *Trichos-* poron sp. and *Tricothecium* sp.; rubber/plastic-deteriorating microorganisms such as *Aspergillus* sp., *Penicillium* sp., *Rhizopus* sp., *Trichoderma* sp., *Chaetomium* sp., *Myrothecium* sp., *Streptomyces* sp., *Pseudomonas* sp., *Bacillus* sp., *Micrococcus* sp., *Serratia* sp., *Margarinomyces* sp. and *Monascus* sp.; paint-deteriorating microorganisms such as *Aspergillus* sp., *Penicillium* sp., *Cladosporium* sp., *Aureobasidium* sp., *Gliocladium* sp., *Botryodiplodia* sp., *Macrosporium* sp., *Monilia* sp., *Phoma* sp., *Pullularia* sp., *Sporotrichum* sp., *Trichoderma* sp., *Bacillus* sp., *Proteus* sp., *Pseudomonas* sp. and *Serratia* sp.

(4) Formulations

An agro-horticultural formulation containing Compound (I) as an active ingredient may contain various components other than Compound (I). The agro-horticultural formulation containing Compound (I) as an active ingredient can be mixed with a solid carrier, a liquid carrier, a surfactant, and other formulation auxiliary agents. The dosage form of the agro-horticultural formulation containing Compound (I) as an active ingredient may for example be a powder, wettable powder, granule, emulsifiable concentrate and the like.

The agro-horticultural formulation may contain Compound (I) as an active ingredient in an amount of 0.1 to 95% by weight based on the total amount of the agro-horticultural formulation. Compound (I) as an active ingredient is contained preferably in an amount of 0.5 to 90% by weight, and more preferably 2 to 80% by weight.

Carriers, diluents and surfactants employed as formulation auxiliary agents are exemplified below. The solid carriers include talc, kaolin, bentonite, diatomaceous earth, white carbon, clay and the like. The liquid carriers include water, xylene, toluene, chlorobenzene, cyclohexane, cyclohexanone, dimethyl sulfoxide, dimethyl formamide, alcohols and the like. The surfactant may appropriately be selected for an intended effect. The emulsifier may for example be polyoxiethylene alkylaryl ether, polyoxyethylene sorbitan monolaurate and the like, the dispersing agent may for example be lignin sulfonate, dibutylnaphthalene sulfonate and the like, and the wetting agent may for example be an alkyl sulfonate, alkylphenyl sulfonate and the like.

The formulation may be used as it is, or used as being diluted in a diluent such as water to a certain concentration. The concentration of Compound (I) when used as being diluted is preferably 0.001% to 1.0%.

The amount of Compound (I) for 1 ha of the agro-horticultural field such as a farm, paddy field, orchard, greenhouse and the like is 20 to 5000 g, and more preferably 50 to 2000 g. Since these concentration and amount to be used may vary depending on the dosage form, timing of use, method of use, place of use, subject crop and the like, they can be increased or decreased regardless of the ranges mentioned above.

In addition, Compound (I) can be combined with other active ingredients, including bactericides, insecticides, acaricides, herbicides and the like, such as those listed below, thereby enabling the use as an agro-horticultural agent having an enhanced performance.

<Anti-Bacterial Substances>

Acibenzolar-S-methyl, 2-phenylphenol (OPP), azaconazole, azoxystrobin, amisulbrom, bixafen, benalaxyl, benomyl, benthiavalicarb-isopropyl, bicarbonate, biphenyl, bitertanol, blasticidin-S, borax, Bordeaux mixture, boscalid, bromuconazole, bronopol, bupirimate, sec-butylamine, calcium polysulphide, captafol, captan, carbendazim, carboxin, carpropamid, quinomethionate, chloroneb, chloropicrin, chlorothalonil, chlozolinate, cyazofamid, cyflufenamid, cymoxanil, cyproconazole, cyprodinil, dazomet, debacarb, dichlofluanid, diclocymet, diclomezine, dicloran, diethofencarb, difenoconazole, diflumetorim, dimethomorph, dimoxystrobin, diniconazole, dinocap, diphenylamine, dithianon, dodemorph, dodine, edifenphos, epoxiconazole, ethaboxam, ethoxyquin, etridiazole, enestroburin, famoxadone, fenamidone, fenarimol, fenbuconazole, fenfuram, fenhexamid, fenoxanil, fenpiclonil, fenpropidin, fenpropimorph, fentin, ferbam, ferimzone, fluazinam, fludioxonil, flumorph, fluoroimide, fluoxastrobin, fluquinconazole, flusilazole, flusulfamide, flutolanil, flutriafol, folpet, fosetyl-A1, fuberidazole, furalaxyl, furametpyr, fluopicolide, fluopyram, guazatine, hexachlorobenzene, hexaconazole, hymexazol, imazalil, imibenconazole, iminoctadine, ipconazole, iprobenfos, iprodione, iprovalicarb, isoprothiolane, isopyrazam, isotianil, kasugamycin, copper preparations, such as copper hydroxide, copper naphthenate, copper oxychloride, copper sulfate, copper oxide, oxine copper, kresoxim-methyl, mancopper, mancozeb, maneb, mandipropamid, mepanipyrim, mepronil, metalaxyl, metconazole, metiram, metominostrobin, mildiomycin, myclobutanil, nitrothal-isopropyl, nuarimol, ofurace, oxadixyl, oxolinic acid, oxpoconazole, oxycarboxin, oxytetracycline, pefurazoate, orysastrobin, penconazole, pencycuron, penthiopyrad, pyribencarb, fthalide, picoxystrobin, piperalin, polyoxin, probenazole, prochloraz, procymidone, propamocarb, propiconazole, propineb, proquinazid, prothioconazole, pyraclostrobin, pyrazophos, pyrifenox, pyrimethanil, pyroquilon, quinoxyfen, quintozene, silthiopham, simeconazole, spiroxamine, sulfur and sulfur formulations, tebuconazole, tecloftalam, tecnazen, tetraconazole, thiabendazole, thifluzamide, thiophanate-methyl, thiram, thiadinil, tolclofosmethyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, amisulbrom, sedaxane, flutianil, valiphenal, ametoctradin, dimoxystrobin, metrafenone, hydroxyisoxazole, metasulfocarb and the like.

<Insecticides/Acaricides/Nematocides>

Abamectin, acephate, acrinathrin, alanycarb, aldicarb, allethrin, amitraz, avermectin, azadirachtin, azamethiphos, azinphos-ethyl, azinphos-methyl, azocyclotin, *Bacillus firmus, Bacillus subtilis, Bacillus thuringiensis*, bendiocarb, benfuracarb, bensultap, benzoximate, bifenazate, bifenthrin, bioallethrin, bioresmethrin, bistrifluron, buprofezin, butocarboxim, butoxycarboxim, cadusafos, carbaryl, carbofuran, carbosulfan, cartap, CGA50439, chlordane, chlorethoxyfos, chlorphenapyr, chlorfenvinphos, chlorfluazuron, chlormephos, chlorpyrifos, chlorpyrifos methyl, chromafenozide, clofentezine, clothianidin, chlorantraniliprole, coumaphos, cryolite, cyanophos, cycloprothrin, cyfluthrin, cyhalothrin, cyhexatin, cypermethrin, cyphenothrin, cyromazine, Cyazapyr, cyenopyrafen, DCIP, DDT, deltamethrin, demeton-S-methyl, diafenthiuron, diazinon, dichlorophen, dichloropropene, dichlorvos, dicofol, dicrotophos, dicyclanil, diflubenzuron, dimethoate, dimethylvinphos, dinobuton, dinotefuran, emamectin, endosulfan, EPN, esfenvalerate, ethiofencarb, ethion, ethiprole, ethofenprox, ethoprophos, etoxazole, famphur, fenamiphos, fenazaquin, fenbutatin oxide, fenitrothion, fenobucarb, fenothiocarb, fenoxycarb, fenpropathrin, fenpyroximate, fenthion, fenvalerate, fipronil, flonicamid, fluacrypyrim, flucycloxuron, flucythrinate, flufenoxuron, flumethrin, fluvalinate, flubendiamide, formetanate, fosthiazate, halfenprox, furathiocarb, halofenozide, gamma-HCH, heptenophos, hexaflumuron, hexythiazox, hydramethylnon, imidacloprid, imiprothrin, indoxacarb, isoprocarb, isoxathion, lufenuron, malathion, mecarbam, metam, methamidophos, methidathion, methiocarb, methomyl, methoprene, methothrin, methoxyfenozide, metolcarb, milbemectin, monocrotophos, naled, nicotine, nitenpyram, novaluron, noviflumuron, omethoate, oxamyl, oxydemethon methyl, parathion, permethrin, phenthoate, phorate, phosalone, phosmet, phosphamidon, phoxim, pirimicarb, pirimiphos-methyl, profenofos, propoxur, prothiophos, pymetrozin, pyrachlophos, pyrethrin, pyridaben, pyridalyl, pyrimidifen, pyriproxifen, pyrifluquinazon, pyriprole, quinalphos, silafluofen, spinosad, spirodiclofen, spiromesifen, spirotetramat, sulfluramid, sulphotep, SZI-121, tebufenozid, tebufenpyrad, tebupirimphos, teflubenzuron, tefluthrin, temephos, terbufos, tetrachlorvinphos, thiacloprid, thiamethoxam, thiodicarb, thiofanox, thiometon, tolfenpyrad, tralomethrin, tralopyril, triazamate, triazophos, trichlorfon, triflumuron, vamidothion, valifenal, XMC, xylylcarb, imicyafos, lepimectin and the like.

<Plant Growth Regulators>

Ancymidol, 6-benzylaminopurine, paclobutrazol, diclobutrazole, uniconazole, methylcyclopropene, mepiquat chloride, ethefon, chlormequat chloride, inabenfide, prohexadione and its salts, trinexapac-ethyl and the like. As plant hormones, jasmonic acid, brassinosteoid, gibberellin and the like.

An industrial material protecting agents containing Compound (I) as an active ingredient may contain various components other than Compound (I). The industrial material protecting agents containing Compound (I) as an active ingredient can be used as being dissolved or dispersed in a suitable liquid carrier or as being mixed with a solid carrier. The industrial material protecting agents containing Compound (I) as an active ingredient may further contain an emulsifier, dispersing agent, spreading agent, penetrating agent, wetting agent, stabilizer and the like. The dosage form of the industrial material protecting agents containing Compound (I) as an active ingredient may for example be a wettable powder, powder, granule, tablet, paste, suspension, spray and the like. The industrial material protecting agents containing Compound (I) as an active ingredient may contain other biocides, insecticides, deterioration-preventing agent and the like.

The liquid carrier may be any liquid as long as it does not react with an active ingredient. The liquid carrier may for example be water, alcohols (for example, methyl alcohol, ethyl alcohol, ethylene glycol, cellosolve and the like), ketones (for example, acetone, methylethylketone and the like), ethers (for example, dimethyl ether, diethyl ether, dioxane, tetrahydrofuran and the like), aromatic hydrocarbons (for example, benzene, toluene, xylene, methylnaphthalene and the like), aliphatic hydrocarbons (for example, gasoline, kerosene, paraffin oil, machine oil, fuel oil and the like), acid amides (for example, dimethyl formamide, N-methylpyrrolidone and the like), halogenated hydrocarbons (for example, chloroform, carbon tetrachloride and the like), esters (for example, acetic acid ethyl ester, fatty acid glycerin ester and the like), nitriles (for example, acetonitrile and the like), and dimethyl sulfoxide and the like.

The solid carrier may for example be a microparticle or a granule of kaolin clay, bentonite, acid clay, pyrophylite, talc, diatomaceous earth, calcite, urea, ammonium sulfate and the like.

The emulsifiers and the dispersing agents may for example be soaps, alkyl sulfonates, alkylaryl sulfonates, dialkyl sulfosuccinates, quaternary ammonium salts, oxyalkylamines, fatty acid esters, polyalkylene oxide-based, anhydrosorbitol-based surfactants.

When Compound (I) is contained as an active ingredient in a formulation, it is added in such an amount that the concentration becomes 0.1 to 99.9% by weight based on the entire amount of the formulation, although the content may vary depending on the dosage form and the purpose of use. Upon being used practically, it is combined appropriately with a solvent, diluent, extender and the like so that the treatment concentration is usually 0.005 to 5% by weight, and preferably 0.01 to 1% by weight.

As described above, an azole derivative represented by Compound (I) exhibits an excellent biocidal effect on a large number of microorganisms which induce diseases in plants. Thus, an agro-horticultural disease controlling agent containing Compound (I) as an active ingredient has a low toxicity to humans and animals, are capable of being handled safely, and exhibits a high controlling effect on a wide range of plant diseases.

(Remarks)

The invention is not limited to the embodiments described above, and it may be varied in various ways within the scope of the appended Claims. Thus, an embodiment achieved by combining technical means varied appropriately within the scope of the appended Claims will be included by the technical scope of the invention.

EXAMPLES

The invention is embodied below with referring to Production Examples, Formulation Examples, and Experimental Examples. The invention is not restricted to the following Production Examples, Formulation Examples, and Experimental Examples unless departing from its scope.

Production Example 1

Synthesis of (1RS,2SR,5SR)-5-(4-chlorobenzyl)-2-chloromethyl-2-methyl-1-(1H-1,2,4-triazol-1-ylmethyl)cyclopentanol (Compound No. I-1 (Compound (I), $(R^a)X^an^a$=CH$_3$, $(R^b)X^bn^b$=CH$_2$Cl, Ym=4-Cl, A=N, isomer type: C)) (Production by Step 1A in First Production Method)

Under argon atmosphere, (1RS,2RS,3SR)-p-toluenesulfonic acid 3-(4-chlorobenzyl)-2-hydroxy-1-methyl-2-(1H-1,2,4-triazol-1-ylmethyl)cyclopentyl methyl ester (Compound No. II-1 (Compound (II), $(R^{a1})X^{a1}n^{a1}$ ($L^a$) $p^a$=CH$_3$, $(R^{b1})X^{b1}n^{b1}$ ($L^b$)$p^b$=CH$_2$OTos, Ym=4-Cl, A=N, isomer type: C)) (12.0 mg, 0.0245 mmol) was dissolved in dehydrated DMF (0.24 ml). Lithium chloride (10.4 mg, 0.245 mmol) was added, and stirring was conducted for 1.5 hours at 100 degrees C. To the reaction solution, ethyl acetate (2 ml) was added, washed with saturated brine (0.5 ml×5). The organic layer was dried over anhydrous sodium sulfate, and then concentrated. Silica gel column chromatography (eluent; hexane:ethyl acetate=1:2) was employed for purification to obtain an intended substance.

Product: 5.0 mg

Yield: 58%

Description: White solid, Melting point (m.p.) 139-140 degrees C.

$^1$H-(400 MHz, CDCl$_3$) delta:

1.18 (3H, s), 1.46 (2H, m), 1.70 (1H, m), 1.92 (2H, m), 2.35 (2H, m), 3.26 (1H, d, J=10.8 Hz), 3.57 (1H, d, J=10.8 Hz), 4.06 (1H, s), 4.25 (1H, d, J=14.2 Hz), 4.54 (1H, d, J=14.2 Hz), 6.98 (2H, d, J=8.4 Hz), 7.21 (2H, d, J=8.4 Hz), 8.02 (1H, s), 8.19 (1H, s).

Compound (I) can also be produced from Intermediate (XVI) as shown below in accordance with the third production method described above. As an example, the production of I-1 is shown below.

Synthesis of (1RS,2SR,5SR)-5-(4-chlorobenzyl)-2-chloromethyl-2-methyl-1-(1H-1,2,4-triazol-1-ylmethyl)cyclopentanol (Compound No. I-1 (Compound (I), $(R^a)X^an^a$=CH$_3$, $(R^b)X^bn^b$=CH$_2$Cl, Ym=4-Cl, A=N, isomer type: C)) (Production by Step 3A in Third Production Method)

(1RS,4SR,5RS)-4-(4-Chlorobenzyl)-1-methyl-5-(1H-1,2,4-triazol-1-ylmethyl)-6-oxa bicyclo[3,2,0]heptane Compound No. XVI-1 (Compound (XVI), $[(R^{a2})X^{a2}n^{a2}(OR^3)p^{a1}]$=CH$_3$, Ym=4-Cl, A=N, isomer type: C) (20.79 g, 62.3 mmol) was dissolved in DMF (200 ml), and heated to 80 degrees C. To this, lithium chloride (39.59 g, 934 mmol) and p-toluenesulfonic acid monohydrate (14.20 g, 74.8 mmol) were added, and stirring was conducted for 1.5 hours. After completion of the reaction, DMF was distilled away under reduced pressure, the residue was combined with water, and extracted with ethyl acetate. The organic layer was washed with water and saturated brine, and dried over anhydrous sodium sulfate. The solvent was distilled away, and the residue was recrystallized from ethyl acetate/hexane to obtain the desired substance.

Product: 22.24 g

Yield: 95.9%

The melting point and the NMR spectrum of Compound I-1 produced in this method were in complete agreement with that synthesized by the method described above.

Production Example 2

Synthesis of (1RS,2RS,5SR)-5-(4-chlorobenzyl)-2-chloromethyl-2-methyl-1-(1H-1,2,4-triazol-1-ylmethylcyclopentanol (Compound No. I-101 (Compound (I), $(R^a)X^an^a$=CH$_2$Cl, $(R^b)X^bn^b$=CH$_3$, Ym=4-Cl, A=N, isomer type: C))

Under argon atmosphere, (1RS,2SR,3RS)-p-toluenesulfonic acid 3-(4-chlorobenzyl)-2-hydroxy-1-methyl-2-(1H-1,2,4-triazol-1-ylmethyl)cyclopentyl methyl ester (Compound No. II-2 (Compound (II), $(R^{a1})X^{a1}n^{a1}(L^a)p^a$=CH$_2$OTos, $(R^{b1})X^{b1}n^{b1}(L^b)p^b$=CH$_3$, Ym=4-Cl, A=N, isomer type: C)) (10.6 mg, 0.0216 mmol) was dissolved in dehydrated DMF (0.21 ml). Lithium chloride (9.2 mg, 0.216 mmol) was added, and stirring was conducted for 3 hours at 100 degrees C. To the reaction solution, ethyl acetate (2 ml) was added, and washing with saturated brine (0.5 ml×5) was conducted. The organic layer was dried over anhydrous sodium sulfate, and then concentrated. Silica gel column chromatography (eluent; hexane:ethyl acetate=1:1) was employed for purification to obtain an intended substance.

Product: 4.6 mg

Yield: 60%

Description: White solid, Melting point (m.p.) 124 degrees C.

$^1$H-NMR (400 MHz, CDCl$_3$) delta:

0.81 (3H, s), 1.41-1.77 (4H, m), 2.30 (1H, m), 2.42 (1H, dd, J=13.6, 4.7 Hz), 2.51 (1H, dd, J=13.6, 10.1 Hz), 3.52 (1H, d, J=11.1 Hz), 3.61 (1H, d, J=11.1 Hz), 3.98 (1H, s), 4.24 (1H, d, J=14.2 Hz), 4.38 (1H, d, J=14.2 Hz), 7.03 (2H, d, J=8.4 Hz), 7.22 (2H, d, J=8.4 Hz), 7.99 (1H, s), 8.20 (1H, s).

Production Example 3

Synthesis of (1RS,2SR,5SR)-2-bromomethyl-5-(4-chlorobenzyl)-2-methyl-1-(1H-1,2,4-triazol-1-ylmethyl)cyclopentanol (Compound No. I-25 (Compound (I), $(R^a)X^an^a$=CH$_3$, $(R^b)X^bn^b$=CH$_2$Br, Ym=4-Cl, A=N, isomer type: C))

(1RS,2RS,3SR)-p-Toluenesulfonic acid 3-(4-chlorobenzyl)-2-hydroxy-1-methyl-2-(1H-1,2,4-triazol-1-ylmethyl)cyclopentyl methyl ester (Compound No. II-1 (Compound (II), $(R^{a1})X^{a1}n^{a1}(L^a)p^a$=CH$_3$ $(R^{b1})X^{b1}n^{b1}(L^b)p^b$=CH$_2$OTos, Ym=4-Cl, A=N, isomer type: C)) (400 mg, 0.8163 mmol) was dissolved in dehydrated DMF (8 ml) under argon atmosphere. Lithium bromide (756 mg, 8.706 mmol) was added, and stirring was conducted for 8 hours at 60 degrees C. The reaction solution was cooled, ethyl acetate (66 ml) was added, and washing with saturated brine (20 ml×3) was conducted. The organic layer was dried over anhydrous sodium sulfate, and then concentrated. Silica gel chromatography (eluent; hexane:ethyl acetate=1:2) was employed for purification to obtain an intended substance.

Product: 56 mg

Yield: 17%

Description: Solid, m.p. 235-236 degrees C.

$^1$H-NMR (400 MHz, CDCl$_3$) delta:

1.19 (3H, s), 1.41-1.53 (2H, m), 1.65-1.75 (1H, m), 1.91-2.04 (2H, m), 2.32-2.41 (2H, m), 2.96 (1H, d, J=9.9 Hz), 3.54 (1H, d, J=9.9 Hz), 4.09 (1H, s), 4.23 (1H, d, J=14.2 Hz), 4.50 (1H, d, J=14.2 Hz), 6.99 (2H, d, J=8.4 Hz), 7.21 (2H, d, J=8.4 Hz), 8.01 (1H, s), 8.18 (1H, s).

Production Example 4

Synthesis of (1RS,2SR,5SR)-5-(4-chlorobenzyl)-2-(2-chloroethyl)-2-methyl-1-(1H-1,2,4-triazol-1-ylmethyl)cyclopentanol (Compound No. I-104 (Compound (I), $(R^a)X^an^a$=CH$_2$CH$_2$Cl, $(R^b)X^bn^b$=CH$_3$, Ym=4-Cl, A=N, isomer type: C))

p-Toluenesulfonic acid 2-[(1RS,2SR,3RS)-3-(4-chlorobenzyl)-2-hydroxy-1-methyl-2-(1H-1,2,4-triazol-1ylmethyl)cyclopentyl]ethyl ester (Compound No. II-3 (Compound (II), $(R^{a1})X^{a1}n^{a1}(L^a)p^a$=CH$_3$, $(R^{b1})X^{b1}n^{b1}(L^b)p^b$=CH$_2$CH$_2$OTos, Ym=4-Cl, A=N, isomer type: C)) (42 mg, 0.084 mmol) was dissolved in DMF (1 ml). Lithium chloride (33 mg, 0.77 mmol) was added, and stirring was conducted for 4 hours at 80 degrees C. The solvent was distilled away, and ethyl acetate was added. The organic layer was washed with water and saturated brine, dried over anhydrous sodium sulfate, and then concentrated. Silica gel column chromatography (eluent; chloroform:ethyl acetate=1:2) was employed for purification to obtain an intended substance.

Product: 22 mg

Yield: 71%

Description: Colorless liquid $^1$H-NMR (400 MHz, CDCl$_3$) delta:

0.66 (3H, s), 1.43-1.53 (2H, m), 1.61-1.74 (2H, m), 1.83-1.89 (2H, m), 2.18-2.26 (1H, m), 2.40 (1H, dd, J=13.6, 4.9 Hz), 2.48 (1H, dd, J=13.6, 10.0 Hz), 3.46-3.57 (2H, m), 4.01 (1H, s), 4.16 (1H, d, J=14.1 Hz), 4.18 (1H, d, J=14.1 Hz), 7.01 (2H, d, J=8.4 Hz), 7.21 (2H, d, J=8.4 Hz), 7.99 (1H, s), 8.16 (1H, s).

Production Example 5

Synthesis of (1RS,2SR,5SR)-5-(4-chlorobenzyl)-2-trifluoromethyl-1-(1H-1,2,4-triazol-1-ylmethyl)cyclopentanol (Compound No. I-65 (Compound (I), $(R^a)X^an^a$=H, $(R^b)X^bn^b$=$CF_3$, Ym=4-Cl, A=N, isomer type: C)) and (1RS,2SR,5RS)-5-(4-chlorobenzyl)-2-trifluoromethyl-1-(1H-1,2,4-triazol-1-ylmethyl)cyclopentanol (Compound No. I-365 (Compound (I), $(R^a)X^an^a$=H, $(R^b)X^bn^b$=$CF_3$, Ym=4-Cl, A=N, isomer type: T))

(1) Synthesis of intermediate 7-(4-chlorobenzyl)-4-trifluoromethyl-1-oxaspiro[2.4]heptane (Compound (III), $(R^a)X^an^a$=H, $(R^b)X^bn^b$=$CF_3$, Ym=4-Cl)

Under nitrogen flow, anhydrous THF (1 ml) was combined with Sm (705 mg, 4.7 mmol), and a solution of 1,2-diiodoethane (662 mg, 2.3 mmol) dissolved in anhydrous THF (2 ml) was added dropwise with stirring. The reaction solution was stirred for 30 minutes at room temperature. Thereafter, while cooling with ice, a solution of diiodomethane (723 mg, 2.7 mmol) and 5-(4-chlorobenzyl)-2-trifluoromethylcyclopentanone (Compound (V), $(R^a)X^an^a$=H, $(R^b)X^bn^b$=$CF_3$, Ym=4-Cl) (432 mg, 1.6 mmol) dissolved in anhydrous THF (2 ml) was added dropwise, and stirring was continued for 2 hours at room temperature. The reaction solution was poured into a solution mixture of an aqueous solution of NaOH (NaOH (1.1 g) dissolved in 10 ml of water) and THF (10 ml), and stirring was continued for 30 minutes at room temperature. This reaction solution was combined with ice, neutralized with a 1N aqueous solution of hydrochloric acid, and then extracted with hexane. The organic layer was washed with water and saturated brine, and dried over anhydrous sodium sulfate. The solvent was distilled away under reduced pressure. Silica gel chromatography (eluent; hexane: ethyl acetate=70:1) was conducted for purification to obtain the desired substance.

Product: 111 mg
Yield: 24%
Description: Yellow oil
$^1$H-NMR (400 MHz, $CDCl_3$) delta:
1.46-2.07 (m, 4H), 2.35-2.45 (m, 2H), 2.57-2.90 (m, 2H), 2.72 (d, J=4.8 Hz), 2.90 (d, J=4.8 Hz), 7.09 (m, 2H), 7.24 (d, 2H, J=8.4 Hz).

(2) Synthesis of Compound No. I-65 and Compound No. I-365

60% Sodium hydride 24 mg (0.60 mmol) washed with hexane was suspended in anhydrous DMF (0.4 ml), and 39 mg (0.56 mmol) of 1H-1,2,4-triazole was added while cooling with ice. After stirring for 20 minutes at room temperature, a solution of Compound (III) (111 mg, 0.38 mmol) synthesized above in anhydrous DMF (0.6 ml) was added, and stirring was conducted with heating at 95 degrees C. for 3 hours. The reaction solution was poured into ice/water and extracted with ethyl acetate. The organic layer was washed with dilute hydrochloric acid and saturated brine, and then dried over anhydrous sodium sulfate. Under reduced pressure, the solvent was distilled away, and the crude product was purified by silica gel chromatography (eluent; hexane: ethyl acetate=2:3 to 1:7) to obtain the desired substance.

<Compound No. I-65>
Product: 43 mg
Yield: 31%
Description: Yellowish orange oil
$^1$H-NMR (400 MHz, $CDCl_3$) delta:
1.63 (2H, m), 1.84 (1H, m), 2.00 (2H, m), 2.44 (1H, dd-like, J=13.4, 10.4 Hz), 2.57 (1H, dd-like, J=13.4, 4.4 Hz), 2.64 (1H, m), 2.81 (1H, bs), 4.37 (1H, d, J=14.2 Hz), 4.42 (1H, d, J=14.2 Hz), 7.08 (2H, d, J=8.2 Hz), 7.24 (d, 2H, J=8.2 Hz), 8.01 (s, 1H), 8.10 (s, 1H).

<Compound No. I-365>
Product: 10 mg
Yield: 7%
Description: Yellowish orange oil
$^1$H-NMR (400 MHz, $CDCl_3$) delta:
1.35 (2H, m), 1.91 (2H, m), 2.28 (2H, m), 2.51 (1H, m), 3.14 (1H, d-like, J=10.0 Hz), 3.89 (1H, bs), 4.28 (1H, d J=14.0 Hz), 4.39 (1H, d, J=14.0 Hz), 7.07 (2H, d, J=8.2 Hz), 7.26 (d, 2H, J=8.2 Hz), 8.02 (s, 1H), 8.22 (s, 1H).

Production Example 6

Synthesis of (1RS,2RS,5SR)-5-(4-chlorobenzyl)-2-(2-chloropropenyl)-2-methyl-1-(1H-1,2,4-triazol-1-ylmethyl)cyclopentanol (Compound No. I-15 (Compound (I), $(R^a)X^an^a$=$CH_3$, $(R^b)X^bn^b$=$CH_2CCl$=$CH_2$, Ym=4-Cl, A=N, isomer type: C)) and (1RS,2SR,5SR)-5-(4-chlorobenzyl)-2-(2-chloropropenyl)-2-methyl-1-(1H-1,2,4-triazol-1-ylmethyl)cyclopentanol (Compound No. I-115 (Compound (I), $(R^a)X^an^a$=$CH_2$ $CCl$=$CH_2$, $(R^b)X^bn^b$=$CH_3$, Ym=4-Cl, A=N, isomer type: C))

(1) Synthesis of Intermediate 7-(4-chlorobenzyl)-4-(2-chloropropenyl)-4-methyl-1-oxaspiro[2.4]heptane (Compound (III), $(R^a)X^an^a$=$CH_3$, $(R^b)X^bn^b$=$CH_2CCl$=$CH_2$, Ym=4-Cl)

Under argon atmosphere, anhydrous THF (9 ml) was combined with Sm (1.01 g, 6.71 mmol), and then, at room temperature, 1,2-diiodoethane (1.05 g, 3.73 mmol) was added. The reaction solution was stirred for 1 hour at room temperature, and then cooled to −7 degrees C. to −2 degrees C., and 2-(2-chloro-2-propenyl)-5-(4-chlorobenzyl)-2-methylcyclopentanone (Compound (V), $(R^a)X^an^a$=$CH_3$, $(R^b)X^bn^b$=$CH_2CCl$=$CH_2$, Ym=4-Cl) dissolved in diiodomethane (0.90 g, 0.00168×2.0 mol) and THF (5 ml) was added, and stirred for 1.5 hours at the same temperature. To this, a 2N aqueous solution of NaOH (8 ml) was added, and stirring was conducted for 1 hour while cooling with ice. A 2N aqueous solution of hydrochloric acid (8 ml) was added, and then extraction with hexane (100 ml×2) was conducted. The organic layer was washed with water (50 ml) and saturated brine (30 ml), and then dried over anhydrous sodium sulfate and concentrated to obtain a crude intended substance (0.44 g), which was used in the next reaction as it was.

(2) Synthesis of Compound No. I-15 and Compound No. I-115

A crude compound (III) (0.24 g, 0.77 mmol) synthesized above was dissolved in DMF (1.5 ml), and potassium carbonate (0.108 g, 0.781 mmol) and 1H-1,2,4-triazole (0.053 g, 0.77 mmol) was added, and stirring was conducted at about 80 degrees C. for 2 hours and at about 90 degrees C. for 2 hours. To the reaction solution, ethyl acetate (50 ml) and water (30 ml) was added, and then partitioned. The aqueous layer was extracted with ethyl acetate (50 ml), and then the organic layer was washed with saturated brine (50 ml), and then dried over anhydrous sodium sulfate, and concentrated.

A silica gel column (eluent; hexane:ethyl acetate=2:1 to 1:2) was employed for purification to obtain an intended substance.

Compound No. I-15
Product: 15 mg
Yield: 4%
Description: Yellow oil
$^1$H-NMR (400 MHz, CDCl$_3$) delta:
1.11 (3H, s), 1.40-2.50 (8H, m), 2.59 (1H, d, J=14.0 Hz), 3.82 (1H, s), 4.23 (1H, d, J=14.2 Hz), 4.33 (1H, d, J=14.2 Hz), 5.02 (1H, s), 5.20 (1H, s), 6.99-7.07 (2H, m), 7.18-7.25 (2H, m), 8.01 (1H, s), 8.19 (1H, s).

<Compound No. I-115>
Product: 60 mg
Yield: 16%
Description: Yellow oil
$^1$H-NMR (400 MHz, CDCl$_3$) delta:
0.75 (3H, s), 1.40-1.58 (1H, m), 1.62-1.83 (3H, m), 2.15-2.53 (5H, m), 3.72 (1H, s), 4.14 (1H, d, J=14.1 Hz), 4.25 (1H, d, J=14.1 Hz), 5.12 (1H, d, J=1.1 Hz), 5.32 (1H, d, J=1.1 Hz), 6.99-7.06 (2H, m), 7.18-7.26 (2H, m), 7.99 (1H, s), 8.16 (1H, s).

While these isomers may exist in 4 types with regard to the relative steric configuration, 2 types was produced, and the hydroxyl group and the benzyl group in 5-position was considered to be in a cis configuration based on the reactivity with samarium iodide, and accordingly, the isomer type was assumed to be and assigned to C, although there is a possibility of isomer type T (Compound No. I-315 and I-415).

Production Example 7

Synthesis of (1RS,2SR,5SR)-5-(4-chlorobenzyl)-2-chloromethyl-2-ethyl-1-(1H-1,2,4-triazol-1-ylmethyl)cyclopentanol (Compound No. I-36 (Compound (I), $(R^a)X^an^a$=CH$_2$CH$_3$, $(R^b)X^bn^b$=CH$_2$Cl, Ym=4-Cl, A=N, isomer type: C))

(1RS,2RS,3SR)-p-Toluenesulfonic acid 3-(4-chlorobenzyl)-1-ethyl-2-hydroxy-2-(1H-1,2,4-triazol-1-yl)methylcyclopentylmethyl ester (Compound No. II-4 (Compound (II), $(R^{a1})X^{a1}n^{a1}$ $(L^a)p^a$=CH$_2$CH$_3$, $(R^{b1})X^{b1}n^{b1}$ $(L^b)p^b$=CH$_2$OTos, Ym=4-Cl, A=N, isomer type: C)) (56.1 mg, 0.111 mmol) was dissolved in DMF (1.1 ml), and lithium chloride (47.2 mg, 1.11 mmol) was added, and stirring was conducted for 30 minutes at 80 degrees C. After completion of the reaction, water was added, and extraction with ethyl acetate was conducted. The organic layer was washed with saturated brine, and then washed with anhydrous sodium sulfate. The solvent was distilled away, and the residue was subjected to silica gel column chromatography (eluent; hexane: ethyl acetate=1:3) for purification to obtain the desired substance.

Product: 3.0 mg
Yield: 7%
Description: White solid, Melting point (m.p.) 113.0 degrees C.
$^1$H-NMR (400 MHz, CDCl$_3$) delta:
0.94 (3Ht, J=7.3 Hz), 1.31-1.46 (2H, m), 1.49 (1H, dd, J=13.0, 3.2 Hz), 1.50-1.63 (3H, m), 1.79-1.80 (1H, m), 2.13 (1H, dd, J=13.0, 11.5 Hz), 2.23-2.31 (1H, m), 3.50 (1H, d, J=11.4 Hz), 4.03 (1H, s), 4.09 (1H, d, J=11.4 Hz), 4.34 (1H, d, J=14.2 Hz), 4.79 (1H, d, J=14.2 Hz), 6.88 (2H, d, J=8.4 Hz), 7.17 (2H, d, J=8.4 Hz), 8.01 (1H, s), 8.21 (1H, s).

Production Example 8

Synthesis of cis-5-(4-chlorobenzyl)-2,2-bis(chloromethyl)-1-(1H-1,2,4-triazol-1-yl)methylcyclopentanol (Compound No. I-203 (Compound (I), $(R^a)X^an^a$=CH$_2$Cl, $(R^b)X^bn^b$=CH$_2$Cl, Ym=4-Cl, A=N, isomer type: C))

cis-5-(4-Chlorobenzyl)-2,2-bis(methanesulfonyloxymethyl)-1-(1H-1,2,4-triazol-1-ylmethyl)cyclopentanol (Compound No. II-5 (Compound (II), $(R^{a1})X^{a1}n^{a1}$ $(L^a)p^a$=CH$_2$OMs, $(R^{b1})X^{b1}n^{b1}$ $(L^b)p^b$=CH$_2$OMs, Ym=4-Cl, A=N, isomer type: C)) (73.9 mg, 0.136 mmol) was dissolved in DMF (1.5 ml) and lithium chloride (57.8 mg, 1.42 mmol) was added, and then stirring was conducted for 7 hours at 80 degrees C. To this, p-toluenesulfonic acid monohydrate (12.9 mg, 0.68 mmol) was added, and then stirring was conducted further for 4 hours. After completion of the reaction, water was added, and extraction with ethyl acetate was conducted. The organic layer was washed with saturated brine, and dried over anhydrous sodium sulfate. The solvent was distilled away, and the residue was subjected to silica gel column chromatography (eluent; hexane: ethyl acetate=1:1) for purification to obtain the desired substance.

Product: 9.7 mg
Yield: 18%
Description: Colorless viscous liquid
$^1$H-NMR (400 MHz, CDCl$_3$) delta:
1.45-1.55 (1H, m), 1.61-1.75 (2H, m), 1.86-1.95 (1H, m), 2.26-2.37 (2H, m), 3.72 (1H, d, J=11.7 Hz), 3.73 (1H, d, J=11.3 Hz), 3.80 (1H, d, J=11.3 Hz), 3.82 (1H, d, J=11.7 Hz), 4.30 (1H, d, J=14.1 Hz), 4.54 (1H, s), 4.78 (1H, d, J=14.1 Hz), 6.93 (2H, d, J=8.4 Hz), 7.19 (2H, d, J=8.4 Hz), 8.02 (1H, s), 8.22 (1H, s).

Production Example 9

Synthesis of (1RS,2SR,5RS)-5-(4-chlorobenzyl)-2-chloromethyl-2-methyl-1-[1,2,4]triazol-1-ylmethylcyclopentanol (Compound No. I-301 (Compound (I), $(R^a)X^an^a$=CH$_3$, $(R^b)X^bn^b$=CH$_2$Cl, Ym=4-Cl, A=N, isomer type: T))

(1RS,4RS,5RS)-4-(4-Chlorobenzyl)-1-methyl-5-(1H-1,2,4-triazol-1-ylmethyl)-6-oxa bicyclo[3,2,0]heptane (Compound No. (XVI)-2, (Compound (XVI), $(R^a)X^an^a$=CH$_3$, Ym=4-Cl, A=N, isomer type: T)) (150.1 mg, 0.472 mmol) was dissolved in DMF (3 ml), and lithium chloride (300.3 mg, 7.08 mmol) and p-toluenesulfonic acid monohydrate (107.7 mg, 0.566 mmol) were added, and stirring was conducted for 1.5 hours at 80 degrees C. After completion of the reaction, DMF was distilled away under reduced pressure, the residue was combined with aqueous saturated sodium hydrogen carbonate and water, and extracted with ethyl acetate. The organic layer was washed with water and saturated brine, and dried over anhydrous sodium sulfate, the solvent was distilled away, and the residue was recrystallized from ethyl acetate/hexane to obtain the desired substance.

Product: 130.1 mg
Description: Colorless crystal, Melting point (m.p.) 133.8 degrees C.
Yield: 77.8%
$^1$H-NMR (400 MHz, CDCl$_3$) delta:
1.23 (3H, s), 1.34-1.43 (1H, m), 1.61-1.69 (1H, m), 1.74-1.83 (1H, m), 1.86-1.94 (1H, m), 2.20-2.29 (1H, m), 2.33 (1H, t, J=12.1 Hz), 2.93 (1H, dd, J=12.1, 2.8 Hz), 3.56 (1H, d, J=10.9 Hz), 3.63 (1H, d, J=10.9 Hz), 4.19 (1H, s), 4.47 (1H, d, J=14.2 Hz), 4.52 (1H, d, J=14.2 Hz), 6.95 (2H, d, J=8.3 Hz), 7.21 (2H, d, J=8.3 Hz), 8.03 (1H, s), 8.21 (1H, s).

Production Example 10

Synthesis of (1RS,2RS,5RS)-5-(4-chlorobenzyl)-2-chloromethyl-2-methyl-1-[1,2,4]triazol-1-ylmethyl-cyclopentanol (Compound No. I-401 (Compound (I), $(R^a)X^a n^a$=CH$_2$Cl, $(R^b)X^b n^b$=CH$_3$, Ym=4-Cl, A=N, isomer type: T))

(1RS,2SR,5RS)-5-(4-Chlorobenzyl)-2-(p-toluenesulfonyl)oxymethyl-2-methyl-1-[1,2,4]triazol-1-ylmethylcyclopentanol (Compound No. II-6 (Compound (II), $(R^{a1})X^{a1}n^{a1}(L^a)p^a$=CH$_2$OTos, $(R^{b1})X^{b1}n^{b1}(L^b)p^b R^{b1}m$=CH$_3$, Ym=4-Cl, A=N, isomer type: T)) (215.7 mg, 0.440 mmol) was dissolved in DMF (4 ml), and lithium chloride (280 mg, 6.60 mmol) was added, and stirring was conducted for 3.5 hours at 80 degrees C. After completion of the reaction, the solvent was distilled away, water was added and extraction with ethyl acetate was conducted. The organic layer was washed with water and saturated brine, and dried over anhydrous sodium sulfate. The solvent was distilled away, and the residue was subjected to silica gel column chromatography (eluent; hexane: ethyl acetate=1:2) for purification to obtain the desired substance.
Product: 34.4 mg
Yield: 22.2%
Description: Colorless viscous liquid
$^1$H-NMR (400 MHz, CDCl$_3$) delta:
1.08 (3H, s), 1.29-1.39 (1H, m), 1.63-1.70 (1H, m), 1.71-1.82 (2H, m), 2.16 (1H, t, J=12.8 Hz), 2.39-2.46 (1H, m), 2.80 (1H, dd, J=12.8, 3.3 Hz), 3.47 (1H, d, J=11.1 Hz), 3.62 (1H, d, J=11.1 Hz), 3.80 (1H, s), 4.46 (2H, s), 7.03 (2H, d, J=8.4 Hz), 7.22 (2H, d, J=8.4 Hz), 7.99 (1H, s), 8.30 (1H, s).

Production Example 11

Synthesis of (1RS,2SR,5SR)-5-(3-chlorobenzyl)-2-chloromethyl-2-methyl-1-(1H-1,2,4-triazol-1-ylmethyl)cyclopentanol (Compound No. I-74 (Compound (I), $(R^a)X^a n^a$=CH$_3$, $(R^b)X^b n^b$=CH$_2$Cl, Ym=3-Cl, A=N, isomer type: C))

(1RS,4SR,5RS)-4-(3-Chlorobenzyl)-1-methyl-5-(1H-1,2,4-triazol-1-ylmethyl)-6-oxabicyclo[3,2,0]heptane (Compound No. (XVI)-3, (Compound (XVI), $(R^a)X^a n^a$=CH$_3$, Ym=3-Cl, A=N, isomer type: C)) (370 mg, 1.16 mmol) was dissolved in DMF (7 ml) and heated to 80 degrees C. To this, lithium chloride (589 mg, 13.9 mmol) and p-toluenesulfonic acid monohydrate (264 mg, 1.39 mmol) were added, and stirring was conducted for 135 minutes. After completion of the reaction, the residue was combined with water, and extracted with ethyl acetate. The organic layer was washed with water and saturated brine, and dried over anhydrous sodium sulfate, the solvent was distilled away, and the residue was subjected to silica gel column chromatography (eluent; hexane:ethyl acetate=1:1) for purification to obtain the desired substance.
Product: 309 mg
Yield: 75.2%
Description: Colorless viscous liquid
$^1$H-NMR (CDCl$_3$) delta:
1.19 (3H, s), 1.41-1.53 (2H, m), 1.66-1.75 (2H, m), 1.90-1.99 (2H, m), 2.32-2.41 (2H, m), 3.24 (1H, d, J=10.8 Hz), 3.57 (1H, d, J=10.8 Hz), 4.10 (1H, s), 4.26 (1H, d, J=14.2 Hz), 4.54 (1H, d, J=14.2 Hz), 6.93 (1H, d, J=6.6 Hz), 7.05 (1H, s), 7.13-7.19 (2H, m), 8.02 (1H, s), 8.20 (1H, s).

Production Example 12

Synthesis of (1RS,2SR,5SR)-2-chloromethyl-5-(4-fluorobenzyl)-2-methyl-1-(1H-1,2,4-triazol-1-ylmethyl)cyclopentanol (Compound No. I-77 (Compound (I), $(R^a)X^a n^a$=CH$_3$, $(R^b)X^b n^b$=CH$_2$Cl, Ym=4-F, A=N, isomer type: C))

(1RS,4SR,5RS)-4-(4-Fluorobenzyl)-1-methyl-5-(1H-1,2,4-triazol-1-ylmethyl)-6-oxabicyclo[3,2,0]heptane (Compound No. (XVI)-4, (Compound (XVI), $(R^a)X^a n^a$=CH$_3$, Ym=4-F, A=N, isomer type: C)) (201.1 mg, 0.667 mmol) was dissolved in DMF (2 ml), and heated to 80 degrees C. To this, lithium chloride (339.3 mg, 8.00 mmol) and p-toluenesulfonic acid monohydrate (152.3 mg, 0.800 mmol) were added, and stirring was conducted for 1 hour. After completion of the reaction, the residue was combined with water, and extracted with ethyl acetate. The organic layer was washed with water and saturated brine, and dried over anhydrous sodium sulfate, the solvent was distilled away, and the residue was subjected to silica gel column chromatography (eluent; hexane:ethyl acetate=1:3) for purification to obtain the desired substance.
Product: 224.3 mg
Yield: 99.6%
Description: White solid, Melting point (m.p.) 126.5 degrees C.
$^1$H-NMR (CDCl$_3$) delta:
1.18 (3H, s), 1.41-1.53 (2H, m), 1.65-1.76 (1H, m), 1.89-1.98 (2H, m), 2.28-2.38 (2H, m), 3.26 (1H, d, J=10.8 Hz), 3.57 (1H, d, J=10.8 Hz), 4.05 (1H, s), 4.25 (1H, d, J=14.2 Hz), 4.54 (1H, d, J=14.2 Hz), 6.92 (2H, t, J=8.7 Hz), 7.00 (2H, dd, J=8.7, 5.5 Hz), 8.01 (1H, s), 8.19 (1H, s).

Production Example 13

Synthesis of (1RS,2SR,5SR)-2-chloromethyl-5-benzyl-2-methyl-1-(1H-1,2,4-triazol-1-ylmethyl)cyclopentanol (Compound No. I-73 (Compound (I), $(R^a)X^a n^a$=CH$_3$, $(R^b)X^b n^b$=CH$_2$Cl, Ym=–(m=0), A=N, isomer type: C))

(1RS,4SR,5RS)-4-Benzyl-1-methyl-5-(1H-1,2,4-triazol-1-ylmethyl)-6-oxabicyclo[3,2,0]heptane (Compound No. (XVI)-5, (Compound (XVI), $(R^a)X^a n^a$=CH$_3$, Ym=(m=0), A=N, isomer type: C)) (124.3 mg, 0.439 mmol) was dissolved in DMF (2.5 ml), and heated to 80 degrees C. To this, lithium chloride (223.1 mg, 5.26 mmol) and p-toluenesulfonic acid monohydrate (100.2 mg, 0.526 mmol) were added, and stirring was conducted for 1 hour. After completion of the reaction, the residue was combined with water, and extracted with ethyl acetate. The organic layer was washed with water and saturated brine, and dried over anhydrous sodium sulfate. The solvent was distilled away, and the residue was recrystallized from ethyl acetate/hexane to obtain the desired substance.
Product: 92.1 mg
Yield: 65.6%
Description: Colorless crystal, Melting point (m.p.) 94.3 degrees C.
$^1$H-NMR (CDCl$_3$) delta:
1.18 (3H, s), 1.40-1.56 (2H, m), 1.67-1.77 (1H, m), 1.91-2.04 (2H, m), 2.34-2.43 (2H, m), 3.22 (1H, d, J=10.8 Hz), 3.57 (1H, d, J=10.8 Hz), 4.02 (1H, s), 4.25 (1H, d, J=14.2 Hz), 4.53 (1H, d, J=14.2 Hz), 7.05 (2H, d, J=7.3 Hz), 7.16 (1H, t, J=7.3 Hz), 7.23 (2H, d, J=7.3 Hz), 8.01 (1H, s), 8.19 (1H, s).

Production Example 14

Synthesis of (1RS,2SR,5SR)-5-(4-chlorobenzyl)-2-chloromethyl-2-methyl-1-imidazol-1-ylmethylcyclopentanol ((Compound No. I-244 (Compound (I), $(R^a)X^a n^a = CH_3$, $(R^b)X^b n^b = CH_2Cl$, Ym=4-Cl, A=CH, isomer type: C))

(1RS,4SR,5RS)-4-(4-Chlorobenzyl)-1-methyl-5-(imidazol-1-ylmethyl)-6-oxabicyclo[3,2,0]heptane (Compound No. (XVI)-6, (Compound (XVI), $(R^a)X^a n^a = CH_3$, Ym=4-Cl, A=CH, isomer type: C)) (100.4 mg, 0.317 mmol) was dissolved in DMF (2 ml), and lithium chloride (201.5 mg, 47.5 mmol) and p-toluenesulfonic acid monohydrate (72.4 mg, 0.380 mmol) were added, and stirring was conducted for 1 hour at 80 degrees C. To this, p-toluenesulfonic acid monohydrate (72.4 mg, 0.380 mmol) was further added and stirring was conducted for further 2 hours. After completion of the reaction, DMF was distilled away under reduced pressure, the residue was combined with water, and extracted with ethyl acetate. The organic layer was washed with water and saturated brine, and dried over anhydrous sodium sulfate, the solvent was distilled away, and the residue was recrystallized from ethyl acetate/hexane to obtain the desired substance.

Product: 79.0 mg
Yield: 70.3%
Description: White solid, Melting point (m.p.) 186.5 degrees C.
$^1$H-NMR (400 MHz, CDCl$_3$) delta:
1.20 (3H, s), 1.39-1.53 (2H, m), 1.70-1.81 (1H, m), 1.85-1.93 (1H, m), 1.93 (1H, dd, J=13.1, 3.3 Hz), 2.26 (1H, dd, J=13.1, 11.2 Hz), 2.34-2.42 (2H, m), 3.39 (1H, d, J=11.0 Hz), 3.57 (1H, d, J=11.0 Hz), 4.07 (1H, d, J=14.5 Hz), 4.31 (1H, d, J=14.5 Hz), 6.98 (2H, d, J=8.3 Hz), 7.08-7.11 (2H, m), 7.21 (2H, d, J=8.3 Hz), 7.64 (1H, s).

Production Example 15

Synthesis of (1RS,2SR,5SR)-2-bromomethyl-5-(4-fluorobenzyl)-2-methyl-1-(1H-1,2,4-triazol-1-ylmethyl)cyclopentanol (Compound No. I-601 (Compound (I), $(R^a)X^a n^a = CH_3$, $(R^b)X^b n^b = CH_2Br$, Ym=4-F, A=N, isomer type: C))

(1RS,4SR,5RS)-4-(4-Fluorobenzyl)-1-methyl-5-(1H-1,2,4-triazol-1-ylmethyl)-6-oxabicyclo[3,2,0]heptane (Compound No. (XVI)-4, (Compound (XVI), $(R^a)X^a n^a = CH_3$, Ym=4-F, A=N, isomer type: C)) (79.5 mg, 0.264 mmol) was dissolved in DMF (1.6 ml), lithium bromide (229 mg, 2.64 mmol) and p-toluenesulfonic acid monohydrate (60.2 mg, 0.316 mmol) were added, stirring was conducted for 6.5 hours at room temperature and then for 1.5 hours at 50 degrees C. After completion of the reaction, the residue was combined with water, and extracted with ethyl acetate. The organic layer was washed with water and saturated brine, and dried over anhydrous sodium sulfate, the solvent was distilled away, and the residue was recrystallized from hexane/ethyl acetate for purification to obtain the desired substance.

Product: 75.1 mg
Yield: 74.4%
Description: White solid, Melting point (m.p.) 130.0 degrees C.
$^1$H-NMR (CDCl$_3$) delta:
1.20 (3H, s), 1.42-1.53 (2H, m), 1.65-1.76 (1H, m), 1.91-1.99 (2H, m), 2.30-2.42 (2H, m), 2.95 (1H, d, J=9.9 Hz), 3.54 (1H, d, J=9.9 Hz), 4.08 (1H, s), 4.23 (1H, d, J=14.2 Hz), 4.51 (1H, d, J=14.2 Hz), 6.93 (2H, t, J=8.7 Hz), 7.01 (2H, dd, J=8.7, 5.4 Hz), 8.02 (1H, s), 8.18 (1H, s).

Production Example 16

Synthesis of (1RS,2SR,5SR)-2-bromomethyl-5-benzyl-2-methyl-1-(1H-1,2,4-triazol-1-ylmethyl)cyclopentanol (Compound No. I-602 (Compound (I), $(R^a)X^a n^a = CH_3$, $(R^b)X^b n^b = CH_2Br$, Ym=–(m=0), A=N, isomer type: C))

(1RS,4SR,5RS)-4-Benzyl-1-methyl-5-(1H-1,2,4-triazol-1-ylmethyl)-6-oxabicyclo[3,2,0]heptane (Compound No. (XVI)-5, (Compound (XVI), $(R^a)X^a n^a = CH_3$, Ym=–(m=0), A=N, isomer type: C)) (50.0 mg, 0.176 mmol) was dissolved in DMF (2 ml), lithium bromide (183.9 mg, 2.12 mmol) and p-toluenesulfonic acid monohydrate (40.3 mg, 0.212 mmol) were added, and stirring was conducted at 50 degrees C. for 1 hour and then at room temperature for 18 hours. After completion of the reaction, the residue was combined with water, and extracted with ethyl acetate. The organic layer was washed with water and saturated brine, and dried over anhydrous sodium sulfate. The solvent was distilled away, and the residue was recrystallized from ethyl acetate/hexane to obtain the desired substance.

Product: 28.1 mg
Yield: 43.7%
Description: Colorless crystal, Melting point (m.p.) 103.3 degrees C.
$^1$H-NMR (CDCl$_3$) delta:
1.20 (3H, s), 1.45-1.58 (2H, m), 1.67-1.78 (1H, m), 1.93-2.01 (1H, m), 2.03-2.17 (1H, m), 2.35-2.46 (2H, m), 2.92 (1H, d, J=9.9 Hz), 3.54 (1H, d, J=9.9 Hz), 4.05 (1H, s), 4.24 (1H, d, J=14.2 Hz), 4.50 (1H, d, J=14.2 Hz), 7.07 (2H, d, J=7.3 Hz), 7.15 (1H, t, J=7.3 Hz), 7.24 (2H, d, J=7.3 Hz), 8.01 (1H, s), 8.18 (1H, s).

Compounds (I) listed in Table 14 shown below were synthesized by the methods analogous to Production Examples described above.

TABLE 14

| Compound No. | Description | $^1$H-NMR (400 MHz, CDCl$_3$)δ |
|---|---|---|
| I-97 | Colorless crystal m.p. 76.5° C. | 0.94 (3H, t, J = 7.4 Hz), 1.34-1.51 (2H, m), 1.52-1.64 (4H, m), 1.80-1.88 (1H, m), 2.17 (1H, dd, J = 13.0, 11.4 Hz), 2.26-2.34 (1H, m), 3.50 (1H, d, J = 11.3 Hz), 4.05 (1H, s), 4.11 (1H, d, J = 11.3 Hz), 4.34 (1H, d, J = 14.1 Hz), 4.79 (1H, d, J = 14.1 Hz), 6.96 (2H, d, J = 7.0 Hz), 7.13 (1H, t, J = 7.3 Hz), 7.18-7.23 (2H, m), 8.01 (1H, s), 8.22 (1H, s). |
| I-86 | Colorless crystal m.p. 100.2° C. | 1.18 (3H, s), 1.41-1.57 (2H, m), 1.63-1.74 (1H, m), 1.91-2.10 (2H, m), 2.36-2.47 (2H, m), 3.22 (1H, d, J = 10.8 Hz), 3.59 (1H, d, J = 10.8 Hz), 4.29 (1H, d, J = 14.2 Hz), 4.30 (1H, s), |

TABLE 14-continued

| Compound No. | Description | $^1$H-NMR (400 MHz, CDCl$_3$)δ |
|---|---|---|
| | | 4.56 (1H, d, J = 14.2 Hz), 6.94-6.99 (1H, m), 7.01 (1H, td, J = 7.5, 1.2 Hz), 7.09 (1H, td, J = 7.5, 1.8 Hz), 7.12-7.19 (1H, m), 8.01 (1H, s), 8.20 (1H, s). |
| I-79 | White solid m.p. 117° C. | 1.19 (3H, s), 1.41-1.52 (2H, m), 1.66-1.76 (1H, m), 1.91-1.99 (2H, m), 2.30-2.41 (2H, m), 3.29 (1H, d, J = 10.8 Hz), 3.58 (1H, d, J = 10.8 Hz), 4.07 (1H, s), 4.27 (1H, d, J = 14.2 Hz), 4.56 (1H, d, J = 14.2 Hz), 7.04-7.10 (4H, m), 8.02 (1H, s), 8.20 (1H, s). |
| I-80 | Colorless crystal m.p. 138.5° C. | 1.18 (3H, s), 1.41-1.52 (2H, m), 1.71-1.76 (1H, m), 1.90-2.02 (2H, m), 2.29 (3H, s), 2.31-2.37 (2H, m), 3.20 (1H, d, J = 10.8 Hz), 3.57 (1H, d, J = 10.8 Hz), 3.97 (3H, s), 4.24 (1H, d, J = 14.2 Hz), 4.51 (1H, d, J = 14.2 Hz), 6.95 (2H, d, J = 7.9 Hz), 7.05 (2H, d, J = 7.9 Hz), 8.00 (1H, s), 8.18 (1H, s). |
| I-174 | White solid m.p. 114° C. | 0.81 (3H, s), 1.48-1.55 (1H, m), 1.66-1.96 (3H, m), 2.32-2.54 (3H, m), 3.53 (1H, d, J = 11.1 Hz), 3.63 (1H, d, J = 11.1 Hz), 4.06 (1H, s), 4.26 (1H, d, J = 14.2 Hz), 4.39 (1H, d, J = 14.2 Hz), 6.98 (1H, d, J = 6.9 Hz), 7.10 (1H, brs), 7.13-7.20 (2H, m), 7.99 (1H, s), 8.22 (1H, s). |
| I-374 | Colorless crystal | 1.24 (3H, s), 1.36-1.45 (1H, m), 1.63-1.69 (1H, m), 1.77-1.20 (1H, m), 2.27-2.37 (2H, m), 3.33 (1H, dd, J = 9.5, 2.3 Hz), 3.57 (1H, d, J = 10.8 Hz), 3.66 (1H, d, J = 10.8 Hz), 4.36 (1H, s), 4.47 (1H, d, J = 14.2 Hz), 4.61 (1H, d, J = 14.2 Hz), 6.92 (1H, dt, J = 6.4, 2.1 Hz), 7.06 (1H, brs), 7.14-7.27 (2H, m), 7.97 (1H, s), 8.21 (1H, s). |
| I-88 | White solid m.p. 123° C. | 1.18 (3H, s), 1.41-1.47 (2H, m), 1.63-1.69 (1H, m), 1.91-1.99 (2H, m), 2.36-2.39 (2H, m), 3.26 (1H, d, J = 10.8 Hz), 3.58 (1H, d, J = 10.8 Hz), 4.29 (1H, d, J = 14.2 Hz), 4.34 (1H, s), 4.57 (1H, d, J = 14.2 Hz), 6.70-6.78 (2H, m), 7.01-7.07 (1H, m), 8.02 (1H, s), 8.20 (1H, s). |
| I-82 | Colorless viscous oil | 1.20 (3H, s), 1.44-1.49 (1H, m), 1.74-1.83 (1H, m), 1.93-2.05 (2H, m), 2.37-2.46 (2H, m), 3.24 (1H, d, J = 10.8 Hz), 3.59 (1H, d, J = 10.8 Hz), 4.05 (1H, s), 4.28 (1H, d, J = 14.2 Hz), 4.55 (1H, d, J = 14.2 Hz), 7.13 (2H, d, J = 8.2 Hz), 7.32 (1H, t, J = 7.3 Hz), 7.42 (2H, dd, J = 7.6, 7.3 Hz), 7.47 (2H, d, J = 8.2 Hz), 7.55 (2H, d, J = 7.1 Hz), 8.02 (1H, s), 8.20 (1H, s). |

Intermediate compounds (II) employed above are produced as described below.

[Chem. 29]

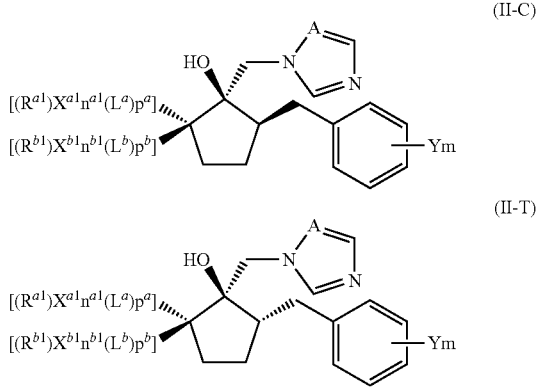

TABLE 15

| Compound No. | $(R^{a1})X^{a1}n^{a1}(L^a)p^{a\ 4)}$ | $(R^{b1})X^{b1}n^{b1}(L^b)p^{b\ 5)}$ | Ym$^{3)}$ | A | Type |
|---|---|---|---|---|---|
| II-1 | CH$_3$ | CH$_2$OTos | 4-Cl | N | C |
| II-2 | CH$_2$OTos | CH$_3$ | 4-Cl | N | C |
| II-3 | CH$_2$CH$_2$OTos | CH$_3$ | 4-Cl | N | C |
| II-4 | CH$_2$CH$_3$ | CH$_2$OTos | 4-Cl | N | C |
| II-5 | CH$_2$OMs | CH$_2$OMs | 4-Cl | N | C |
| II-6 | CH$_2$OTos | CH$_3$ | 4-Cl | N | T |

The tables can be understood as described below.

4): $(R^{a1})X^{a1}n^{a1}(L^a)p^a$ is indicated as a single substituent. Unless $R^{a1}$ is a hydrogen atom, it should be understood that the hydrogen atom-deficient carbon atom on the left end of $(R^{a1})X^{a1}n^{a1}(L^a)p^a$ serves to the binding to the cyclopentane ring in Compound (II). For example, in Compound No. II-1, $(R^{a1})$=methyl group, $n^{a1}$=0, $p^a$=0.

5): $(R^{b1})X^{b1}n^{b1}(L^b)p^b$ is indicated as a single substituent. Unless $R^{b1}$ is a hydrogen atom, it should be understood that the hydrogen atom-deficient carbon atom on the left end of $(R^{b1})X^{b1}n^{b1}(L^b)p^b$ serves to the binding to the cyclopentane ring in Compound (II). For example, in Compound No. II-1, $(R^{b1})$=methyl group, $n^{b2}$=0, $L^b$=OTos, $p^b$=1.

3): The number before "-" indicates the binding position when the carbon atom binding to the carbon atom binding to the cyclopentane ring is regarded as being in 1-position in the case of having a substituent on a phenyl ring.

Reference Production Example 1

(1RS,2RS,3SR)-p-toluenesulfonic acid 3-(4-chlorobenzyl)-2-hydroxy-1-methyl-2-(1H-1,2,4-triazol-1-ylmethyl)cyclopentylmethyl ester (Compound No. II-1 (Compound (II), $(R^{a1})X^{a1}n^{a1}$ $(L^a)p^a$=$CH_3$, $(R^{b1})X^{b1}n^{b1}$ $(L^b)p^bR^{b1}$=$CH_2OTos$, Ym=4-Cl, A=N, isomer type: C))

Under argon atmosphere, sodium hydride (73 mg (60%, 1.83 mmol) was washed with hexane, and then suspended in dehydrated THF (4 ml) and cooled with ice/water. Then, (1RS,2RS,5SR)-5-(4-chlorobenzyl)-2-hydroxymethyl-2-methyl-1-(1H-1,2,4-triazol-1-ylmethyl)cyclopentanol (Compound No. VI-1 (Compound (VI), $(R^{a2})X^{a2}n^{a2}$ (OH) $p^{a1}$=$CH_3$, $(R^{b2})X^{b2}n^{b2}$ (OH)$p^{b1}$=$CH_2OH$, Ym=4-Cl, A=N, isomer type: C)) (510 mg, 1.52 mmol) dissolved in dehydrated THF (5 ml) was added dropwise. After returning to room temperature, stirring was conducted for 30 minutes. After cooling with ice/water again, p-toluenesulfonyl chloride (380 mg, 1.97 mmol) was added, and stirring was conducted at the same temperature for 1.5 hours and then at room temperature for 0.5 hour. To the reaction solution, water (20 ml) was added, the reaction was stopped, and then partition with ethyl acetate (100 ml) was conducted. The organic layer was washed with saturated brine (20 ml×3), and then dried over anhydrous sodium sulfate, and then concentrated. Silica gel chromatography (eluent; hexane: ethyl acetate=2:3) was employed for purification to obtain the desired substance.

Product: 0.41 g
Yield: 55%
Description: White solid m.p. 69 degrees C.
$^1$H-NMR (400 MHz, $CDCl_3$) delta:
1.09 (3H, s), 1.24-1.30 (1H, m), 1.35-1.45 (1H, m), 1.60-1.80 (3H, m), 2.16-2.32 (2H, m), 3.85 (1H, d, J=9.4 Hz), 3.97 (s, 1H), 3.99 (1H, d, J=9.4 Hz), 4.23 (1H, d, J=14.2 Hz), 4.43 (1H, d, J=14.2 Hz), 6.91 (2H, d, J=8.4 Hz), 7.17 (2H, d, J=8.4 Hz), 7.36 (2H, d, J=8.0 Hz), 7.76 (2H, d, J=8.3 Hz), 7.96 (1H, s), 8.16 (1H, s).

Reference Production Example 2

Synthesis of (1RS,2SR,3RS)-p-toluenesulfonic acid 3-(4-chlorobenzyl)-2-hydroxy-1-methyl-2-(1H-1,2,4-triazol-1-ylmethyl)cyclopentylmethyl ester (Compound No. II-2 (Compound (II), $(R^{a1})X^{a1}n^{a1}$ $(L^a)p^a$=$CH_2OTos$, $(R^{b1})X^{b1}n^{b1}$ $(L^b)p^bR^{b1}$=$CH_3$, Ym=4-Cl, A=N, isomer type: C))

Under argon atmosphere, (1RS,2SR,5SR)-5-(4-chlorobenzyl)-2-hydroxymethyl-2-methyl-1-(1H-1,2,4-triazol-1-ylmethyl)cyclopentanol (Compound No. VI-2 (Compound (VI), $(R^{a2})X^{a2}n^{a2}$ (OH)$p^{a1}$=$CH_2OH$, $(R^{b2})X^{b2}n^{b2}$ (OH)$p^{b1}$=$CH_3$, Ym=4-Cl, A=N, isomer type: C)) (0.205 g, 0.610 mmol) was dissolved in dehydrated THF, and, while cooling with ice, sodium hydride (18 mg, 0.733 mmol) was added, and stirring was conducted for 0.5 hour at room temperature. To this, p-toluenesulfonyl chloride (0.140 g, 0.733 mmol) was added and stirring was conducted at room temperature for 2 hours, and then sodium hydride (12 mg, 0.51 mmol) was added, and stirring was conducted for 2 hours. After completion of the reaction, water (5 ml) and ethyl acetate (25 ml) were added, and partition was conducted. The organic layer was washed with saturated brine (5 ml×3), and then dried over anhydrous sodium sulfate, and then concentrated. Silica gel column chromatography (eluent; hexane: ethyl acetate=1:1) was employed for purification to obtain the desired substance.

Product: 0.21 g
Yield: 69%
Description: White solid
$^1$H-NMR (400 MHz, $CDCl_3$) delta:
0.40 (3H, s), 1.27 (1H, m), 1.50-1.71 (3H, m), 2.27 (1H, m), 2.46 (3H, s), 2.65 (2H, d, J=7.4 Hz), 3.64 (1H, d, J=10.2 Hz), 4.01 (1H, d, J=10.2 Hz), 4.21 (1H, d, J=14.2 Hz), 4.44 (1H, d, J=14.2 Hz), 4.84 (1H, s), 7.08 (2H, d, J=8.3 Hz), 7.24 (2H, d, J=8.1 Hz), 7.36 (2H, d, J=8.1 Hz), 7.76 (2H, d, J=8.3 Hz), 7.96 (1H, s), 8.32 (1H, s).

Reference Production Example 3

Synthesis of p-toluenesulfonic acid 2-[(1RS,2SR,3RS)-3-(4-chlorobenzyl)-2-hydroxy-1-methyl-2-(1H-1,2,4-triazol-1-ylmethyl)cyclopentyl]ethyl ester (Compound No. II-3 (Compound (II), $(R^{a1})X^{a1}n^{a1}$ $(L^a)p^a$=$CH_2CH_2OTos$, $(R^{b1})X^{b1}n^{b1}$ $(L^b)p^bR^{b1}$=$CH_3$, Ym=4-Cl, A=N, isomer type: C))

(1RS,2SR,5SR)-5-(4-Chlorobenzyl)-2-hydroxyethyl-2-methyl-1-(1H-1,2,4-triazol-1-ylmethyl)cyclopentanol (Compound No. VI-3 (Compound (VI), $(R^{a2})X^{a2}n^{a2}$ (OH) $p^{a1}$=$CH_2CH_2OH$, $(R^{b2})X^{b2}n^{b2}$ (OH)$p^{b1}$=$CH_3$, Ym=4-Cl, A=N, isomer type: C)) (32.4 mg, 0.089 mmol) and p-toluenesulfonyl chloride (14.7 mg, 0.085 mmol) were dissolved in THF (1 ml), sodium hydride (60% oil dispersion) (3.1 mg, 0.077 mmol) was added, and stirring was conducted at room temperature for 19 hours. This was stirred for 3.5 hours in an oil bath at 35 degrees C., and then sodium hydride (60% oil dispersion) (0.5 mg, 0.013 mmol) was added, and stirring was conducted further for 30 minutes. After completion of the reaction, the solution was poured into ice/water and extracted with chloroform. The organic layer was washed with an aqueous solution of sodium carbonate and saturated brine, and then dried over sodium sulfate and the solvent was distilled away to obtain a crude intended substance.

Product: 44.3 mg
Yield: 69%
Description: White solid
$^1$H-NMR (400 MHz, $CDCl_3$) delta:
0.59 (3H, s), 1.36-1.47 (2H, m), 1.54-1.69 (2H, m), 1.76 (2H, t, J=7.5 Hz), 2.10-2.20 (1H, m), 2.38 (1H, dd, J=13.7, 5.1 Hz), 2.43-2.47 (1H, m), 2.44 (3H, s), 3.94 (1H, s), 4.06-4.22 (3H, m), 4.30 (1H, d, J=12.4 Hz), 6.99 (1H, d, J=8.4 Hz), 7.21 (1H, d, J=8.4 Hz), 7.34 (1H, d, J=8.3 Hz), 7.77 (1H, d, J=8.3 Hz), 7.96 (1H, s), 8.11 (1H, s).

Reference Production Example 4

Synthesis of (1RS,2RS,3SR)-p-toluenesulfonic acid 3-(4-chlorobenzyl)-1-ethyl-2-hydroxy-2-(1H-1,2,4-triazol-1-yl)methylcyclopentylmethyl ester (Compound No. II-4 (Compound (II), $(R^{a1})X^{a1}n^{a1}$ $(L^a)p^a$=$CH_2CH_3$, $(R^{b1})X^{b1}n^{b1}$ $(L^b)p^bR^{b1}$=$CH_2OTos$, Ym=4-Cl, A=N, isomer type: C))

(1RS,2RS,5SR)-5-(Chlorobenzyl)-2-ethyl-2-hydroxymethyl-1-(1H-1,2,4-triazol-1-ylmethyl)cyclopentanol (Compound No. VI-4 (Compound (VI), $(R^{a2})X^{a2}n^{a2}$ (OH) $p^{a1}$=$CH_2CH_3$, $(R^{b2})X^{b2}n^{b2}$ (OH)$p^{b1}$=$CH_2OH$, Ym=4-Cl, A=N, isomer type: C)) (62.3 mg, 0.178 mmol) was dissolved in THF (1 ml), sodium hydride (7.9 mg, 0.198 mmol) was added, and stirring was conducted at room temperature for 30 minutes. This was cooled to −15 degrees C., tosyl chloride (40.8 mg, 0.214 mmol) was added, and stirring was conducted for 1.5 hours while warming to room temperature.

After completion of the reaction, water was added and the solution was extracted with ethyl acetate, and washed with saturated brine. The organic layer was dried over anhydrous sodium sulfate, and then the solvent was distilled away, and the residue was subjected to silica gel column chromatography (eluent; hexane: ethyl acetate=2:3) for purification to obtain the desired substance.

Product: 57.6 mg
Yield: 64.2%
Description: White foam
$^1$H-NMR (400 MHz, CDCl$_3$) delta:
0.82 (3H, t, J=7.3 Hz), 1.30-1.40 (1H, m), 1.42-1.50 (3H, m), 1.50-1.61 (1H, m), 1.67-1.77 (1H, m), 2.10 (1H, dd, J=14.6, 11.4 Hz), 2.19-2.27 (1H, m), 2.47 (3H, s), 3.91 (1H, d, J=9.5 Hz), 3.97 (1H, s), 4.31 (1H, d, J=14.2 Hz), 4.32 (1H, d, J=9.5 Hz), 4.52 (1H, d, J=14.2 Hz), 6.86 (2H, d, J=8.4 Hz), 7.15 (2H, d, J=8.4 Hz), 7.37 (2H, d, J=8.0 Hz), 7.81 (2H, d, J=8.0 Hz), 7.97 (1H, s), 8.16 (1H, s).

Reference Production Example 5

Synthesis of cis-5-(4-chlorobenzyl)-2,2-bis(methanesulfonyloxymethyl)-1-(1H-1,2,4-triazol-1-yl)methylcyclopentanol (Compound No. II-5 (Compound (II), $(R^{a1})X^{a1}n^{a1}$ $(L^a)p^a$=CH$_2$OMs, $(R^{b1})X^{b1}n^{b1}$ $(L^b)$ $p^b R^{b1}$=CH$_2$OMs, Ym=4-Cl, A=N, isomer type: C))

cis-5-(4-Chlorobenzyl)-2,2-bis(hydroxymethyl)-1-(1H-1,2,4-triazol-1-yl)methylcyclopentanol (Compound No. VI-5 (Compound (VI), $(R^{a2})X^{a2}n^{a2}$ (OH)p$^a$=CH$_2$OH, $(R^{b2})X^{b2}n^{b2}$ (OH)p$^{b1}$=CH$_2$OH, Ym=4-Cl, A=N, isomer type: C)) (50.0 mg, 0.142 mmol) was dissolved in THF (1.5 ml), triethylamine (0.0598 ml, 0.426 mmol) was added, and the solution was cooled to 0 degrees C. in an ice bath. To this, methanesulfonyl chloride (0.0246 ml, 0.341 mmol) was added dropwise, and stirring was conducted for 3 hours while warming to room temperature. After completion of the reaction, water was added and extraction with ethyl acetate was conducted. This was washed with a dilute aqueous solution of sodium hydroxide and saturated brine and dried over anhydrous sodium sulfate. The solvent was distilled away, and the residue was dried in vacuo to obtain a crude intended substance.

Crude product: 76.9 mg
Crude yield: 107%
Description: Colorless viscous liquid
$^1$H-NMR (CDCl$_3$) delta:
1.48-1.58 (1H, m), 1.59-1.73 (2H, m), 1.87-1.96 (1H, m), 2.22-2.34 (2H, m), 2.53 (1H, dd, J=12.7, 9.5 Hz), 2.97 (3H, s), 3.07 (3H, s), 3.92 (1H, d, J=9.9 Hz), 4.15 (1H, d, J=10.4 Hz), 4.20 (1H, d, J=9.9 Hz), 4.25 (1H, d, J=10.4 Hz), 4.28 (1H, d, J=14.3 Hz), 4.54 (1H, d, J=14.3 Hz), 5.18 (1H, s), 7.02 (2H, d, J=8.4 Hz), 7.23 (2H, d, J=8.4 Hz), 8.03 (1H, s), 8.34 (1H, s).

Reference Production Example 6

Synthesis of (1RS,2SR,5RS)-5-(4-chlorobenzyl)-2-(p-toluenesulfonyl)oxymethyl-2-methyl-1-[1,2,4]triazol-1-ylmethylcyclopentanol (Compound No. II-6 (Compound (II), $(R^{a1})X^{a1}n^{a1}$ $(L^a)$ $p^a$=CH$_2$OTos, $(R^{b1}X^{b1}n^{b1}$ $(L^b)p^b R^{b1}$=CH$_3$, Ym=4-Cl, A=N, isomer type: T))

(1RS,2SR,5RS)-5-(4-Chlorobenzyl)-2-hydroxymethyl-2-methyl-1-(1H-1,2,4-triazol-1-ylmethyl)cyclopentanol (Compound No. VI-2 (Compound (VI), $(R^{a2})X^{a2}n^{a2}$ (OH) $p^{a1}$=CH$_2$OH, $(R^{b2})X^{b2}n^{b2}$ (OH)$p^{b1}$=CH$_3$, Ym=4-Cl, A=N, isomer type: T)) (200 mg, 0.596 mmol) was dissolved in THF (4 ml), sodium hydride (23.8 mg, 0.596 mmol) was added, and stirring was conducted at 50 degrees C. for 40 minutes. To this, while cooling in an ice bath, p-toluenesulfonyl chloride (125 mg, 0.656 mmol) was added and stirring was conducted at room temperature for 1.5 hours. After completion of the reaction, the solvent was distilled away, and water was added and extraction with ethyl acetate was conducted. The organic layer was washed with saturated brine, dried over anhydrous sodium sulfate. The solvent was distilled away, and then the residue was subjected to silica gel column chromatography (eluent; hexane:ethyl acetate=1:3) for purification to obtain the desired substance.

Product: 242.8 mg
Yield: 83.2%
Description: Colorless solid
$^1$H-NMR (CDCl$_3$) delta:
0.75 (3H, s), 1.21-1.30 (1H, m), 1.49-1.57 (1H, m), 1.63-1.77 (2H, m), 2.18 (1H, t, J=12.8 Hz), 2.38-2.46 (1H, m), 2.46 (3H, s), 2.84 (1H, dd, J=12.8, 3.9 Hz), 3.74 (1H, d, J=10.0 Hz), 3.98 (1H, d, J=10.0 Hz), 4.35 (1H, d, J=14.2 Hz), 4.43 (1H, d, J=14.2 Hz), 4.56 (1H, s), 6.99 (2H, d, J=8.4 Hz), 7.22 (2H, d, J=8.4 Hz), 7.37 (2H, d, J=8.2 Hz), 7.78 (2H, d, J=8.2 Hz), 7.95 (1H, s), 8.28 (1H, s).

The intermediate compounds (VI) employed above can be produced by Reference Production Example 7 described below and analogous methods as well as methods known in references.

Reference Production Example 7

Synthesis of 5-(4-chlorobenzyl)-2-hydroxymethyl-2-methyl-1-(1H-1,2,4-triazol-1-ylmethyl)cyclopentanol (1) Synthesis of Intermediate 1-(4-chlorobenzyl)-3-methyl-3-hydroxymethyl-2-oxocyclopentane carboxylic acid methyl ester (Compound No. XI-1 (Compound (XI), $R^1$=CH$_3$, $R^2$=CH$_3$, Ym=4-Cl))

To 1-(4-chlorobenzyl)-3-methyl-2-oxocyclopentane carboxylic acid methyl ester (1.12 g, 4.0 mmol), a 37% aqueous solution of formaldehyde (0.90 ml, 12 mmol) and potassium carbonate (276 mg, 2.0 mmol) were added, and vigorous stirring was conducted at room temperature for 4 hours. After completion of the reaction, water was added and, extraction with ethyl acetate (30 ml) was conducted. The organic layer was washed with saturated brine (10 ml), dried over anhydrous sodium sulfate. The solvent was distilled away, and the residue was purified by silica gel column chromatography (eluent; hexane:ethyl acetate=3:2), and the title compound was obtained as two isomers.

Isomer (a)
Product: 227 mg
Yield: 18%
Description: Colorless oil
$^1$H-NMR (400 MHz, CDCl$_3$) delta:
1.10 (3H, s), 1.69 (1H, brdd, J=7.2, 4.6 Hz), 1.72-1.78 (1H, m), 1.84-1.91 (1H, m), 1.91-2.00 (1H, m), 2.39-2.47 (1H, m), 3.00 (1H, d, J=13.9 Hz), 3.20 (1H, d, J=13.9 Hz), 3.25 (1H, dd, J=10.8, 4.6 Hz), 3.45 (1H, dd, J=10.8, 7.2 Hz), 3.73 (3H, s), 7.09 (2H, d, J=8.5 Hz), 7.23 (2H, d, J=8.5 Hz).

Isomer (b)
Product: 953 mg
Yield: 76%
Description: White solid

¹H-NMR (400 MHz, CDCl₃) delta:
0.71 (3H, s), 1.46 (1H, ddd, J=12.9, 7.2, 3.0 Hz), 1.88-1.95 (1H, m), 1.92 (1H, brs), 2.04-2.15 (1H, m), 2.38 (1H, ddd, J=13.3, 7.2, 3.0 Hz), 3.14 (2H, s), 3.45 (1H, dd, J=10.9, 5.7 Hz), 3.63 (1H, dd, J=10.9, 6.8 Hz), 3.72 (3H, s), 7.05 (2H, d, J=8.5 Hz), 7.24 (2H, d, J=8.5 Hz).

Similar production methods were employed to synthesize Compounds (XI) listed in Table 16 shown below.

TABLE 16

| Compound No. | R¹ | R² | Ym | Description | ¹H-NMR (400 MHz, CDCl₃)δ |
|---|---|---|---|---|---|
| XI-2 Isomer-(a) | CH₃ | CH₃ | 4-F | White solid | 0.68 (3H, s), 1.45 (1H, ddd, J = 12.7, 7.1, 3.0 Hz), 1.88-1.98 (2H, m), 2.04-2.13 (1H, m), 2.38 (1H, ddd, J = 13.2, 7.1, 3.0 Hz), 3.12 (1H, d, J = 13.8 Hz), 3.16 (1H, d, J = 13.8 Hz), 3.45 (1H, dd, J = 11.0, 5.8 Hz), 3.62 (1H, dd, J = 11.0, 6.9 Hz), 3.72 (3H, s), 6.95 (2H, t, J = 8.7 Hz), 7.08 (2H, dd, J = 8.7, 5.4 Hz). |
| XI-2 Isomer-(b) | CH₃ | CH₃ | 4-F | Colorless viscous liquid | 1.10 (3H, s), 1.65-1.70 (1H, m), 1.72 (1H, dt, J = 13.3, 7.3 Hz), 1.80-1.88 (1H, m), 1.98 (1H, dt, J = 13.6, 7.3 Hz), 2.37-2.45 (1H, m), 3.03 (1H, d, J = 13.9 Hz), 3.18 (1H, d, J = 13.9 Hz), 3.22 (1H, dd, J = 10.8, 4.6 Hz), 3.42 (1H, dd, J = 10.8, 7.3 Hz), 3.73 (3H, s), 6.95 (2H, t, J = 8.7 Hz), 7.12 (2H, dd, J = 8.7, 5.5 Hz). |
| XI-3 Isomer-(a) | CH₃ | CH₃ | 3-Cl | Colorless viscous liquid | 0.72 (3H, s), 1.46 (1H, ddd, J = 12.9, 7.1, 3.0 Hz), 1.68-1.93 (1H, m), 2.00-2.05 (1H, m), 2.06-2.17 (1H, m), 2.39 (1H, ddd, J = 13.3, 7.1, 3.0 Hz), 3.12 (1H, d, J = 13.7 Hz), 3.16 (1H, d, J = 13.7 Hz), 3.46 (1H, dd, J = 10.9, 5.5 Hz), 3.63 (1H, dd, J = 10.9, 6.7 Hz), 3.72 (3H, s), 6.99 (1H, d, J = 6.2 Hz), 7.11 (1H, s), 7.17-7.23 (2H, m). |
| XI-3 Isomer-(b) | CH₃ | CH₃ | 3-Cl | Colorless viscous liquid | 1.10 (3H, s), 1.72-1.79 (2H, m), 1.84-2.04 (2H, m), 2.39-2.46 (1H, m), 3.01 (1H, d, J = 13.9 Hz), 3.21 (1H, d, J = 13.9 Hz), 3.25 (1H, dd, J = 10.8, 4.5 Hz), 3.46 (1H, dd, J = 10.8, 7.1 Hz), 3.73 (3H, s), 7.03 (1H, d, J = 6.1 Hz), 7.16 (1H, s), 7.18-7.23 (2H, m). |
| XI-4 Isomer-(a) | CH₃CH₂ | CH₃ | 4-Cl | Colorless viscous liquid | 0.75 (3H, t, J = 7.5 Hz), 1.10 (1H, dq, J = 14.5, 7.5 Hz), 1.33 (1H, dq, J = 14.5, 7.5 Hz), 1.65-1.71 (1H, m), 1.79-1.86 (1H, m), 1.87-1.98 (2H, m), 2.36-2.43 (1H, m), 3.02 (1H, d, J = 13.8 Hz), 3.20 (1H, d, J = 13.8 Hz), 3.47 (1H, dd, J = 11.0, 4.5 Hz), 3.63 (1H, dd, J = 11.0, 7.3 Hz), 3.71 (3H, s), 7.04 (2H, d, J = 8.5 Hz), 7.23 (2H, d, J = 8.5 Hz). |
| XI-4 Isomer-(b) | CH₃CH₂ | CH₃ | 4-Cl | Colorless viscous liquid | 0.81 (3H, t, J = 7.5 Hz), 1.45-1.65 (2H, m), 1.67-1.76 (2H, m), 1.85-1.95 (2H, m), 2.37-2.45 (1H, m), 2.99 (1H, d, J = 13.8 Hz), 3.23 (1H, d, J = 13.8 Hz), 3.26 (1H, dd, J = 10.8, 4.0 Hz), 3.51 (1H, dd, J = 10.8, 7.6 Hz), 3.71 (3H, s), 7.07 (2H, d, J = 8.4 Hz), 7.23 (2H, d, J = 8.4 Hz). |
| XI-5 Isomer-(a) | CH₃ | CH₃ | 2-F | Colorless viscous liquid | 0.74 (3H, s), 1.50 (1H, ddd, J = 12.9, 7.1, 3.0 Hz), 1.85-1.99 (2H, m), 2.03-2.14 (1H, m), 2.38 (1H, ddd, J = 13.5, 7.1, 3.0 Hz), 3.10 (1H, dd, J = 13.8, 1.5 Hz), 3.39 (1H, d, J = 13.8 Hz), 3.46 (1H, dd, J = 11.0, 5.6 Hz), 3.63 (1H, dd, J = 11.0, 6.8 Hz), 3.73 (3H, s), 6.99-7.06 (2H, m), 7.08-7.14 (1H, m), 7.17-7.25 (1H, m). |
| XI-5 Isomer-(b) | CH₃ | CH₃ | 2-F | Colorless viscous liquid | 1.11 (3H, s), 1.72-1.80 (1H, m), 1.86-2.01 (3H, m), 2.40-2.48 (1H, m), 3.09 (1H, dd, J = 14.0, 1.2 Hz), 3.25 (1H, dd, J = 10.9, 4.5 Hz), 3.33 (1H, dd, J = 14.0, 1.2 Hz), 3.44 (1H, dd, J = 10.9, 7.3 Hz), 3.74 (3H, s), 6.98-7.07 (2H, m), 7.15-7.25 (2H, m). |
| XI-6 Isomer-(a) | CH₃ | CH₃ | 4-OCF3 | Colorless viscous liquid | 0.68 (3H, s), 1.43-1.49 (1H, m), 1.88-1.95 (1H, m), 1.98-2.01 (1H, m), 2.08-2.16 (1H, m), 2.36-2.42 (1H, m), 3.17 (2H, s), 3.45 (1H, dd, J = 10.9, 5.7 Hz), 3.63 (1H, dd, J = 11.0, 6.8 Hz), 3.72 (3H, s), 7.10-7.16 (4H, m). |
| XI-6 Isomer-(b) | CH₃ | CH₃ | 4-OCF3 | Colorless viscous liquid | 1.10 (3H, s), 1.72-1.80 (2H, m), 1.88-2.00 (2H, m), 2.38-2.46 (1H, m), 3.02 (1H, d, J = 13.9 Hz), 3.24 (1H, d, J = 13.9 Hz), 3.26 (1H, dd, J = 10.7, 4.6 Hz), 3.47 (1H, dd, J = 10.7, 7.0 Hz), 3.73 (3H, s), 7.10-7.20 (4H, m). |
| XI-7 Isomer-(a) | CH₃ | CH₃ | 4-CH3 | Colorless viscous liquid | 0.69 (3H, s), 1.39-1.44 (1H, m), 1.91-1.99 (1H, m), 2.03-2.11 (1H, m), 2.15-2.18 (1H, m), 2.30 (3H, s), 2.33-2.39 (1H, m), 3.13 (2H, s), 3.45 (1H, dd, J = 10.9, 5.2 Hz), 3.61 (1H, dd, J = 11.0, 6.5 Hz), 3.71 (3H, s), 6.98 (2H, d, J = 8.0 Hz), 7.05 (2H, d, J = 7.9 Hz). |
| XI-7 Isomer-(b) | CH₃ | CH₃ | 4-CH3 | Colorless viscous liquid | 1.09 (3H, s), 1.67-1.83 (3H, m), 1.98-2.05 (1H, m), 2.30 (3H, s), 2.31-2.43 (1H, m), 3.05 (1H, d, J = 13.8 Hz), 3.16 (1H, d, J = 13.8 Hz), 3.18 (1H, dd, J = 10.9, 4.9 Hz), 3.38 (1H, dd, J = 10.9, 7.4 Hz), 3.73 (3H, s), 7.02 (2H, d, J = 8.1 Hz), 7.07 (2H, d, J = 8.1 Hz). |
| XI-8 Isomer-(a) | CH₃ | CH₃ | 2,4-F | Colorless viscous liquid | 0.76 (3H, s), 1.53 (1H, ddd, J = 12.9, 7.1, 2.9 Hz), 1.82-1.90 (1H, m), 1.96 (1H, dd, J = 6.8, 5.7 Hz), 2.08-2.17 (1H, m), 2.42 (1H, ddd, J = 13.5, 7.1, 2.9 Hz), 3.06 (1H, dd, J = 14.0, 1.7 Hz), 3.33 (1H, d, J = 14.0 Hz), 3.46 (1H, dd, J = 10.9, 5.7 Hz), 3.64 (1H, dd, J = 10.9, 6.8 Hz), 3.72 (3H, s), 6.76-6.82 (2H, m), 7.07-7.13 (1H, m). |

TABLE 16-continued

| Compound No. | $R^1$ | $R^2$ | Ym | Description | $^1$H-NMR (400 MHz, CDCl$_3$)δ |
|---|---|---|---|---|---|
| XI-8 Isomer-(b) | CH$_3$ | CH$_3$ | 2,4-F | Colorless viscous liquid | 1.11 (3H, s), 1.74-1.81 (2H, m), 1.89-1.99 (2H, m), 2.41-2.48 (1H, m), 3.04 (1H, d, J = 14.2 Hz), 3.27 (1H, d, J = 14.2 Hz), 3.30 (1H, dd, J = 10.8, 4.5 Hz), 3.48 (1H, dd, J = 10.8, 7.3 Hz), 3.74 (3H, s), 6.75-6.81 (2H, m), 7.16-7.22 (1H, m). |

(2) Synthesis of Intermediate 5-(4-chlorobenzyl)-2-methoxymethoxymethyl-2-methylcyclopentanone (Compound (IX), $R^1$=CH$_3$, Ym=4-Cl, G=CH$_2$OCH$_3$)

1-(4-Chlorobenzyl)-3-methyl-3-hydroxymethyl-2-oxocyclopentane carboxylic acid methyl ester (Compound (XI), $R^1$=CH$_3$, $R^2$=CH$_3$, Ym=4-Cl) (186 mg, 0.60 mmol) was dissolved in methylene chloride (5.6 ml), and dimethoxymethane (2.8 ml) was added. This was cooled in a water bath, diphosphorus pentoxide (372 mg) was added and vigorous stirring was conducted at room temperature for 10 minutes. After completion of the reaction, saturated brine was combined with the reaction solution, and extraction with diethyl ether was conducted. The organic layer was washed with saturated brine, dried over anhydrous sodium sulfate. The solvent was distilled away and dried under reduced pressure to obtain a crude 1-(4-chlorobenzyl)-3-methoxymethoxymethyl-3-methyl-2-oxocyclopentane carboxylic acid methyl ester (Compound (X), $R^1$=CH$_3$, $R^2$=CH$_3$, Ym=4-Cl, G=CH$_2$OCH$_2$OCH$_3$) (195 mg). From this, an aliquot (188.8 mg) was dissolved in isopropanol (0.53 ml), a 2M aqueous solution of sodium hydroxide (0.53 ml, 1.12 mmol) was added, and stirring was conducted at 60 degrees C. for 1 hour. After completion of the reaction, water was added and extraction with ethyl acetate was conducted. The organic layer was washed with saturated brine, dried over anhydrous sodium sulfate. The solvent was distilled away, and the residue was purified by silica gel column chromatography (eluent; hexane:ethyl acetate=7:1) to obtain the desired substance as a mixture of two isomers (Isomer (a):Isomer (b)=36:65).

Product: 104.1 mg
Yield: 66%
Description: Colorless oil
$^1$H-NMR (400 MHz, CDCl$_3$) delta:
Isomer (a)
1.04 (3H, s), 1.60-1.71 (2H, m), 1.89-1.96 (1H, m), 2.17-2.23 (1H, m), 2.44-2.55 (2H, m), 3.06 (1H, dd, J=13.1, 3.6 Hz), 3.27 (1H, d, J=8.9 Hz), 3.31 (3H, s), 3.52 (1H, d, J=8.9 Hz), 4.51 (1H, d, J=10.1 Hz), 4.52 (1H, d, J=10.1 Hz), 7.10 (2H, d, J=8.4 Hz), 7.24 (2H, d, J=8.4 Hz).
Isomer (b)
0.84 (3H, s), 1.49 (1H, qd, J=12.2, 6.9 Hz), 1.64 (1H, ddd, J=12.7, 6.8, 1.2 Hz), 1.96-2.04 (1H, m), 2.08-2.17 (1H, m), 2.36-2.45 (1H, m), 2.61 (1H, dd, J=14.0, 8.7 Hz), 3.09 (1H, dd, J=14.0, 2.2 Hz), 3.31 (3H, s), 3.32 (1H, d, J=9.1 Hz), 3.62 (1H, d, J=9.1 Hz), 4.53 (1H, d, J=10.8 Hz), 4.54 (1H, d, J=10.8 Hz), 7.09 (2H, d, J=8.5 Hz), 7.23 (2H, d, J=8.5 Hz).

(3) Synthesis of Intermediate 5-(4-chlorobenzyl)-2-methoxymethoxymethyl-2-methyl-1-(1H-1,2,4-triazol-1-ylmethyl)cyclopentanol (Compound (VII), $R^1$=CH$_3$, Ym=4-Cl, G=CH$_2$OCH$_3$, A=N)

1H-1,2,4-Triazole sodium salt (1.196 g, 13.1 mmol) was dissolved in NMP (7 ml), and heated to an internal temperature of 115 degrees C. To this, 5-(4-chlorobenzyl)-2-methoxymethoxymethyl-2-methylcyclopentanone (Compound (IX), $R^1$=CH$_3$, Ym=4-Cl, G=CH$_2$OCH$_3$) (2.60 g, 8.76 mmol) was added, and washed thoroughly with NMP (1.8 ml). After the internal temperature became 115 degrees C. again, sodium t-butoxide (505 mg, 5.26 mmol) and trimethylsulfoxonium bromide (2.2379 g, 1.476 mmol) were added in portions over about 3 hours. After completion of the addition, stirring was conducted at the same temperature for 75 minutes. The reaction solution was cooled to 35 degrees C., and then, to the reaction solution, water was added and extraction with ethyl acetate was conducted. The organic layer was washed with water and saturated brine, and dried over anhydrous sodium sulfate. The solvent was distilled away and the residue was subjected to silica gel column chromatography (eluent; hexane:ethyl acetate=3:1 to 0:1) for purification to obtain the desired substance.

Product: 2.36 g
Yield: 71%
Description: Colorless viscous oil (4) Synthesis of 5-(4-chlorobenzyl)-2-hydroxymethyl-2-methyl-1-(1H-1,2,4-triazol-1-ylmethyl)cyclopentanol (Compound (VI-a)-1, $R^1$=CH$_3$, Ym=4-Cl, A=N)

5-(4-Chlorobenzyl)-2-methoxymethoxymethyl-2-methyl-1-(1H-1,2,4-triazol-1-ylmethyl)cyclopentanol (Compound (VII), $R^1$=CH$_3$, Ym=4-Cl, G=CH$_2$OCH$_3$, A=N) (629 mg, 1.66 mmol) was dissolved in methanol (6.3 ml), 10% hydrogen chloride-methanol (6.3 ml, 1.73 mmol) was added and stirring was conducted at room temperature for 48 hours. After completion of the reaction, the solvent was distilled away, and water was added. After ethyl acetate (80 ml) was added, an aqueous solution of sodium hydroxide was added until the pH became 10. The organic layer was separated, washed with saturated brine, and then dried over anhydrous sodium sulfate. The solvent was distilled away to obtain the title compound (VI-1 (Compound (VI), $(R^{a2})X^{a2}n^{a2}$ (OH)$p^{a1}$=CH$_3$, $(R^{b2})X^{b2}n^{b2}$ (OH)$p^{b1}$=CH$_2$OH, Ym=4-Cl, A=N, isomer type: C): VI-2 (Compound (VI), $(R^{a2})X^{a2}n^{a2}$ (OH)$p^{a1}$=CH$_2$OH, $(R^{b2})X^{b2}n^{b2}$ (OH)$p^{b1}$=CH$_3$, Ym=4-Cl, A=N, isomer type: C): other isomers (isomer type: T)=6:3:1).

Yield: 498 mg
Yield: 89.5%
Description: White solid

By the methods of Reference Production Example described above and the like, the following Compounds (VI) were synthesized.

TABLE 17

| Compound No. | $(R^{a2})X^{a2}n^{a2}(OH)p^{a1}$ [6] | $(R^{b2})X^{b2}n^{b2}(OH)p^{b1}$ [7] | $Ym$ [3] | A | Type |
|---|---|---|---|---|---|
| VI-1 | $CH_3$ | $CH_2OH$ | 4-Cl | N | C |
| VI-2 | $CH_2OH$ | $CH_3$ | 4-Cl | N | C |
| VI-3 | $CH_2CH_2OH$ | $CH_3$ | 4-Cl | N | C |
| VI-4 | $CH_2CH_3$ | $CH_2OH$ | 4-Cl | N | C |
| VI-5 | $CH_2OH$ | $CH_2OH$ | 4-Cl | N | C |
| VI-6 | $CH_2OH$ | $CH_3$ | 4-Cl | N | T |

The tables can be understood as described below.

6): $(R^{a2})X^{a2}n^{a2}(OH)p^{a1}$ is indicated as a single substituent. Unless $R^a$ is a hydrogen atom, it should be understood that the hydrogen atom-deficient carbon atom on the left end of $(R^{a2})X^{a2}n^{a2}(OH)p^{a1}$ serves to the binding to the cyclopentane ring in Compound (VI). For example, in Compound No. VI-1, $(R^{a2})$=methyl group, $n^{a2}$=0, $p^{a1}$=0.

7): $(R^{b2})X^{b2}n^{b2}(OH)p^{b1}$ is indicated as a single substituent. Unless $R^b$ is a hydrogen atom, it should be understood that the hydrogen atom-deficient carbon atom on the left end of $(R^{b2})X^{b2}n^{b2}(OH)p^{b1}$ serves to the binding to the cyclopentane ring in Compound (VI). For example, in Compound No. VI-1, $(R^{b2})$=methyl group, $n^{b2}$=0, $p^{b1}$=1.

3): "-" indicates a non-substitution (m=0). The number before "-" indicates the binding position when the carbon atom binding to the carbon atom binding to the cyclopentane ring is regarded as being in 1-position in the case of having a substituent on a phenyl ring.

TABLE 18

| Compound No. | Description | $^1$H-NMR (400 MHz, CDCl$_3$)δ |
|---|---|---|
| VI-3 | Colorless viscous oil | 0.84 (3H, s), 1.45-1.62 (4H, m), 1.63-1.71 (1H, m), 1.77 (1H, dt, J = 13.6, 7.9 Hz), 1.97-2.03 (1H, m), 2.12-2.21 (1H, m), 2.42 (1H, dd, J = 13.6, 10.1 Hz), 2.46 (1H, dt, J = 13.6, 5.6 Hz), 3.67-3.86 (2H, m), 4.12 (1H, d, J = 13.9 Hz), 4.0 (1H, s), 4.50 (1H, d, J = 13.9 Hz), 6.92 (2H, d, J = 8.5 Hz), 7.18 (2H, d, J = 8.4 Hz), 7.96 (1H, s), 8.19 (1H, s). |
| VI-4 | Colorless viscous oil | 0.88 (3H, t, J = 7.4 Hz), 1.27-1.36 (1H, m), 1.41-1.52 (2H, m), 1.54-1.66 (2H, m), 1.70-1.82 (1H, m), 1.82-1.93 (1H, m), 2.03-2.17 (2H, m), 2.34-2.41 (1H, m), 3.28 (1H, d, J = 11.1 Hz), 3.72 (1H, d, J = 11.1 Hz), 4.24 (1H, d, J = 14.1 Hz), 4.45 (1H, d, J = 14.1 Hz), 5.03 (1H, brs), 6.97 (2H, d, J = 8.4 Hz), 7.20 (2H, d, J = 8.4 Hz), 7.96 (1H, s), 8.26 (1H, s). |
| VI-5 | White solid | 1.20-1.25 (1H, m), 1.43-1.61 (5H, m), 2.05-2.15 (2H, m), 2.40-2.48 (1H, m), 3.63 (1H, d, J = 11.1 Hz), 3.75 (1H, d, J = 14.0 Hz), 3.77 (1H, d, J = 14.0 Hz), 3.86 (1H, d, J = 11.1 Hz), 4.45 (1H, d, J = 14.3 Hz), 4.75 (1H, d, J = 14.3 Hz), 4.84 (1H, brs), 6.97 (2H, d, J = 8.4 Hz), 7.20 (2H, d, J = 8.4 Hz), 8.00 (1H, s), 8.24 (1H, s). |
| VI-6 | White solid | 1.01 (3H, s) 1.28-1.38 (1H, m), 1.50-1.65 (2H, m), 1.73-1.83 (1H, m), 2.08 (1H, t, J = 5.0 Hz), 2.18 (1H, t, J = 12.7 Hz), 2.37-2.46 (1H, m), 2.76 (1H, dd, J = 12.7, 3.3 Hz), 3.45 (1H, dd, J = 11.2, 5.0 Hz), 3.74 (1H, dd, J = 11.2, 5.1 Hz), 3.97 (1H, s), 4.47 (1H, d, J = 14.3 Hz), 4.58 (1H, d, J = 14.3 Hz), 7.02 (2H, d, J = 8.4 Hz), 7.22 (2H, d, J = 8.4 Hz), 7.97 (1H, s), 8.30 (1H, s). |

$^1$H-NMR Spectra of Compounds VI-1 and VI-2 were well in agreement with the description in JPA5-271197.

Some of the intermediate compounds (V) are produced as described below.

Reference Production Example 8

Synthesis of 2-(2-chloro-2-propenyl)-5-(4-chlorobenzyl)-2-methylcyclopentanone (Compound (V), $(R^a)X^an^a$=$CH_3$, $(R^b)X^bn^b$=$CH_2CCl$=$CH_2$)

(1) Synthesis of Intermediate 3-(2-chloro-2-propenyl)-1-(4-chlorobenzyl)-3-methyl-2-oxocyclopentane carboxylic acid methyl ester (Compound (XIII), $R^1$=$CH_3$, $(R^b)X^bn^b$=$CH_2CCl$=$CH_2$, $R^2$=$CH_3$)

1-(4-chlorobenzyl)-3-methyl-2-oxocyclopentane carboxylic acid methyl ester (Compound (XII), $R^1$=$CH_3$, $R^2$=$CH_3$) (4.0 g, 14.2 mmol) was dissolved in DMF (20 ml), sodium hydride (0.63 g, ca. 60% in mineral oil), 15.8 mmol) was added, and the solution was heated to about 60 degrees C., and then cooled with ice. 2,3-Cichloropropene (1.89 g, 17.0 mmol) was added, the ice bath was removed, stirring was conducted at room temperature for 5 hours, and then stirring was conducted at about 60 degrees C. for 1 hour. To the reaction solution, water (50 ml) was added, extraction with ethyl acetate (80 ml×2) was conducted, and then the organic layer was washed with saturated brine (50 ml), and then dried over anhydrous sodium sulfate, and concentrated. A silica gel column (eluent; hexane:ethyl acetate=10:1) was employed for purification to obtain the desired substance.

Product: 2.94 g

Yield: 58%

Description: Colorless oil $^1$H-NMR (400 MHz, CDCl$_3$) delta:

0.67 (2.52H, s), 1.24 (0.48H, s), 1.62-1.72 (0.84H, m), 1.78-2.00 (1.16H, m), 2.10-2.23 (1H, m), 2.30-2.40 (1H, m), 2.40-2.51 (0.32H, m), 2.51 (0.84H, d, J=14.4 Hz), 2.58 (0.84H, d, J=14.4 Hz), 2.94 (0.16H, d, J=13.8 Hz), 3.14 (0.84H, d, J=13.8 Hz), 3.18 (0.84H, d, J=13.8 Hz), 3.23 (0.16H, d, J=13.8 Hz), 3.71 (2.52H, s), 3.71 (0.48H, s), 5.08-5.10 (0.16H, m), 5.12-5.14 (0.84H, m), 5.23-5.25 (0.84H, m), 5.25-5.27 (0.16H, m), 7.03-7.10 (2H, m), 7.20-7.26 (2H, m).

(2) Synthesis of 2-(2-chloro-2-propenyl)-5-(4-chlorobenzyl)-2-methylcyclopentanone (Compound (V), $(R^a)X^an^a=CH_3$, $(R^b)X^bn^b=CH_2CCl=CH_2$)

3-(2-Chloro-2-propenyl)-1-(4-chlorobenzyl)-3-methyl-2-oxocyclopentane carboxylic acid methyl ester (Compound (XIII), $R^1=CH_3$, $(R^b)X^bn^b=CH_2CCl=CH_2$, $R^2=CH_3$) (2.90 g, 8.16 mmol) was dissolved in i-PrOH (5 ml), and then an aqueous solution of NaOH (0.65 g, 16.3 mmol) dissolved in water (5.4 ml) was added, and stirring under reflux was conducted for 2.5 hours. Water (50 ml) was added, and extraction with hexane (50 ml×2) was conducted. The organic layer was dried over anhydrous sodium sulfate, and concentrated to obtain the desired substance Product: 1.96 g Yield: 81%

Description: Colorless oil $^1$H-NMR (400 MHz, CDCl$_3$) delta:

0.85 (1.98H, s), 1.10 (1.02H, s), 1.42-1.82 (2H, m), 1.90-2.07 (1.66H, m), 2.15-2.25 (0.34H, m), 2.32-2.70 (4H, m), 3.02-3.17 (1H, m), 5.13 (0.34H, s), 5.13-5.16 (0.66H, m), 5.24 (0.66H, s), 5.25-5.28 (0.34H, m), 7.06-7.13 (2H, m), 7.20-7.27 (2H, m).

The intermediate compounds (XVI) are produced also as described below.

[Chem. 30]

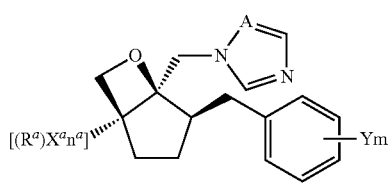

(XVI-C)

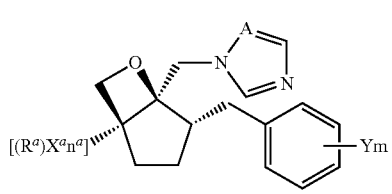

(XVI-T)

TABLE 19

| Compound No. | $(R^a)X^an^{a\,1)}$ | $Ym^{3)}$ | A | Type |
|---|---|---|---|---|
| XVI-1 | CH$_3$ | 4-Cl | N | C |
| XVI-2 | CH$_3$ | 4-Cl | N | T |
| XVI-3 | CH$_3$ | 3-Cl | N | C |
| XVI-4 | CH$_3$ | 4-F | N | C |
| XVI-5 | CH$_3$ | — | N | C |
| XVI-6 | CH$_3$ | 4-Cl | CH | C |
| XVI-7 | CH$_3$CH$_2$ | 4-Cl | N | C |
| XVI-8 | CH$_3$CH$_2$ | — | N | C |
| XVI-9 | CH$_3$ | 2-F | N | C |
| XVI-10 | CH$_3$ | 4-OCF$_3$ | N | C |
| XVI-11 | CH$_3$ | 4-CH$_3$ | N | C |
| XVI-12 | CH$_3$ | 3-Cl | N | T |
| XVI-13 | CH$_3$ | 2,4-F | N | C |
| XVI-14 | CH$_3$ | 4-Ph | N | C |

The tables can be understood as described below.

8): $(R^a)X^an^a$ is indicated as a single substituent. Unless $R^a$ is a hydrogen atom, it should be understood that the hydrogen atom-deficient carbon atom on the left end of $(R^a)X^an^a$ serves to the binding to the cyclopentane ring in Compound (XVI). For example, in Compound No. XVI-1, $(R^a)$=methyl group, $n^a$=0.

3): "-" indicates a non-substitution (m=0). The number before "-" indicates the binding position when the carbon atom binding to the carbon atom binding to the cyclopentane ring is regarded as being in 1-position in the case of having a substituent on a phenyl ring.

Reference Production Example 9

Synthesis of (1RS,4SR,5RS)-4-(4-chlorobenzyl)-1-methyl-5-(1H-1,2,4-triazol-1-ylmethyl)-6-oxabicyclo[3,2,0]heptane (Compound No. XVI-1 (Compound (XVI), $(R^a)X^an^a=CH_3$, Ym=4-Cl, A=N, isomer type: C) and (1RS,4RS,5RS)-4-(4-chlorobenzyl)-1-methyl-5-(1H-1,2,4-triazol-1-ylmethyl)-6-oxabicyclo[3,2,0]heptane (Compound No. (XVI-2) (Compound No. (XVI), $(R^a)X^an^a=CH_3$, Ym=4-Cl, A=N, isomer type: T)

Sodium hydride (3.82 g, 95.5 mmol) washed with hexane, and suspended in THF (50 ml). This was cooled in an ice bath, and the isomer mixture of 5-(4-chlorobenzyl)-2-hydroxymethylmethyl-2-methyl-1-[1,2,4]triazol-1-ylmethylcyclopentanol (Compound No. (VI-a), $R^1=CH_3$, Ym=4-Cl, A=N) (26.1 g, 77.7 mmol) was dissolved in THF (185 ml), and added dropwise over 30 minutes.

After completion of the dropwise addition, stirring was conducted while returning to room temperature for 40 minutes, and then the solution was cooled again in the ice bath and p-toluenesulfonyl chloride (13.2 g, 69.3 mmol) was added and stirring was conducted for 70 minutes. To this, sodium hydride (4.13 g, 103 mmol) was added over 5 minutes and stirring was conducted at room temperature for 1 hour. After completion of the reaction, the content was poured into ice/water, and extracted with ethyl acetate. After washing with saturated brine and drying over anhydrous sodium sulfate, the solvent was distilled away. The resultant residue was recrystallized with ethyl acetate/hexane, and a solid fraction was recovered by filtration. The mother liquor was concentrated, and the resultant residue was subjected to silica gel column chromatography (eluent; hexane:ethyl acetate=1:3 to 0:1) for purification to obtain the desired substance.

Compound No. (XVI-1)

Product: 17.26 g

Yield: 70.0%

Description: White solid, Melting point (m.p.) 95-96 degrees C.

$^1$H-NMR (CDCl$_3$) delta:

1.21 (3H, s), 1.38-1.39 (1H, m), 1.69-1.80 (2H, m), 1.81-1.91 (2H, m), 2.31 (1H, dd, J=13.5, 4.0 Hz), 2.50 (1H, dd, J=13.5, 9.3 Hz), 4.22 (2H, s), 4.43 (1H, d, J=15.0 Hz), 4.48 (1H, d, J=15.0 Hz), 7.04 (1H, d, J=8.4 Hz), 7.22 (1H, d, J=8.4 Hz), 7.95 (1H, s), 8.15 (1H, s).

Compound No. (XVI-2)
Product: 2.57 g
Yield: 10.4%

Description: White solid, Melting point (m.p.) 94.5 degrees C.

$^1$H-NMR (CDCl$_3$) delta:

1.28 (3H, s), 1.56 (1H, dd, J=13.1, 6.5 Hz), 1.73 (1H, tdd, J=13.2, 6.6, 1.6 Hz), 1.85 (1H, dd, J=13.1, 6.8 Hz), 1.97-2.17 (3H, m), 3.04 (1H, d, J=11.1 Hz), 4.16 (1H, d, J=6.0 Hz), 4.35 (1H, dd, J=6.0, 1.6 Hz), 4.56 (1H, d, J=14.6 Hz), 4.74 (1H, d, J=14.6 Hz), 6.94 (2H, d, J=8.3 Hz), 7.22 (2H, d, J=8.3 Hz), 7.97 (1H, s), 8.33 (1H, s).

Similar methods were employed to synthesis Compounds (XVI) listed in Table 19 shown above. Respective MNR spectra are shown below.

TABLE 20

| Compound No. | Description | $^1$H-NMR (400 MHz, CDCl$_3$) δ |
|---|---|---|
| XVI-3 | Colorless viscous oil | 1.20 (3H, s), 1.22-1.35 (1H, m), 1.61-1.82 (2H, m), 1.84-1.89 (2H, m), 2.31 (1H, dd, J = 13.6, 4.0 Hz), 2.51 (1H, dd, J = 13.5, 9.4 Hz), 4.23 (2H, s), 4.43 (1H, d, J = 15.0 Hz), 4.48 (1H, d, J = 15.0 Hz), 6.99 (1H, d, J = 6.7 Hz), 7.13 (1H, s), 7.14-7.21 (2H, m), 7.96 (1H, s), 8.16 (1H, s). |
| XVI-4 | White solid m.p. 88.0-88.7° C. | 1.20 (3H, s), 1.23-1.35 (1H, m), 1.61-1.80 (2H, m), 1.82-1.90 (2H, m), 2.31 (1H, dd, J = 13.5, 4.0 Hz), 2.50 (1H, dd, J = 13.5, 9.2 Hz), 4.21 (1H, d, J = 7.9 Hz), 4.23 (1H, d, J = 7.9 Hz), 4.42 (1H, d, J = 14.9 Hz), 4.47 (1H, d, J = 14.9 Hz), 6.94 (2H, t, J = 8.8 Hz), 7.07 (1H, dd, J = 8.8, 5.5 Hz), 7.95 (1H, s), 8.14 (1H, s). |
| XVI-5 | White solid m.p. 66.6-68.3° C. | 1.20 (3H, s), 1.27-1.37 (1H, m), 1.67-1.79 (2H, m), 1.79-1.95 (2H, m), 2.44 (1H, dd, J = 13.5, 4.7 Hz), 2.56 (1H, dd, J = 13.5, 8.5 Hz), 4.20 (1H, dd, J = 6.0, 1.3 Hz), 4.23 (1H, d, J = 6.0 Hz), 4.37 (1H, d, J = 14.9 Hz), 4.45 (1H, d, J = 14.9 Hz), 7.12 (2H, d, J = 7.3 Hz), 7.18 (1H, t, J = 7.3 Hz), 7.25 (2H, t, J = 7.3 Hz), 7.93 (1H, s), 8.02 (1H, s). |
| XVI-6 | Colorless viscous oil | 1.12 (3H, s), 1.22-1.34 (1H, m), 1.67-1.78 (2H, m), 1.78-1.90 (2H, m), 1.97-2.06 (1H, m), 2.15 (1H, dd, J = 13.7, 3.9 Hz), 2.51 (1H, dd, J = 13.7, 9.7 Hz), 4.15 (1H, d, J = 15.1 Hz), 4.20 (1H, d, J = 6.0 Hz), 4.22 (1H, dd, J = 15.1 Hz), 4.22 (1H, dd, J = 6.0, 1.2 Hz), 7.02 (2H, d, J = 8.4 Hz), 7.09 (2H, d, J = 1.0 Hz), 7.21 (2H, d, J = 8.4 Hz), 7.59 (1H, s). |
| XVI-7 | White solid m.p. 71.4-73.9° C. | 0.77 (3H, t, J = 7.4 Hz), 1.19-1.28 (1H, m), 1.47-1.58 (1H, m), 1.68-1.87 (5H, m), 2.27 (1H, dd, J = 13.4, 3.6 Hz), 2.47 (1H, dd, J = 13.4, 9.3 Hz), 4.20 (1H, d, J = 6.1 Hz), 4.30 (1H, dd, J = 6.1, 1.4 Hz), 4.45 (1H, d, J = 14.9 Hz), 4.49 (1H, d, J = 14.9 Hz), 7.04 (1H, d, J = 8.4 Hz), 7.22 (1H, d, J = 8.4 Hz), 7.95 (1H, s), 8.15 (1H, s). |
| XVI-8 | White solid m.p. 51.4-54.5° C. | 0.77 (3H, t, J = 7.4 Hz), 1.20-1.29 (1H, m), 1.49-1.60 (1H, m), 1.67-1.90 (5H, m), 2.40 (1H, dd, J = 13.4, 4.1 Hz), 2.54 (1H, dd, J = 13.4, 8.4 Hz), 4.20 (1H, d, J = 6.1 Hz), 4.28 (1H, dd, J = 6.1, 1.3 Hz), 4.39 (1H, d, J = 14.9 Hz), 4.47 (1H, d, J = 14.9 Hz), 7.12 (2H, d, J = 6.9 Hz), 7.14-7.20 (1H, m), 7.24-7.29 (2H, m), 7.93 (1H, s), 8.03 (1H, s). |
| XVI-9 | White solid m.p. 54.9-57.4° C. | 1.18 (3H, s), 1.28-1.37 (1H, m), 1.67-1.77 (2H, m), 1.83-1.96 (2H, m), 2.47 (1H, dd, J = 13.6, 3.9 Hz), 2.65 (1H, dd, J = 13.6, 8.7 Hz), 4.19 (1H, dd, J = 6.0, 1.3 Hz), 4.23 (1H, d, J = 6.0 Hz), 4.40 (1H, d, J = 15.0 Hz), 4.49 (1H, d, J = 15.0 Hz), 6.95-7.02 (1H, m), 7.02-7.07 (1H, m), 7.14-7.21 (2H, m), 7.94 (1H, s), 8.14 (1H, s). |
| XVI-10 | Colorless viscous oil | 1.22 (3H, s), 1.24-1.34 (1H, m), 1.69-1.75 (2H, m), 1.79-1.87 (2H, m), 2.32 (1H, dd, J = 13.6, 3.8 Hz), 2.52 (1H, dd, J = 13.5, 9.6 Hz), 4.24 (2H, s), 4.45 (1H, d, J = 14.9 Hz), 4.50 (1H, d, J = 14.9 Hz), 7.09-7.15 (4H, m), 7.95 (1H, s), 8.16 (1H, s). |
| XVI-11 | White solid | 1.19 (3H, s), 1.26-1.34 (1H, m), 1.69-1.90 (4H, m), 2.31 (3H, s), 2.42 (1H, dd, J = 13.5, 4.6 Hz), 2.53 (1H, dd, J = 13.5, 8.5 Hz), 4.18 (1H, dd, J = 6.0, 1.3 Hz), 4.22 (1H, d, J = 6.0 Hz), 4.36 (1H, d, J = 15.0 Hz), 7.01 (2H, d, J = 7.9 Hz), 7.07 (2H, d, J = 7.9 Hz), 7.92 (1H, s), 8.02 (1H, s). |
| XVI-12 | Colorless viscous oil | 1.28 (3H, s), 1.52-1.59 (1H, m), 1.70-1.78 (1H, m), 1.83-1.91 (2H, m), 2.03-2.17 (2H, m), 3.08 (1H, d, J = 9.8 Hz), 4.16 (1H, d, J = 6.1 Hz), 4.35 (1H, dd, J = 6.1, 1.7 Hz), 4.56 (1H, d, J = 14.6 Hz), 4.74 (1H, d, J = 14.6 Hz), 6.89-6.91 (1H, m), 7.03 (1H, brs), 7.15-7.21 (2H, m), 7.98 (1H, s), 8.33 (1H, s). |
| XVI-13 | Colorless viscous oil | 1.19 (3H, s), 1.24-1.33 (1H, m), 1.67-1.74 (2H, m), 1.86-1.88 (2H, m), 2.35 (1H, d, J = 13.3 Hz), 2.60 (1H, dd, J = 13.5, 8.9 Hz), 4.21 (1H, dd, J = 6.0, 1.2 Hz), 4.23 (1H, d, J = 6.0 Hz), 4.45 (1H, d, J = 15.0 Hz), 4.50 (1H, d, J = 15.0 Hz), 6.72-6.80 (2H, m), 7.08-7.14 (1H, m), 7.95 (1H, s), 8.22 (1H, s). |
| XVI-14 | Colorless viscous oil | 1.22 (3H, s), 1.31-1.38 (1H, m), 1.72-1.76 (1H, m), 1.80-1.94 (3H, m), 2.46 (1H, dd, J = 13.6, 4.5 Hz), 2.61 (1H, dd, J = 13.6, |

TABLE 20-continued

| Compound No. | Description | $^1$H-NMR (400 MHz, CDCl$_3$) δ |
|---|---|---|
| | | 8.3 Hz), 4.23 (1H, dd, J = 6.2, 1.0 Hz), 4.26 (1H, d, J = 6.2 Hz), 4.43 (1H, d, J = 14.9 Hz), 4.50 (1H, d, J = 14.9 Hz), 7.21 (2H, d, J = 8.2 Hz), 7.33 (1H, t, J = 7.3 Hz), 7.43 (2H, dd, J = 7.9, 7.3 Hz), 7.51 (2H, d, J = 8.2 Hz), 7.58 (2H, d, J = 8.1 Hz), 7.96 (1H, s), 8.11 (1H, s). |

The intermediate (XXI) for producing Compound No. I-1 can otherwise be synthesized according to the method described in Reference Production Example 10 described below.

Reference Production Example 10

Synthesis of (1RS,4SR,5RS)-4-(4-chlorobenzyl)-1-methyl-5-(1H-1,2,4-triazol-1-ylmethyl)-6-oxobicyclo[3,2,0]heptane (Compound (XXI), Ym=4-Cl, A=N, isomer type: C)

cis-5-(4-Chlorobenzyl)-2,2-bis(hydroxymethyl)-1-(1H-1,2,4-triazol-1-yl)methylcyclopentanol (Compound No. VI-5 (Compound (VI), $(R^{a2})X^{a2}n^{a2}$ (OH)$p^{a1}$=CH$_2$OH, $(R^{b2})X^{b2}n^{b2}$ (OH)$p^{b1}$=CH$_2$OH, Ym=4-Cl, A=N, isomer type: C)) (15 mg, 0.046 mmol) was dissolved in DME (0.8 ml), sodium hydride (4.4 mg, 0.11 mmol) was added, and stirring was conducted at room temperature for 5 minutes. To this solution, p-toluenesulfonyl chloride (9.1 mg, 0.048 mmol) was added, and stirring was conducted at room temperature for 0.4 hour, and then sodium hydride (9.0 mg, 0.23 mmol) and p-toluenesulfonyl chloride (4.0 mg, 0.021 mmol) were further added and stirring was conducted for 0.4 hour to obtain toluene-4-sulfonic acid 4-(4-chlorobenzyl)-5-[1,2,4]triazol-1-ylmethyl-6-oxabicyclo[3,2,0]hepta-1-ylmethyl ester (Compound No. XX-1 (Compound (XX), Ym=4-Cl, A=N) as an intermediate. This was combined with sodium iodide (34 mg, 0.23 mmol) and zinc powder (29 mg, 0.44 mmol) and heated under reflux for 0.6 hour. After completion of the reaction, the solution was cooled to room temperature, the remaining solid was removed by filtration, and the residue was combined with water and extracted with ethyl acetate. The organic layer was washed with water and saturated brine, and dried over anhydrous sodium sulfate. The solvent was distilled away, and the resultant residue was purified by silica gel chromatography (eluent; hexane:ethyl acetate=1:1 to 1:5) to obtain the desired substance.

Product: 3.2 mg (0.010 mmol)
Yield: 22%

This Compound (XXI) has a meaning identical to the abovementioned Compound (XVI)-1 and the NMR spectra were in complete agreement.

The intermediate (XIX) employed here can be synthesized in accordance with Reference Production Example 11 described below.

Reference Production Example 11

(1) Synthesis of 1-(4-chlorobenzyl)-3,3-bis-hydroxymethyl-2-oxo-cyclopentancarboxylic acid methyl ester (Compound (XXVI), R$^2$=CH$_3$, Ym=4-Cl)

1-(4-Chlorobenzyl)-2-oxo-cyclopentancarboxylic acid methyl ester (Compound No. (XXV)-1, (Compound (XXV), R$^2$=CH$_3$, Ym=4-Cl, A=N) (266.7 mg, 1.00 mmol) was combined with potassium carbonate (69 mg, 0.50 mmol), 37% aqueous solution of formaldehyde (0.242 ml, 3.00 mmol) and THF (0.72 ml) and vigorous stirring was conducted at room temperature for 5 hours. After completion of the reaction, water was added and extraction with ethyl acetate was conducted. The organic layer was washed with saturated brine, and then dried over anhydrous sodium sulfate and the solvent was distilled away. The residue was subjected to silica gel column chromatography (eluent; ethyl acetate:hexane=2:1) for purification to obtain the desired substance.

Product: 305.8 mg
Yield: 93.6%
Description: Colorless viscous liquid
$^1$H-NMR (400 MHz, CDCl$_3$) delta:
1.72-1.80 (1H, m), 1.91-2.01 (3H, m), 2.15-2.19 (1H, m), 2.40-2.45 (1H, m), 3.10 (1H, d, J=13.8 Hz), 3.17 (1H, d, J=13.8 Hz), 3.36 (1H, dd, J=11.0, 7.3 Hz), 3.43 (1H, dd, J=11.0, 4.2 Hz), 3.69-3.75 (2H, m), 3.73 (3H, s), 7.05 (2H, d, J=8.4 Hz), 7.24 (2H, d, J=8.4 Hz).

(2) Synthesis of 1-(4-chlorobenzyl)-3,3-bis-methoxymethoxymethyl-2-oxo-cyclopentancarboxylic acid methyl ester (Compound (XXVII), G$^2$=CH$_2$OCH$_3$, R$^2$=CH$_3$, Ym=4-Cl)

1-(4-Chlorobenzyl)-3,3-bis-hydroxymethyl-2-oxo-cyclopentancarboxylic acid methyl ester (Compound (XXVI), R$^2$=CH$_3$, Ym=4-Cl) (3.6871 g, 10.0 mmol) was dissolved in chloroform (14.5 ml), combined with dimethoxymethane (14.5 ml), lithium bromide (173.6 mg, 2.00 mmol) and p-toluenesulfonic acid monohydrate (190.2 mg, 1.00 mmol) and stirring was conducted at room temperature for 2 hours. After completion of the reaction, an aqueous solution of sodium hydrogen carbonate and diethyl ether were added, and the organic layer was separated. This was washed with saturated brine, and dried over anhydrous sodium sulfate. The solvent was distilled away, and the residue was subjected to silica gel column chromatography (eluent; hexane:ethyl acetate=2:1 to 1:1) for purification to obtain the desired substance.

Product: 2.3455 g
Yield: 56.5%
Description: Colorless viscous liquid
$^1$H-NMR (400 MHz, CDCl$_3$) delta:
1.85-1.93 (1H, m), 2.00-2.08 (1H, m), 2.14-2.22 (1H, m), 2.43-2.51 (1H, m), 2.88 (1H, d, J=13.8 Hz), 3.28 (3H, s), 3.29 (3H, m), 3.28-3.32 (1H, m), 3.38 (1H, dd, J=9.1, 6.1 Hz), 3.53 (1H, dd, J=9.1, 6.1 Hz), 4.46 (1H, d, J=6.5 Hz), 4.49 (2H, s), 4.49 (1H, d, J=6.5 Hz), 7.06 (2H, d, J=8.4 Hz), 7.22 (2H, d, J=8.4 Hz).

(3) Synthesis of 5-chlorobenzyl-2,2-bis-methoxymethoxymethyl-cyclopentanone (Compound (XXII), G$^2$=CH$_2$OCH$_3$, Ym=4-Cl)

1-(4-Chlorobenzyl)-3,3-bis-methoxymethoxymethyl-2-oxo-cyclopentancarboxylic acid methyl ester (Compound (XXVII), $G^2$=CH$_2$OCH$_3$, $R^2$=CH$_3$, Ym=4-Cl) (2.2895 g, 5.52 mmol) was dissolved in isopropanol (5.5 ml), a 2 mol/l aqueous solution of sodium hydroxide (5.5 ml) was added and stirring was conducted for 2 hours at 90 degrees C. After completion of the reaction, water was added and extraction with ethyl acetate was conducted. The organic layer was washed with water and saturated brine, and dried over anhydrous sodium sulfate. The solvent was distilled away, and the residue was subjected to silica gel column chromatography (eluent; hexane:ethyl acetate=3:1) for purification to obtain the desired substance.

Product: 1.3029 g
Yield: 66.1%
Description: Colorless viscous liquid
$^1$H-NMR (400 MHz, CDCl$_3$) delta:
1.57-1.67 (1H, m), 1.96-2.11 (3H, m), 2.40-2.49 (1H, m), 2.52 (1H, dd, J=13.5, 9.3 Hz), 3.11 (1H, dd, J=13.5, 4.2 Hz), 3.30 (6H, s), 3.35 (1H, d, J=9.1 Hz), 3.42 (1H, d, J=9.2 Hz), 3.50 (1H, d, J=9.1 Hz), 3.59 (1H, d, J=9.1 Hz), 4.49 (1H, d, J=6.5 Hz), 4.51 (1H, d, J=6.5 Hz), 4.53 (1H, d, J=6.5 Hz), 4.55 (1H, d, J=6.5 Hz), 7.10 (2H, d, J=8.4 Hz), 7.23 (2H, d, J=8.4 Hz).

(4) Synthesis of 5-(4-chlorobenzyl)-2,2-bis-methoxymethoxymethyl-1-[1,2,4]triazol-1-ylmethylcyclopentanol (Compound (XXIV), $G^2$=CH$_2$OCH$_3$, Ym=4-Cl, A=N)

[1,2,4]-Triazole sodium salt (526 mg, 5.78 mmol) was dissolved in NMP (3 ml), and heated to an internal temperature of 115 degrees C. To this, 1 ml of a solution of 5-chlorobenzyl-2,2-bis-methoxymethoxymethyl-cyclopentanone (Compound No. (Compound (XXII), $G^2$=CH$_2$OCH$_3$, Ym=4-Cl) 1.374 g (3.85 mmol) in NMP was added. To this solution, sodium t-butoxide 333 mg (3.47 mmol) and TMSOB 1.193 g (6.87 mmol) were added in portions while conducting the reaction at 115 degrees C. for 5 hours. After completion of the reaction, the reaction solution was cooled to 35 degrees C., combined with 15 ml of water, and extracted with ethyl acetate. The organic layer was washed with water and saturated brine, dried over anhydrous sodium sulfate. The solvent was distilled away and the residue was subjected to silica gel column chromatography (eluent; ethyl acetate) for purification to obtain the desired substance.

Product: 680.2 mg
Yield: 40.2%
Description: Colorless viscous liquid
$^1$H-NMR (CDCl$_3$) delta:
1.47-1.56 (1H, m), 1.60-1.80 (2H, m), 1.73-1.83 (1H, m), 2.17 (1H, dd, J=13.2, 4.0 Hz), 2.22-2.31 (1H, m), 2.44 (1H, dd, J=13.2, 10.3 Hz), 3.31 (3H, s), 3.33 (1H, d, J=9.7 Hz), 3.38 (3H, s), 3.46 (1H, d, J=9.7 Hz), 3.59 (2H, s), 4.32 (1H, d, J=14.2 Hz), 4.41 (1H, s), 4.45 (1H, d, J=6.4 Hz), 4.48 (1H, d, J=6.4 Hz), 4.54 (1H, d, J=14.2 Hz), 4.64 (2H, s), 7.04 (2H, d, J=8.4 Hz), 7.21 (2H, d, J=8.4 Hz), 7.95 (1H, s), 8.24 (1H, s).

(5) Synthesis of cis-5-(4-chlorobenzyl)-2,2-bis-hydroxymethyl-1-[1,2,4]triazol-1-ylmethylcyclopentanol (Compound (XIX), Ym=4-Cl, A=N)

5-(4-Chlorobenzyl)-2,2-bis-methoxymethoxymethyl-1-[1,2,4]triazol-1-ylmethylcyclopentanol (Compound No. (XXIV)-1 (Compound (XXIV), $G^2$=CH$_2$OCH$_3$, Ym=4-Cl, A=N) (403 mg, 0.916 mmol) was dissolved in a 10% methanol solution of hydrogen chloride (8 ml), and stirring was conducted at room temperature for 23 hours. After completion of the reaction, the solvent was distilled away, and the residue was combined with water. To this suspension, 2 mol/l aqueous solution of sodium hydroxide was added for neutralization, and stirring was conducted at room temperature for 15 minutes. The crystal was recovered by filtration and dried in vacuum to obtain the desired substance.

Product: 271.1 mg
Yield: 84.1%
Description: White solid
$^1$H-NMR (400 MHz, CDCl$_3$) delta:
1.20-1.25 (1H, m), 1.43-1.61 (5H, m), 2.05-2.15 (2H, m), 2.40-2.48 (1H, m), 3.63 (1H, d, J=11.2 Hz), 3.75 (1H, d, J=14.0 Hz), 3.77 (1H, d, J=14.0 Hz), 3.86 (1H, d, J=11.2 Hz), 4.45 (1H, d, J=14.3 Hz), 4.75 (1H, d, J=14.3 Hz), 4.84 (1H, brs), 6.97 (2H, d, J=8.4 Hz), 7.20 (2H, d, J=8.4 Hz), 8.00 (1H, s), 8.24 (1H, s).

The followings are Formulation Examples and Experimental Examples. Carriers (diluents) and auxiliary agents, as well as the mixing ratio thereof for active ingredients may vary within a wide range. "Parts" in each Formulation Example mean "parts by weight".

Formulation Example 1

Wettable Formulation

Compound (I-1) 50 parts
Lignin sulfonate 5 parts
Alkyl sulfonate 3 parts
Diatomaceous earth 42 parts
are ground and mixed to form a wettable formulation, which is used as being diluted in water.

Formulation Example 2

Powder Formulation

Compound (I-1) 3 parts
Clay 40 parts
Talc 57 parts
are ground and mixed, and used as a dusting formulation.

Formulation Example 3

Granule Formulation

Compound (I-1) 5 parts
Bentonite 43 parts
Clay 45 parts
Lignin sulfonate 7 parts
are mixed uniformly, combined with water and further kneaded, and subjected to an extruding granulator to obtain a granule, which is dried and used as a granule formulation.

Formulation Example 4

Emulsion Formulation

Compound (I-1) 20 parts
Polyoxyethylene alkylaryl ether 10 parts
Polyoxyethylene sorbitan monolaurate 3 parts
Xylene 67 parts
are mixed and dissolved uniformly to obtain an emulsion.

Experimental Example 1

Efficacy Test Against Cucumber Gray Mold

Onto a cucumber (variety:SHARP1) plant in its cotyledon phase grown using a square plastic pot (6 cm×6 cm), a wettable formulation such as Formulation Example 1 which was diluted and suspended in water at a certain concentrations (100 mg/L and 50 mg/L) was sprayed at a rate of 1,000 L/ha. The sprayed leaves were air-dried, and loaded with a paper disc (8 mm in diameter) soaked in a spore suspension of *Botrytis cinerea*, and kept at 20 degrees C. and a high humidity. Four days after inoculation, the cucumber gray mold lesion degree was investigated, and the protective value was calculated by the following equation.

Protective value(%)=(1−mean lesion degree in sprayed plot/mean lesion degree in unsprayed plot)×100

TABLE 21

| Lesion degree | % Area of onset |
| --- | --- |
| 0 | No Onset |
| 0.5 | % Area of lesion spot < 5% |
| 1 | 5% ≤ % Area of lesion spot < 10% |
| 2 | 10% ≤ % Area of lesion spot < 25% |
| 3 | 25% ≤ % Area of lesion spot < 50% |
| 4 | 50% ≤ % Area of lesion spot < 80% |
| 5 | 80% ≤ % Area of lesion spot |

In the test described above, Compounds I-1, I-15, I-25, I-65, I-73, I-74, I-77, I-80, I-86, I-88, I-97, I-101, I-104, I-203, I-601, I-602 for example, showed protective values of 80% or higher at 100 mg/L. Furthermore, compounds I-1, I-15, I-73, I-74, I-77, I-80, I-86, I-88, I-97, I-101, I-104, I-203, I-601, I-602 for example, showed protective values of 80% or higher at 50 mg/L.

Experimental Example 2

Efficacy Test Against Wheat Brown Rust

Onto a wheat plant (variety: NORIN No. 61) grown to the two-leaf phase using a square plastic pot (6 cm×6 cm), a wettable formulation such as Formulation Example 1 which was diluted and suspended in water at a certain concentration (100 mg/L and 10 mg/L) was sprayed at a rate of 1,000 L/ha. The sprayed leaves were air-dried, and inoculated with spore suspension of *Puccinia recondita* (adjusted at 200 spores/vision, Gramin S was added at 60 ppm) by spraying, and kept at 25 degrees C. and a high humidity for 48 hours. Thereafter, the plant was kept in a greenhouse. Nine to 14 days after inoculation, the wheat brown rust lesion degree was investigated, and the protective value was calculated by the following equation.

Protective value(%)=(1−lesion degree in sprayed plot/lesion degree in unsprayed plot)×100

TABLE 22

Leaf rust damage scale by Peterson

| Lesion degree | % Area of onset |
| --- | --- |
| 0 | No onset |
| 0.5 | Less than 1% |
| 1 | 1% or higher and less than 5% |
| 2 | 5% or higher and less than 10% |
| 3 | 10% or higher and less than 30% |
| 4 | 30% or higher and less than 50% |
| 5 | 50% or higher |

In the test described above, Compounds I-1, I-15, I-25, I-36, I-65, I-73, I-74, I-77, I-79, I-80, I-82, I-86, I-88, I-97, I-101, I-104, I-115, I-203, I-244, I-301, I-601, I-602 for example, showed protective values of 90% or higher at 100 mg/L. Furthermore, compounds I-1, I-15, I-25, I-36, I-73, I-74, I-77, I-79, I-80, I-86, I-88, I-97, I-101, I-104, I-203, I-601, I-602 for example, showed higher efficacy than that of compound (1) described in [0404] at 10 mg/L.

Experimental Example 3

Efficacy Test Against Wheat *Fusarium* Head Blight

Onto a head of a wheat plant (variety: NORIN No. 61) grown to the blooming phase, a wettable formulations such as Formulation Example 1 which was diluted and suspended in water at certain concentrations (500 mg/L and 100 mg/L) was sprayed at a rate of 1,000 L/ha. The head was air-dried, and inoculated with spore suspension of *Fusarium graminearum* (adjusted at $2 \times 10^5$ spores/ml, containing Gramin S at a final concentration of 60 ppm and sucrose at a final concentration of 0.5%) by spraying, and kept at 20 degrees C. and a high humidity. Four to 7 days after inoculation, the wheat *fusarium* head blight lesion degree was investigated, and the protective value was calculated by the following equation.

Protective value(%)=(1−lesion degree in sprayed plot/lesion degree in unsprayed plot)×100

TABLE 23

| Lesion degree | % Area of onset |
| --- | --- |
| 0 | No onset |
| 0.2 | Less than 1% |
| 0.5 | 1% or higher and less than 3% |
| 1 | 3% or higher and less than 5% |
| 2 | 5% or higher and less than 10% |
| 3 | 10% or higher and less than 25% |
| 4 | 25% or higher and less than 50% |
| 5 | 50% or higher |

In the assay described above, Compounds I-1, I-15, I-25, I-36, I-65, I-73, I-74, I-77, I-79, I-80, I-82, I-86, I-88, I-97, I-101, I-104, I-115, I-174, I-203, I-244, I-301, I-365, I-374, I-401, I-601, I-602 for example, showed protective values of 90% or higher at 500 mg/L. Furthermore, compounds I-1, I-25, I-36, I-73, I-74, I-77, I-80, I-86, I-88, I-101, I-104, I-115, I-601, I-602 for example, showed protective values of 80% or higher at 100 mg/L.

Experimental Example 4

Microplate Test of Biocidal Effect on Wheat *Septoria* Blotch (*Septoria tritici*)

A spore suspension of wheat *Septoria* blotch (*Septoria tritici*) (spore concentration: $1 \times 10^6$ cells/ml) was prepared, and subjected to 100-fold dilution with a PD medium. A flat 96-well microplate was provided and 1 microliter of the test compound solution formed by dissolution in dimethyl sulfoxide (DMSO) at a concentration 100 times the test concentration was dispensed to the microplate, and then 100 microliter of the medium containing the spore was added and stirred thoroughly. A non-inoculated control zone was provided by adding 1 microliter of DMSO, and after cultivating at 20 degrees C. for about 10 days, the absorbance (550 nm) was measured and % mycelium growth inhibitions were calculated according to the following equation to obtain the activity level ($EC_{80}$).

$R = 100 \times (dc - dt)/dc;$

R: % mycelium growth inhibition
dc: Absorbance of non-treatment zone
dt: Absorbance of treatment zone With regard to the activity level ($EC_{80}$), I-1, I-15, I-25, I-36, I-73, I-74, I-77, I-79, I-80, I-86, I-88, I-97, I-101, I-104, I-203, I-244, I-301, I-601, I-602 for example, showed an activity level as high as 0.2 mg/L or less, in contrast to the following comparative compound (I) described in Patent Literature 1 (JPA01-93574) whose activity was 0.4 mg/L.

Comparative Compound (1):

(1RS,5SR)-5-(4-chlorobenzyl)-2,2-dimethyl-1-(1H-1,2,4-triazol-1-ylmethyl)cyclopentanol

[Chem. 31]

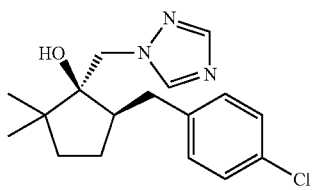

(1)

Experimental Example 5

Assay for Fungicidal Effect on Various Pathogenic Microorganism and Hazardous Microorganisms In this Experimental Example, the fungicidal effects of the inventive compounds on various phytopathogenic fungi for plants and hazardous microorganism for industrial materials were examined by the methods described below.

Each inventive compound was dissolved in 2 ml of dimethyl sulfoxide. 0.6 ml of this solution was added to 60 ml of a PDA medium (potato dextrose agar medium) at about 60 degrees C., which was mixed thoroughly in a 100-ml conical flask, and poured into a dish, where it was solidified, thereby obtaining a plate medium containing the inventive compound at 50 mg/L and 5 mg/L.

On the other hand, a subject microorganism previously cultured on a plate medium was cut out using a cork borer whose diameter was 4 mm, and inoculated to the test compound-containing plate medium described above. After inoculation, the dish was grown at the optimum growth temperatures for respective microorganisms (for this growth temperature, see, for example, a reference LIST OF CULTURES 1996 microorganisms 10th edition, Institute for Fermentation (foundation)) for 1 to 3 days, and the mycelial growth was measured as a diameter of its flora. The growth degree of the microorganism on the test compound-containing plate medium thus observed was compared with the growth degree of the microorganism in the untreated group, and % mycelial growth inhibition was calculated by the following equation.

$$R = 100(dc-dt)/dc$$

wherein R=% mycelial extension inhibition, dc=flora diameter in untreated plate, dt=flora diameter in treated plate.

The results obtained as described above were evaluated as one of the 5 grades according to the following criteria.

<Growth Inhibition Grade>
5: % Mycerial growth inhibition of 80% or higher
4: % Mycerial growth inhibition of less than 80 to 60% or higher
3: % Mycerial growth inhibition of less than 60 to 40% or higher
2: % Mycerial growth inhibition of less than 40 to 20% or higher
1: % Mycerial growth inhibition of less than 20%

TABLE 24-1

| Compound No. | Concentration (mg/L) | P.n | P.h | F.g | U.n | P.o | G.f | A.m | S.s | B.c | F.c | R.sec |
|---|---|---|---|---|---|---|---|---|---|---|---|---|
| I-1 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |
| I-15 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |
| I-25 | 50 | 5 | 5 | 5 | 5 | 5 | 5 | 5 | 5 | 5 | 5 | 5 |
|  | 5 | 4 | 3 | 5 | 3 | 5 | 5 | 4 | 5 | 5 | 5 | 5 |
| I-36 | 50 | 5 | 5 | 5 | 5 | 5 | 5 | 5 | 5 | 5 | 5 | 5 |
|  | 5 | 5 | 5 | 5 | 4 | 5 | 5 | 5 | 5 | 4 | 5 | 5 |
| I-65 | 50 | 5 | 5 | 5 | 5 | 5 | 5 | 5 | 5 | 5 | 5 | 5 |
|  | 5 | 4 | 3 | 4 | 3 | 3 | 4 | 3 | 3 | 4 | 3 | 3 |
| I-73 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |
| I-74 | 50 | 5 | 5 | 5 | 5 | 5 | 5 | 5 | 5 | 5 | 5 | 5 |
|  | 5 | 5 | 5 | 5 | 5 | 5 | 5 | 4 | 5 | 5 | 5 | 5 |
| I-77 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |
| I-79 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |
| I-80 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |
| I-82 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |
| I-86 | 50 | 5 | 5 | 5 | 5 | 5 | 5 | 5 | 5 | 5 | 5 | 5 |
|  | 5 | 5 | 5 | 5 | 5 | 5 | 5 | 4 | 5 | 5 | 5 | 5 |
| I-88 | 50 | 5 | 5 | 5 | 5 | 5 | 5 | 5 | 5 | 5 | 5 | 5 |
|  | 5 | 5 | 5 | 5 | 5 | 5 | 5 | 4 | 5 | 5 | 5 | 5 |
| I-97 | 50 | 5 | 5 | 5 | 5 | 5 | 5 | 5 | 5 | 5 | 5 | 5 |
|  | 5 | 5 | 5 | 5 | 5 | 5 | 5 | 4 | 5 | 5 | 5 | 5 |
| I-101 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |

TABLE 24-2

| Compound No. | Concentration (mg/L) | P.n | P.h | F.g | U.n | P.o | G.f | A.m | S.s | B.c | F.c | R.sec |
|---|---|---|---|---|---|---|---|---|---|---|---|---|
| I-104 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |
| I-115 | 50 | 5 | 5 | 5 | 5 | 5 | 5 | 5 | 5 | 5 | 5 | 5 |
|  | 5 | 4 | 5 | 5 | 4 | 5 | 5 | 5 | 5 | 5 | 5 | 5 |
| I-174 | 50 | 5 | 5 | 5 | 5 | 5 | 5 | 5 | 5 | 5 | 5 | 5 |
|  | 5 | 5 | 5 | 5 | 4 | 5 | 5 | 5 | 5 | 5 | 5 | 5 |
| I-203 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |
| I-244 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 4 | 5 | 5 |
| I-301 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |
| I-365 | 50 | 5 | 5 | 5 | 5 | 5 | 5 | 5 | 5 | 5 | 5 | 5 |
|  | 5 | 3 | 2 | 2 | 2 | 1 | 1 | 2 | 2 | 1 | 2 | 2 |
| I-374 | 50 | 5 | 5 | 5 | 5 | 5 | 5 | 5 | 5 | 5 | 5 | 5 |
|  | 5 | 5 | 5 | 5 | 4 | 5 | 5 | 4 | 5 | 5 | 5 | 5 |
| I-401 | 50 | 5 | 5 | 5 | 5 | 5 | 5 | 5 | 5 | 5 | 5 | 5 |
|  | 5 | 5 | 5 | 5 | 4 | 5 | 5 | 4 | 5 | 5 | 5 | 5 |
| I-601 | 50 | 5 | 5 | 5 | 5 | 5 | 5 | 5 | 5 | 5 | 5 | 5 |
|  | 5 | 4 | 4 | 5 | 3 | 5 | 5 | 4 | 5 | 4 | 5 | 5 |
| I-602 | 50 | 5 | 5 | 5 | 5 | 5 | 5 | 5 | 5 | 5 | 5 | 5 |
|  | 5 | 3 | 3 | 5 | 4 | 5 | 5 | 4 | 5 | 4 | 5 | 5 |

TABLE 24-3

| Compound No. | Concentration (mg/L) | P.n | P.h | F.g | U.n | P.o | G.f | A.m | S.s | B.c | F.c | R.sec |
|---|---|---|---|---|---|---|---|---|---|---|---|---|
| I-1 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |
| I-73 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |
| I-77 | 50 | 5 | 5 | 5 | 5 | 5 | 5 | 5 | 5 | 5 | 5 | 5 |
|  | 5 | 5 | 5 | 5 | 5 | 5 | 5 | 5 | 5 | 5 | 5 | 5 |
| compound (2) | 50 | 4 | 4 | 5 | 3 | 4 | 4 | 4 | 5 | 5 | 4 | 5 |
|  | 5 | 3 | 2 | 3 | 1 | 4 | 3 | 4 | 3 | 2 | 3 | 5 |

Wheat *Septoria nodorum* blotch (*Phaeosphaeria nodorum*) P.n
Wheat eye spot (*Pseudocercoporella herpotrichoides*) P.h
Wheat *fusarium* blight (*Fusarium graminearum*) F.g
Barley loose smut (*Ustilago nuda*) U.n
Rice blast (*Pyricularia oryzae*) P.o
Rice bakanae disease (*Giberella fujikuroi*) G.f
*Alternaria* blotch (*Alternaria alternata*) A.m
*Sclerotinia* rot (*Sclerotinia sclerotiorum*) S.s
Gray mold (*Botritis cinerea*) B.c
Cucumber *fusarium* wilt (*Fusarium oxysporum*) F.c
Barley leaf blotch (*Rhynchosporium secalis*) R.sec
Comparative Compound (2):

[Chem. 32]

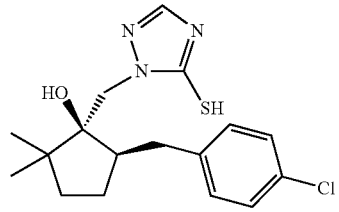

Also in the experiments with the treatment at 50 mg/l against a microorganism which deteriorates paper, pulp, fiber, leather, paint and the like, namely, *Aspergillus* microorganism (*Aspergillus* sp.), *Tricoderma* microorganism (*Trichoderma* sp.), *penicillium* microorganism (*Penicillium* sp.), *Cladosporium* microorganism (*Cladosporium* sp.), *Mucor* microorganism (*Mucor* sp.), *Aureobasidium* microorganism (*Aureobasidium* sp.), *Curvularia* microorganism (*Curvularia* sp.), a wood denaturing microorganism Oouzuratake (*Tyromyces palustris*) and Kawaratake, (*Coriolus versicolor*), Compounds I-1, I-15, I-25, I-36, I-65, I-73, I-74, I-77, I-80, I-82, I-86, I-88, I-97, I-101, I-104, I-115, I-174, I-203, I-244, I-301, I-365, I-401, I-601, I-602 showed growth inhibition grades as high as 4.

Experimental Example 6

Rice Elongation Prevention Assay 36 mg of a test compound was dissolved in 3.6 ml of DMSO, and applied to 180 g of rice seeds in a vial. After soaking the seeds and promoting germination, the seeds were seeded to seedling boxes at a rate of 180 g/box, allowed to germinate in the seedling boxes, and then cultivated in a greenhouse at 35 degrees C. 20 Days after seeding, the plant height of the seedlings in each treatment group was surveyed in 10 locations, and the % plant height suppression was calculated by the following Equation 6.

$R = 100(hc-ht)/hc$ wherein R=% Plant
height suppression, hc=Mean untreated plant height, ht=mean treated plant height.

The results obtained above were assigned to one of the following 5 grades of the growth regulation.
<Growth Regulation Grade>
5: % Plant height suppression of 50% or higher
4: % Plant height suppression of less than 50 to 30% or higher
3: % Plant height suppression of less than 30 to 20% or higher
2: % Plant height suppression of less than 20 to 10% or higher
1: % Plant height suppression of 10% or less In the assay described above, Compounds I-1, I-15, I-25, I-36, I-65, I-73, I-74, I-77, I-80, I-82, I-86, I-88, I-97, I-101, I-104, I-115, I-203, I-244, I-301, I-365, I-374, I-401, I-601, I-602 showed growth regulation grades of 4 or higher in the growth of rice plant.

Experimental Example 7

Assay for Fungicidal Effect on Septoria tritici

In this Experimental Example, the fungicidal effects of the inventive compounds on a phytopathogenic fungi, Septoria tritici were examined and compared to the Comparative Compound (3) described in Patent Literature 1 (JPA01-93574) by the methods described below.

Comparative Compound (3):

(1RS,5SR)-5-(4-fluorobenzyl)-2,2-dimethyl-1-(1H-1,2,4-triazol-1-ylmethyl)cyclopentanol Each inventive compound was dissolved in 2 ml of dimethyl sulfoxide to obtain a prescribed concentration. 0.6 ml of the each solution was added to 60 ml of a PDA medium (potato dextrose agar medium) at about 60 degrees C., which was mixed thoroughly in a 100-ml conical flask, and poured into a dish, where it was solidified, thereby obtaining medium plates containing the inventive compound at 0.02 mg/L.

The subject microorganism previously cultured on a plate medium was cut out using a cork borer whose diameter was 4 mm, and inoculated to the test compound-containing plate medium described above. After inoculation, the dish was incubated at the optimum growth temperatures for the microorganism (for this growth temperature, see, for example, a reference LIST OF CULTURES 1996 microorganisms 10th edition, Institute for Fermentation (foundation)) for 10 days, and the mycelial growth was measured as a diameter of its flora. The growth degree of the microorganism on the test compound-containing plate medium thus observed was compared with the growth degree of the microorganism in the untreated group, and % mycelial growth inhibition was calculated by the following equation.

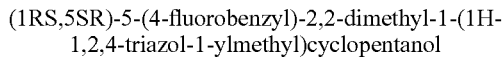

$$R=100(dc-dt)/dc$$

wherein R=% mycelial extension inhibition, dc=flora diameter in untreated plate, dt=flora diameter in treated plate.

The results obtained as described above were evaluated as one of the 5 grades according to the following criteria.
<Growth Inhibition Grade>
5: % Mycerial growth inhibition of 80% or higher
4: % Mycerial growth inhibition of less than 80 to 60% or higher
3: % Mycerial growth inhibition of less than 60 to 40% or higher
2: % Mycerial growth inhibition of less than 40 to 20% or higher
1: % Mycerial growth inhibition of less than 20%

In the test described above, following results were obtained.

TABLE 25

| Compound No. | Concentration mg/L | grade |
|---|---|---|
| I-73 | 0.02 | 5 |
| I-77 | 0.02 | 5 |
| Compound (3) | 0.02 | 2 |

Experimental Example 8

Efficacy Test Against Wheat Brown Rust

Onto a wheat plant (variety: NORIN No. 61) grown to the two-leaf phase using a square plastic pot (6 cm×6 cm), a wettable formulation such as Formulation Example 1 which was diluted and suspended in water at a certain concentration (2 mg/L) was sprayed at a rate of 1,000 L/ha. The sprayed leaves were air-dried, and inoculated with spore suspension of Puccinia recondita (adjusted at 200 spores/vision, Gramin S was added at 60 ppm) by spraying, and kept at 25 degrees C. and a high humidity for 48 hours. Thereafter, the plant was kept in a greenhouse. Nine to 14 days after inoculation, the wheat brown rust lesion degree was investigated, and the protective value was calculated by the following equation.

Protective value(%)=(1−lesion degree in sprayed plot/lesion degree in unsprayed plot)×100

TABLE 26

| Leaf rust damage scale by Peterson | |
|---|---|
| Lesion degree | % Area of onset |
| 0 | No onset |
| 0.5 | Less than 1% |
| 1 | 1% or higher and less than 5% |
| 2 | 5% or higher and less than 10% |
| 3 | 10% or higher and less than 30% |
| 4 | 30% or higher and less than 50% |
| 5 | 50% or higher |

In the test described above, following results were obtained.

TABLE 27

| Compound No. | Concentration mg/L | degree |
|---|---|---|
| I-77 | 0.02 | 0 |
| Compound (3) | 0.02 | 3 |

Experimental Example 9

Assay for Fungicidal Effect on Septoria tritici

In this Experimental Example, the fungicidal effects of the inventive compounds on Septoria tritici were examined by the methods described in the Experimental Example 5. In this Experimental Example, the inventive compounds were diluted at 1.25 mg/L.

TABLE 28

| Compound No. | Concentration (mg/L) | growth inhibition grade |
|---|---|---|
| I-1 | 1.25 | 5 |
| I-73 | 1.25 | 5 |
| I-77 | 1.25 | 5 |
| I-88 | 1.25 | 5 |
| compound (1) | 1.25 | 3 |
| compound (2) | 1.25 | 1 |

Experimental Example 10

Efficacy Test Against Wheat Brown Rust

In this Experimental Example, the wheat brown rust lesion degree was investigated by the methods described in the Experimental Example 2. In this Experimental Example, the inventive compounds were diluted at 1 mg/L and sprayed at a rate of 1,000 L/ha.

TABLE 29

| Compound No. | Concentration (g/ha) | lesion degree |
|---|---|---|
| I-1 | 1 | 0.5 |
| I-73 | 1 | 0.5 |
| I-77 | 1 | 0.5 |
| I-88 | 1 | 0.5 |
| compound (1) | 1 | 3 |
| compound (2) | 1 | 5 |

INDUSTRIAL APPLICABILITY

An azole derivative according to the invention can preferably be utilized as an active ingredient of agro-horticultural bactericides, plant growth regulators and industrial material protecting agents.

The invention claimed is:

1. An azole derivative represented by Formula (I):

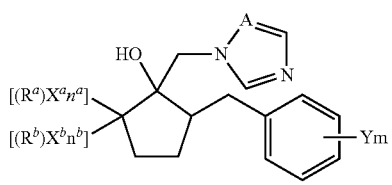

(I)

wherein each of $R^a$ and $R^b$ independently denotes a hydrogen atom, or a $C_1$-$C_6$ alkyl group, a $C_2$-$C_6$ alkenyl group or a $C_2$-$C_6$ alkynyl group; provided that $R^a$ and $R^b$ are not hydrogen atoms at the same time, and the hydrogen atoms of the alkyl group, the alkenyl group and the alkynyl group may be substituted with $X^a$ or $X^b$; each of $X^a$ and $X^b$ denotes a halogen atom;

$n^a$ denotes 0 or the number of $X^a$-substituted hydrogen atoms among the hydrogen atoms in $R^a$;

$n^b$ denotes 0 or the number of $X^b$-substituted hydrogen atoms among the hydrogen atoms in $R^b$;

provided that "$n^a+n^b$" is 1 or more; when $n^a$ is 2 or more, then each $X^a$ may be same or different; when $n^b$ is 2 or more, then each $X^b$ may be same or different;

each Y denotes a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a phenyl group, a cyano group or a nitro group;

m denotes 0 to 5; when m is 2 or more, each Y may be same or different;

A denotes a nitrogen atom or a methyne group.

2. The azole derivative according to claim 1 wherein each of the alkyl group, the alkenyl group and the alkynyl group in $R^a$ and $R^b$ in Formula (I) described above denotes a $C_1$-$C_4$ alkyl group, a $C_2$-$C_4$ alkenyl group and a $C_2$-$C_4$ alkynyl group;

each of $X^a$ and $X^b$ denotes a fluorine atom, a chlorine atom or a bromine atom;

each of $n^a$ and $n^b$ denotes 0 to 5;

each Y denotes a halogen atom, a $C_1$-$C_3$ alkyl group, a $C_1$-$C_3$ haloalkyl group, a $C_1$-$C_3$ alkoxy group or a $C_1$-$C_3$ haloalkoxy group;

m denotes 0 to 3;

A denotes a nitrogen atom.

3. The azole derivative according to claim 1 wherein the alkyl group in $R^a$ and $R^b$ in Formula (I) described above denotes a $C_1$-$C_3$ alkyl group;

each of $X^a$ and $X^b$ denotes a chlorine atom or a bromine atom;

each of $n^a$ and $n^b$ denotes 0 to 3;

each Y denotes a halogen atom, a $C_1$-$C_2$ alkyl group, a $C_1$-$C_2$ haloalkyl group or a $C_1$-$C_2$ haloalkoxy group;

m denotes 0 to 2.

4. The azole derivative according to claim 1 wherein each of $n^a$, $n^b$ and m in Formula (I) described above denotes 0 to 1, and each Y denotes a halogen atom.

5. A method for producing an azole derivative of Formula (Ia) comprising a step for substituting a halogen atom-substitutable leaving group in an intermediate compound represented by Formula (II) with a halogen atom thereby obtaining a compound represented by Formula (Ia):

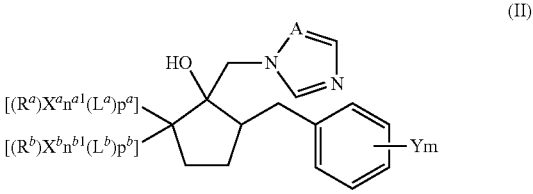

(II)

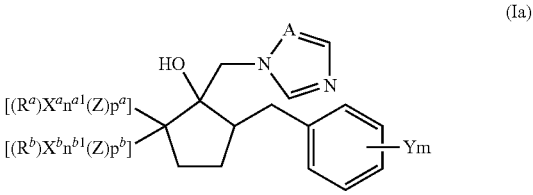

(Ia)

wherein each of $R^a$ and $R^b$ may be substituted with $X^a$, $X^b$, $L^a$, $L^b$ or Z;

Z denotes a halogen atom;

each of $L^a$ and $L^b$ denotes a halogen atom-substitutable leaving group;

"$n^{a1}+p^{a}$" denotes 0 or the number of hydrogen atoms substituted with $X^a$ or $L^a$ or Z among the hydrogen atoms in $R^a$; "$n^{b1}+p^{b}$" denotes 0 or the number of hydrogen atoms substituted with $X^b$ or $L^b$ or Z among the hydrogen atoms in $R^b$;

"$p^a+p^b$" denotes 1 or more; when $n^{a1}$ denotes 2 or more then each $X^a$ may be same or different; when $n^{b1}$ denotes 2 or more then each $X^b$ may be same or different.

6. A method for producing the azole derivative according to claim 1 comprising a step for subjecting a carbonyl compound represented by Formula (V) to conversion into an oxirane thereby obtaining an oxirane derivative represented by Formula (III) which is then reacted with a compound represented by Formula (IV) thereby producing a compound of Formula (I):

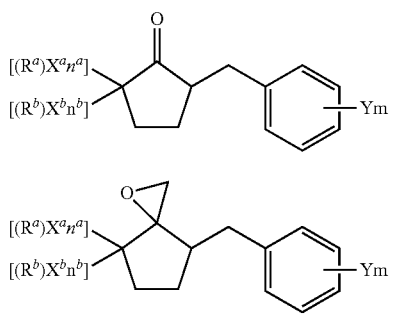

(V)

(III)

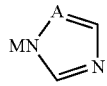

(IV)

wherein M denotes a hydrogen atom or an alkaline metal.

7. A method for producing the azole derivative according to claim 1 comprising a step for subjecting an oxetane compound represented by Formula (XVI) to ring opening using a halogenic acid thereby producing a compound of Formula (I)

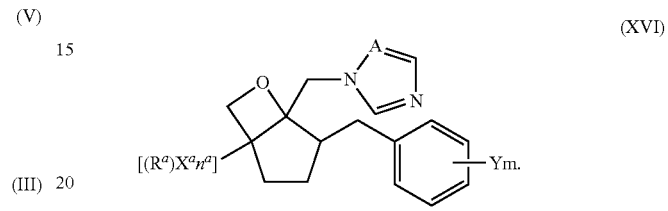

(XVI)

8. An agro-horticultural agent or an industrial material protecting agent containing as an active ingredient the azole derivative according to claim 1.

* * * * *